United States Patent
Abreu

(10) Patent No.: US 12,310,701 B2
(45) Date of Patent: May 27, 2025

(54) DEVICE FOR MEASURING THE INFRARED OUTPUT OF THE ABREU BRAIN THERMAL TUNNEL

(71) Applicant: Brain Tunnelgenix Technologies Corp., Aventura, FL (US)

(72) Inventor: Marcio Marc Abreu, Aventura, FL (US)

(73) Assignee: Brain Tunnelgenix Technologies Corp., Aventura, FL (US)

( * ) Notice: Subject to any disclaimer, the term of this patent is extended or adjusted under 35 U.S.C. 154(b) by 0 days.

(21) Appl. No.: 18/593,134

(22) Filed: Mar. 1, 2024

(65) Prior Publication Data

US 2024/0252044 A1     Aug. 1, 2024

Related U.S. Application Data

(60) Continuation of application No. 16/542,394, filed on Aug. 16, 2019, now Pat. No. 11,963,742, which is a
(Continued)

(51) Int. Cl.
*A61B 5/01*     (2006.01)
*A61B 5/00*     (2006.01)
(Continued)

(52) U.S. Cl.
CPC .............. *A61B 5/01* (2013.01); *A61B 5/0064* (2013.01); *A61B 5/4064* (2013.01);
(Continued)

(58) Field of Classification Search
CPC ....... A61B 5/01; A61B 5/0064; A61B 5/4064; A61B 5/6814; A61B 5/6819;
(Continued)

(56) References Cited

U.S. PATENT DOCUMENTS 1,132,426 A * 3/1915 Beach ..................... G01K 1/14
374/194
3,463,885 A * 8/1969 Upton .................... G02C 11/10
434/112
(Continued)

FOREIGN PATENT DOCUMENTS

CN         2398565 Y     9/2000
CN         2446955 Y     9/2001
(Continued)

OTHER PUBLICATIONS

A "Communication pursuant to Article 94(3) EPC," issued by the European Patent Office dated Jan. 27, 2009, which corresponds to European Patent Application No. 03 754 363.4-1265.
(Continued)

*Primary Examiner* — Nathaniel T Woodward
*Assistant Examiner* — Philip L Cotey
(74) *Attorney, Agent, or Firm* — Studebaker Brackett PLLC

(57) ABSTRACT

A medical device for the measurement of brain temperature data through the Abreu brain thermal tunnel (ABTT) is described. Brain temperature measurement is the key and universal indicator of both disease and health equally, and is the only vital sign that cannot be artificially changed by emotional states. Currently, brain temperature is difficult to measure. However, the present disclosure describes a device that readily locates the Abreu brain thermal tunnel, and is configured to provide a non-contact temperature reading of the brain. Embodiments of the disclosed device enable an individual to measure their own temperature and enable medical professionals to measure the temperature of others.

20 Claims, 35 Drawing Sheets

Related U.S. Application Data continuation of application No. 15/972,605, filed on May 7, 2018, now Pat. No. 10,383,525, which is a division of application No. 14/593,848, filed on Jan. 9, 2015, now Pat. No. 10,335,040.

(60) Provisional application No. 61/926,155, filed on Jan. 10, 2014.

(51) Int. Cl.
| | | |
|---|---|---|
| *G01J 5/00* | | (2022.01) |
| *G01J 5/02* | | (2022.01) |
| *G01J 5/04* | | (2006.01) |
| *G01J 5/20* | | (2006.01) |
| *G06Q 30/0251* | | (2023.01) |
| *A61B 5/05* | | (2021.01) |
| *A61B 5/245* | | (2021.01) |

(52) U.S. Cl.
CPC .......... *A61B 5/6814* (2013.01); *A61B 5/6819* (2013.01); *A61B 5/6835* (2013.01); *A61B 5/742* (2013.01); *G01J 5/0025* (2013.01); *G01J 5/0205* (2013.01); *G01J 5/0265* (2013.01); *G01J 5/04* (2013.01); *G01J 5/047* (2013.01); *G06Q 30/0271* (2013.01); *A61B 5/015* (2013.01); *A61B 5/05* (2013.01); *A61B 5/245* (2021.01); *A61B 5/441* (2013.01); *A61B 5/7445* (2013.01)

(58) Field of Classification Search
CPC ....... A61B 5/6835; A61B 5/742; A61B 5/015; A61B 5/05; A61B 5/245; A61B 5/441; A61B 5/7445; G01J 5/0025; G01J 5/0205; G01J 5/0265; G01J 5/04; G01J 5/047; G06Q 30/0271
See application file for complete search history.

(56) References Cited

U.S. PATENT DOCUMENTS

| | | | | |
|---|---|---|---|---|
| 3,531,642 A | * | 9/1970 | Bowling | A61B 5/015 600/549 |
| 3,545,260 A | * | 12/1970 | Kroger | A61B 3/165 600/400 |
| 3,585,849 A | * | 6/1971 | Grolman | A61B 3/165 600/401 |
| 3,626,757 A | * | 12/1971 | Benzinger | G01K 13/20 374/E13.002 |
| 3,724,263 A | * | 4/1973 | Rose | A61B 3/16 600/399 |
| 3,769,961 A | * | 11/1973 | Fatt | A61B 5/150015 600/356 |
| 3,897,272 A | * | 7/1975 | Medlar | G01K 1/14 374/208 |
| 3,897,790 A | * | 8/1975 | Magilton | A61F 7/12 607/105 |
| 3,963,019 A | * | 6/1976 | Quandt | A61B 5/14558 600/319 |
| 4,186,184 A | * | 1/1980 | Zaffaroni | A61F 9/0017 424/85.1 |
| 4,231,052 A | * | 10/1980 | Day | H01L 27/14669 377/67 |
| 4,297,685 A | * | 10/1981 | Brainard, II | A61B 5/01 600/549 |
| 4,305,399 A | * | 12/1981 | Beale | A61B 3/16 73/728 |
| 4,312,358 A | * | 1/1982 | Barney | A61B 5/222 377/5 |
| 4,321,261 A | * | 3/1982 | Ellis | A61L 12/08 524/556 |
| 4,330,299 A | * | 5/1982 | Cerami | G01N 33/66 436/95 |
| 4,331,161 A | * | 5/1982 | Patel | A61B 5/276 600/549 |
| 4,344,315 A | * | 8/1982 | Moxon | G01N 33/389 374/44 |
| 4,344,438 A | * | 8/1982 | Schultz | A61B 5/1459 600/341 |
| 4,386,831 A | * | 6/1983 | Grounauer | A61B 3/10 600/383 |
| 4,444,990 A | * | 4/1984 | Villar | G01K 7/04 374/208 |
| 4,485,820 A | * | 12/1984 | Flower | A61B 5/14555 600/320 |
| 4,488,558 A | * | 12/1984 | Simbruner | A61B 5/288 600/549 |
| 4,595,020 A | * | 6/1986 | Palti | G01K 7/023 374/E13.002 |
| 4,597,392 A | * | 7/1986 | Opitz | A61B 3/0008 600/479 |
| 4,628,938 A | * | 12/1986 | Lee | A61B 3/16 600/405 |
| 4,629,424 A | * | 12/1986 | Lauks | A61B 5/11 455/100 |
| 4,771,792 A | * | 9/1988 | Seale | A61B 5/205 702/56 |
| 4,784,149 A | * | 11/1988 | Berman | G01J 5/08 374/129 |
| 4,830,014 A | * | 5/1989 | Goodman | A61B 5/6838 600/479 |
| 4,846,196 A | * | 7/1989 | Wiksell | A61N 1/06 600/549 |
| 4,860,755 A | * | 8/1989 | Erath | A61B 3/16 600/405 |
| 4,922,913 A | * | 5/1990 | Waters, Jr. | A61B 3/16 600/398 |
| 4,944,303 A | * | 7/1990 | Katsuragi | A61B 3/165 600/401 |
| 4,947,849 A | * | 8/1990 | Takahashi | A61B 3/165 600/401 |
| 4,951,671 A | * | 8/1990 | Coan | A61B 3/16 600/587 |
| 4,979,831 A | * | 12/1990 | Schertz | G01K 1/08 374/208 |
| 5,005,577 A | * | 4/1991 | Frenkel | A61B 5/0031 600/398 |
| 5,046,482 A | * | 9/1991 | Everest | G01J 5/0806 374/E13.003 |
| 5,062,432 A | * | 11/1991 | James | G01K 13/20 600/549 |
| 5,076,274 A | * | 12/1991 | Matsumoto | A61B 3/165 600/401 |
| 5,109,852 A | * | 5/1992 | Kaye | A61B 3/16 600/398 |
| 5,115,815 A | * | 5/1992 | Hansen | A61B 5/01 600/549 |
| 5,148,807 A | * | 9/1992 | Hsu | A61B 3/165 600/402 |
| 5,165,409 A | * | 11/1992 | Coan | A61B 3/16 600/401 |
| 5,179,953 A | * | 1/1993 | Kursar | A61B 3/16 600/399 |
| 5,183,044 A | * | 2/1993 | Nishio | A61B 5/02416 600/398 |
| 5,190,039 A | * | 3/1993 | Takeuchi | A61B 5/14539 600/311 |
| 5,209,231 A | * | 5/1993 | Cote | G01N 21/21 600/316 |
| 5,217,015 A | * | 6/1993 | Kaye | A61B 5/0002 600/587 |
| 5,222,495 A | * | 6/1993 | Clarke | A61B 5/1455 356/41 |
| 5,222,809 A | * | 6/1993 | Ehrenkranz | A61B 10/007 374/E13.002 |
| 5,246,867 A | * | 9/1993 | Lakowicz | G01N 33/582 436/95 |

(56) References Cited

U.S. PATENT DOCUMENTS

| | | | | |
|---|---|---|---|---|
| 5,251,627 A * | 10/1993 | Morris | A61B 3/165 | 600/398 |
| 5,255,979 A * | 10/1993 | Ferrari | G01K 13/25 | 600/549 |
| 5,295,495 A * | 3/1994 | Maddess | A61B 5/4863 | 600/383 |
| 5,297,554 A * | 3/1994 | Glynn | A61B 5/6821 | 600/476 |
| 5,341,805 A * | 8/1994 | Stavridi | A61B 5/0071 | 600/316 |
| 5,342,283 A * | 8/1994 | Good | C23C 14/564 | 376/202 |
| 5,342,789 A * | 8/1994 | Chick | A61K 49/0004 | 436/805 |
| 5,352,411 A * | 10/1994 | Khuri | G01N 21/77 | 422/430 |
| 5,356,780 A * | 10/1994 | Robinson | G01N 33/542 | 435/176 |
| 5,375,595 A * | 12/1994 | Sinha | A61B 3/165 | 600/402 |
| 5,383,452 A * | 1/1995 | Buchert | A61B 5/14558 | 600/347 |
| 5,433,197 A * | 7/1995 | Stark | A61B 5/14532 | 600/319 |
| 5,435,307 A * | 7/1995 | Friauf | A61B 5/0059 | 600/478 |
| 5,441,476 A * | 8/1995 | Kitado | A61M 21/00 | 600/26 |
| 5,522,662 A * | 6/1996 | Shiokawa | G01J 5/046 | 374/E13.003 |
| 5,636,635 A * | 6/1997 | Massie | A61B 3/165 | 600/587 |
| 5,653,239 A * | 8/1997 | Pompei | G01J 5/0893 | 600/549 |
| 5,664,578 A * | 9/1997 | Boczan | A61B 5/01 | 600/549 |
| 5,673,692 A * | 10/1997 | Schulze | A61B 5/6817 | 356/41 |
| 5,711,915 A * | 1/1998 | Siegmund | G01N 33/582 | 422/50 |
| 5,796,341 A * | 8/1998 | Stratiotis | F16P 1/00 | 340/532 |
| 5,813,982 A * | 9/1998 | Baratta | G01J 5/0022 | 600/398 |
| 5,817,008 A * | 10/1998 | Rafert | A61B 5/14552 | 600/323 |
| 5,820,557 A * | 10/1998 | Hattori | A61B 5/1455 | 600/319 |
| 5,830,139 A * | 11/1998 | Abreu | A61B 5/1455 | 600/404 |
| 5,833,633 A * | 11/1998 | Sarvazyan | A61B 8/485 | 73/818 |
| 5,854,078 A * | 12/1998 | Asher | G01N 31/222 | 436/95 |
| 5,860,934 A * | 1/1999 | Sarvazyan | A61B 1/0052 | 600/587 |
| 5,862,803 A * | 1/1999 | Besson | H03F 3/45103 | 128/903 |
| 5,898,004 A * | 4/1999 | Asher | G01N 21/4788 | 252/582 |
| 5,984,880 A * | 11/1999 | Lander | G06F 3/016 | 600/595 |
| 5,994,701 A * | 11/1999 | Tsuchimoto | G01J 5/0806 | 250/252.1 |
| 6,011,984 A * | 1/2000 | Van Antwerp | C12Q 1/005 | 600/317 |
| 6,028,323 A * | 2/2000 | Liu | H10F 77/146 | 257/85 |
| 6,040,194 A * | 3/2000 | Chick | A61K 49/0006 | 436/805 |
| 6,042,266 A * | 3/2000 | Cheslock | G01J 5/021 | 600/184 |
| 6,047,203 A * | 4/2000 | Sackner | A61B 5/0006 | 600/509 |
| 6,072,180 A * | 6/2000 | Kramer | G01N 25/72 | 250/341.6 |
| 6,120,460 A * | 9/2000 | Abreu | A61B 5/14546 | 600/405 |
| 6,123,668 A * | 9/2000 | Abreu | A61F 9/0017 | 600/404 |
| 6,126,595 A * | 10/2000 | Amano | A61B 5/02 | 600/490 |
| 6,135,968 A * | 10/2000 | Brounstein | A61B 5/6838 | 600/587 |
| 6,152,875 A * | 11/2000 | Hakamata | A61B 5/14532 | 600/319 |
| 6,178,346 B1 * | 1/2001 | Amundson | A61B 1/00165 | 600/473 |
| 6,181,957 B1 * | 1/2001 | Lambert | A61B 5/14532 | 600/319 |
| 6,187,599 B1 * | 2/2001 | Asher | G01J 3/18 | 435/14 |
| 6,196,714 B1 * | 3/2001 | Bellifemine | G01J 5/08 | 374/161 |
| 6,197,534 B1 * | 3/2001 | Lakowicz | C12Q 1/485 | 435/14 |
| 6,197,928 B1 * | 3/2001 | Tsien | C07K 14/43595 | 435/69.7 |
| 6,203,193 B1 * | 3/2001 | Egawa | G01J 5/08 | 374/129 |
| 6,213,943 B1 * | 4/2001 | Abreu | A61B 5/445 | 600/404 |
| 6,256,522 B1 * | 7/2001 | Schultz | G01N 21/6428 | 600/317 |
| 6,290,658 B1 * | 9/2001 | Kolich | A42B 1/24 | 600/595 |
| 6,292,685 B1 * | 9/2001 | Pompei | G01J 5/0025 | 600/475 |
| 6,300,871 B1 * | 10/2001 | Irwin | G01K 1/024 | 374/E1.004 |
| 6,312,393 B1 * | 11/2001 | Abreu | A61B 5/1455 | 600/558 |
| 6,319,540 B1 * | 11/2001 | Van Antwerp | C12Q 1/005 | 427/2.12 |
| 6,385,473 B1 * | 5/2002 | Haines | A61B 5/0006 | 600/382 |
| 6,385,474 B1 * | 5/2002 | Rather | A61B 8/0825 | 600/407 |
| 6,423,001 B1 * | 7/2002 | Abreu | A61B 3/1241 | 600/404 |
| 6,432,050 B1 * | 8/2002 | Porat | A61B 5/031 | 600/300 |
| 6,470,893 B1 * | 10/2002 | Boesen | A61B 5/002 | 128/903 |
| 6,503,770 B1 * | 1/2003 | Ho | H01S 5/2231 | 438/42 |
| 6,529,617 B1 * | 3/2003 | Prokoski | A61B 5/1171 | 382/128 |
| 6,536,945 B2 * | 3/2003 | Rolston | G01K 17/20 | 374/30 |
| 6,542,081 B2 * | 4/2003 | Torch | G08B 25/016 | 340/576 |
| 6,543,933 B2 * | 4/2003 | Stergiopoulos | G01K 11/006 | 374/E11.003 |
| 6,544,193 B2 * | 4/2003 | Abreu | A61B 3/185 | 600/558 |
| 6,681,127 B2 * | 1/2004 | March | A61B 5/14532 | 600/319 |
| 6,731,976 B2 * | 5/2004 | Penn | A61B 5/6864 | 600/561 |
| 6,789,901 B1 * | 9/2004 | Kormos | H04N 7/183 | 362/489 |
| 6,791,087 B1 * | 9/2004 | Okumura | G01D 3/0365 | 356/213 |
| 6,846,106 B1 * | 1/2005 | Chen | A61B 5/01 | 340/407.1 |
| 7,187,960 B2 * | 3/2007 | Abreu | G01K 13/20 | 374/E13.002 |

(56) References Cited

U.S. PATENT DOCUMENTS

| | | | | |
|---|---|---|---|---|
| 7,340,293 B2* | 3/2008 | McQuilkin | G01J 5/53 | 374/129 |
| 7,346,386 B2* | 3/2008 | Pompei | A61B 5/742 | 374/129 |
| 7,515,054 B2* | 4/2009 | Torch | G06F 3/013 | 351/207 |
| 7,597,668 B2* | 10/2009 | Yarden | G01K 1/165 | 374/102 |
| 7,621,877 B2* | 11/2009 | Schnall | A61B 5/02241 | 600/481 |
| 7,689,437 B1* | 3/2010 | Teller | A61B 5/411 | 600/300 |
| 7,756,559 B2* | 7/2010 | Abreu | A61B 5/4839 | 600/309 |
| 7,787,938 B2* | 8/2010 | Pompei | A61B 5/015 | 374/100 |
| 7,837,623 B2* | 11/2010 | Aubry | A61B 8/00 | 600/437 |
| 8,103,071 B2* | 1/2012 | Schnell | G06F 3/013 | 382/128 |
| 8,172,459 B2* | 5/2012 | Abreu | A61B 5/6814 | 374/208 |
| 8,328,420 B2* | 12/2012 | Abreu | A61B 5/14532 | 374/170 |
| 8,500,271 B2* | 8/2013 | Howell | G02C 5/001 | 351/122 |
| 8,527,022 B1* | 9/2013 | Lash | A61B 5/02427 | 600/323 |
| 8,721,562 B2* | 5/2014 | Abreu | G01K 13/20 | 600/595 |
| 8,834,020 B2* | 9/2014 | Abreu | A61B 5/0046 | 250/341.1 |
| 8,849,379 B2* | 9/2014 | Abreu | A61B 5/0008 | 600/549 |
| 9,007,220 B2* | 4/2015 | Johns | G08B 21/06 | 340/576 |
| 10,123,732 B2 | 11/2018 | Abreu | | |
| 2001/0028309 A1* | 10/2001 | Torch | A61B 5/1103 | 340/576 |
| 2002/0026119 A1* | 2/2002 | Pompei | A61B 5/742 | 374/E13.003 |
| 2002/0035340 A1* | 3/2002 | Fraden | G01K 13/20 | 374/E13.002 |
| 2002/0049374 A1* | 4/2002 | Abreu | G02C 7/04 | 600/404 |
| 2002/0049389 A1* | 4/2002 | Abreu | A61B 3/0058 | 600/318 |
| 2002/0068876 A1* | 6/2002 | Pompei | G01J 5/05 | 600/549 |
| 2002/0111657 A1* | 8/2002 | Dae | A61K 31/4174 | 607/113 |
| 2002/0126731 A1* | 9/2002 | Stergiopoulos | A61B 5/0507 | 374/E11.003 |
| 2003/0055473 A1* | 3/2003 | Ramsden | A61F 7/10 | 607/109 |
| 2003/0060863 A1* | 3/2003 | Dobak, III | A61F 7/123 | 607/104 |
| 2003/0067958 A1* | 4/2003 | Jang | G01J 5/08 | 374/E1.013 |
| 2003/0108223 A1* | 6/2003 | Prokoski | A61B 5/415 | 382/209 |
| 2003/0111605 A1* | 6/2003 | Sato | G01J 5/16 | 136/227 |
| 2003/0179094 A1* | 9/2003 | Abreu | A61B 5/14532 | 128/920 |
| 2003/0210146 A1* | 11/2003 | Tseng | G01K 1/024 | 374/E1.004 |
| 2003/0212340 A1* | 11/2003 | Lussier | G01K 13/20 | 374/E13.002 |
| 2004/0039298 A1* | 2/2004 | Abreu | A61B 5/1455 | 600/558 |
| 2004/0059212 A1* | 3/2004 | Abreu | A61B 5/14551 | 374/E13.002 |
| 2004/0076316 A1* | 4/2004 | Fauci | A61B 5/015 | 382/128 |
| 2004/0082862 A1* | 4/2004 | Chance | A61B 5/0042 | 600/473 |
| 2004/0105487 A1* | 6/2004 | Chen | G01K 13/20 | 374/E13.002 |
| 2004/0125996 A1* | 7/2004 | Eddowes | A61B 5/6888 | 382/128 |
| 2004/0146087 A1* | 7/2004 | Penney | G01K 13/20 | 374/170 |
| 2004/0152991 A1* | 8/2004 | Pompei | G01J 5/0022 | 374/E13.003 |
| 2004/0154550 A1* | 8/2004 | McQuilkin | A61B 5/415 | 119/174 |
| 2004/0170216 A1* | 9/2004 | Russak | G01K 13/20 | 374/E13.002 |
| 2004/0210159 A1* | 10/2004 | Kibar | A61B 5/165 | 128/898 |
| 2004/0242976 A1* | 12/2004 | Abreu | A61B 5/746 | 600/315 |
| 2004/0246548 A1* | 12/2004 | Papuchon | G02B 27/1086 | 250/234 |
| 2005/0250996 A1* | 11/2005 | Shirai | A61B 3/113 | 600/549 |
| 2006/0122473 A1* | 6/2006 | Kill | G01J 5/04 | 374/E1.004 |
| 2006/0215728 A1* | 9/2006 | Jang | G01J 5/02 | 374/121 |
| 2006/0264726 A1* | 11/2006 | Mannheimer | A41D 20/00 | 600/340 |
| 2007/0055171 A1* | 3/2007 | Fraden | G01K 1/165 | 374/E7.042 |
| 2007/0219434 A1* | 9/2007 | Abreu | A61B 5/015 | 374/E13.002 |
| 2008/0043809 A1* | 2/2008 | Herbert | G01K 1/026 | 374/E1.005 |
| 2008/0194983 A1 | 8/2008 | Laurence et al. | | |
| 2008/0200830 A1* | 8/2008 | Pompei | A61B 5/742 | 600/549 |
| 2009/0105605 A1* | 4/2009 | Abreu | A61B 5/0075 | 600/549 |
| 2009/0157056 A1* | 6/2009 | Ferren | A61B 5/0031 | 604/891.1 |
| 2010/0011389 A1* | 1/2010 | Lee | H04N 21/475 | 725/109 |
| 2010/0020475 A1* | 1/2010 | Spitaels | H01R 13/6666 | 361/656 |
| 2010/0022909 A1* | 1/2010 | Padiy | G01K 1/14 | 600/549 |
| 2010/0160809 A1 | 6/2010 | Laurence et al. | | |
| 2011/0024626 A1* | 2/2011 | O'Donnell | G01N 1/2214 | 73/28.01 |
| 2011/0040161 A1* | 2/2011 | Abreu | A61P 9/00 | 600/8 |
| 2011/0077547 A1* | 3/2011 | Baker, Jr. | A61B 5/01 | 600/549 |
| 2011/0092822 A1* | 4/2011 | Pompei | A61B 5/742 | 600/474 |
| 2011/0118622 A1* | 5/2011 | Sisk | G01K 13/25 | 600/549 |
| 2012/0031405 A1* | 2/2012 | Geist | A61F 7/0085 | 128/204.15 |
| 2012/0136285 A1* | 5/2012 | Korb | A61H 7/00 | 601/15 |
| 2012/0310717 A1* | 12/2012 | Kankainen | G01C 21/3647 | 705/14.4 |
| 2012/0316459 A1 | 12/2012 | Abreu | | |
| 2013/0124039 A1* | 5/2013 | Abreu | G01J 5/10 | 348/77 |
| 2013/0215928 A1* | 8/2013 | Bellifemine | A61B 5/01 | 374/121 |
| 2013/0275230 A1* | 10/2013 | Sawyer | G06Q 30/0269 | 705/14.66 |

(56) References Cited

U.S. PATENT DOCUMENTS

| | | | | |
|---|---|---|---|---|
| 2013/0292571 | A1* | 11/2013 | Mukherjee | G02B 27/48 250/339.11 |
| 2013/0332286 | A1* | 12/2013 | Medelius | A61B 5/6829 705/14.66 |
| 2014/0003462 | A1* | 1/2014 | Roth | G01K 13/20 374/E1.001 |
| 2014/0046192 | A1 | 2/2014 | Mullin et al. | |
| 2014/0088436 | A1* | 3/2014 | Roth | A61B 5/7275 600/407 |
| 2015/0148681 | A1 | 5/2015 | Abreu | |
| 2016/0019344 | A1* | 1/2016 | Singh | G16H 50/80 705/3 |
| 2019/0365240 | A1 | 12/2019 | Abreu | |

FOREIGN PATENT DOCUMENTS

| | | |
|---|---|---|
| CN | 1328432 A | 12/2001 |
| DE | 4433104 C1 | 5/1996 |
| EP | 0236028 A2 | 9/1987 |
| EP | 0411121 A2 | 2/1991 |
| EP | 2 120 681 B1 | 7/2011 |
| EP | 1 951 110 B1 | 10/2012 |
| JP | S61-48369 A | 3/1986 |
| JP | H10-075934 A | 3/1998 |
| JP | H10-239158 A | 9/1998 |
| JP | H11-164826 A | 6/1999 |
| JP | 2001-500394 A | 1/2001 |
| JP | 2001/031151 A | 2/2001 |
| JP | 2002-525132 A | 8/2002 |
| JP | 3885024 B2 | 2/2007 |
| WO | 93/01745 A1 | 2/1993 |
| WO | 97/19188 A1 | 5/1997 |
| WO | 98/22820 A1 | 5/1998 |
| WO | 99/51142 A2 | 10/1999 |
| WO | 00/10007 A2 | 2/2000 |
| WO | 00/13580 A1 | 3/2000 |
| WO | 00/16051 A1 | 3/2000 |
| WO | 00/16099 A1 | 3/2000 |
| WO | 00/18237 A1 | 4/2000 |
| WO | 00/64492 A1 | 11/2000 |
| WO | 02/03855 A1 | 1/2002 |
| WO | 02/28271 A2 | 4/2002 |
| WO | 02/067688 A1 | 9/2002 |
| WO | 2005/015163 A2 | 2/2005 |
| WO | 2010-042738 A2 | 4/2010 |
| WO | 2011011686 | 1/2011 |

OTHER PUBLICATIONS

A second "Communication pursuant to Article 94(3) EPC," issued by the European Patent Office dated Sep. 13, 2013, which corresponds to European Patent Application No. 03 754 363.4-1265.
A third "Communication pursuant to Article 94(3) EPC," issued by the European Patent Office dated Mar. 4, 2014, which corresponds to European Patent Application No. 03 754 363.4-1265.
A fourth "Communication pursuant to Article 94(3) EPC," issued by the European Patent Office dated Sep. 24, 2014, which corresponds to European Patent Application No. 03 754 363.4-1265.
English translation of an Office Action; issued by the State of Israel Department of Justice, Patent Office dated Nov. 26, 2008, which corresponds to Israeli Patent Application No. 164685.
English translation of an office action; issued by the Korean IP Office dated Dec. 26, 2011, which corresponds to Korean Patent Application No. 10-2010-7018173.
International Search Report; PCT/US03/12382; dated May 13, 2005.
International Search Report; PCT/US2006/041238; dated Aug. 31, 2007.
An office action issued by the Canadian IP Office dated Aug. 2, 2011, which corresponds to Canadian Patent Application No. 2,627,278.
A second office action issued by the Canadian IP Office dated Aug. 2, 2011, which corresponds to Canadian Patent Application No. 2,627,278.
A "Communcation pursuant to Artical 94(3) EPC," issued by the European Patent Office dated May 13, 2011, which corresponds to European Patent Application No. 06 826 452.2-2319.
English translation of an office action; issued by the State of the Israeli Department of Justice, Patent Office dated Jun. 23, 2011, which corresponds to Israeli Patent Application No. 191039.
An Examiner's first report; issued by the Australian Government, IP Australia dated Jan. 13, 2013, which corresponds to Australian Patent Application No. 201120215.
Patent Examination Report No. 1; issued by the Australian Government, IP Australia dated Dec. 13, 2013, which corresponds to Australian Patent Application No. 2012203667.
Office Action issued by the Canadian Patent Office dated Jan. 15, 2018, which corresponds to Canadian Patent Application No. 2,936229; 4pp.
International Preliminary Report on Patentability and Written Opinion dated Jul. 12, 2016, issued in corresponding International Application No. PCT/US2015/010873.
An Office Action issued by the Canadian Intellectual Property Office dated Apr. 11, 2017, which corresponds to Canadian Patent Application No. 2,936,229; 4pp.
Extended European Search Report issued by the European Patent Office dated Jul. 24, 2017, which corresponds to European Patent Application No. 15735351.7-1657; 7pp.
An Examiner's First Report; issued by the Australian Government, IP Australia dated Apr. 21, 2009, which corresponds to Australian Patent Application No. 2006306422.
An Examiner's Report No. 2; issued by the Australian Government, IP Australia dated Nov. 10, 2010, which corresponds to Australian Patent Application No. 2006306422.
English translation of an Office Action; issued by the Korean Intellectual Property Office dated Jun. 21, 2013, which corresponds to Korean Patent Application No. 10-2008-7012335.
English translation of an Office Action; issued by the Japanese Patent Office dated Nov. 17, 2011, which corresponds to Japanese Patent Application No. 2008-537828.
English translation of a Second Office Action; issued by the Japanese Patent Office dated Nov. 13, 2012, which corresponds to Japanese Patent Application No. 2008-537828.
English translation of a Third Office Action; issued by the Japanese Patent Office dated Nov. 26, 2013, which corresponds to Japanese Patent Application No. 2008-537828.
Overton, Staci. "Brain Temperature Tunnel Discovered." Medical Breakthroughs Reported by Ivanhoe, Jun. 2, 2003.
International Search Report; PCT/US2014/060199; dated Jan. 8, 2015.
International Search Report; PCT/US2014/060201; dated Mar. 3, 2015.
Dittmar, A. et al., A Non Invasive Wearable Sensor for the Measurement of Brain Temperature. Proceedings of the 28th IEEE EMBS Annual International Conference. Aug. 30-Sep. 3, 2006. pp. 900-902, New York City, USA.
An Office Action and Examination Search Report issued by the Canadian Intellectual Property Office dated Mar. 26, 2015, which corresponds to Canadian Patent Application No. 2,627,728.
International Search Report; PCTUS2015/010873; dated Apr. 10, 2015.
English translation of an Unfavorable Technical Opinion; issued by the National Institute of Industrial Property, which corresponds to Brazilian Patent Application BR122013001249-4.
RCA Technical Notes, Contact Lens Tonometer by Robert E. Morey, RCA TN No. 602, dated Dec. 1964, 2 pages.
Ophthal. Physiol. Opt., 1989, vol. 9, April, Research Note, Multiple Applications of the NCT: An Assessment of Instrument's Effect on IOP by G.E Russell and J.P.G. Bergmanson, pp. 212-214.
Arch Ophthalmol—col. 97, Mar. 1979, The Pneumatonograph—A Laboratory Study, by Robert A. Moses, M.D. and Walter J. Grodzki Jr., D.D.S., pp. 547-552.
IEEE Transactions on bio-Medical Engineering, vol. BME-14, No. 2, Apr. 1967, Miniature Passive Pressure Transensor for Implanting in the Eye, by C.C. Collins, pp. 74-83.

(56) References Cited

OTHER PUBLICATIONS

Trans. Amer. Acad. of O. & O., Jan.-Feb. 1957, Tonometer Calibration, An Attempt to Remove Discrepancies Found in the 1954 Calibration Scale for Schiotz Tonometers by Jonas S. Friedenwald, M.D., pp. 108-123.
Investigative Ophthalmology, Sep. 1971, vol. 10, No. 9, Theory and Calibration of the Schiotz Tonometer VII. Experimental Results of Tonometric Measurements: Scale Reading Versus Indentation Volume, by Robert A. Moses, and Walter J. Grodski, pp. 716-723.
The British Journal of Ophthalmology, Jun. 1920, Communications—Tonometry, by HJ. Schiotz, pp. 249-261.
American Journal of Ophthalmology, vol. 20, No. 10, Oct. 1937, Contribution to the Theory and Practice of Tonometry by Jonas S. Friedenwald, M.D., pp. 985-1024.
Ophthalmologica vol. 150, No. 5, (1965), Rheology of the Human Sclera, Unifying Formulation of Ocular Rigidity, by W. K. McEwen and Roger St. Helen, pp. 321-346.
AMA Archives of Ophthalmology, vol. 57, Apr. 1957, Tonometer Calibration, by Earle H. McBain, M.D., pp. 520-531.
The Photonics Dictionary, 1996 Book 4, 42nd Edition, pp. D-24, D153.
Manual of Skin Diseases, Fifth Edition, Gordon C. Sauer, MD., 1985, pp. 204, 373.
FM-2 Fluorotron Master Ocular Fluorophotometer, 1994 OcuMetrics, Inc.
Textbook of Biochemistry With Clinical Correlations, Second Edition, Thomas M. Devlin, Ph.D., 1986, pp. 118, 139.
Physical Optics, Third Revised Edition, Robert W. Wood, 1961, pp. 650-651.
An Examiner's First Report; issued by the Australian Governement, IP Australia dated Dec. 18, 2008, which corresponds to Australian Patent Application No. 2004-263812.
An Examiner's First Report; issued by the Australian Government, IP Australia dated Mar. 10, 2010, which corresponds to an Australian Patent Application No. 2009212808.
An Examiner's First Report; issued by the Australian Government, IP Australia dated Feb. 19, 2013, which corresponds to an Australian Patent Application No. 2009212861.
An Examiner's First Report; issued by the Australian Government, IP Australia dated Nov. 4, 2010, which corresponds to an Australian Patent Application No. 2012247045.
An office Action by the Canadian IP office dated May 3, 2012, which corresponds to Canadian Patent Application No. 2,517,869.
English Translation of a first office action and search report; issued by the state IP office of the People's Republic of China dated Jul. 21, 2014, which corresponds to Chinese Patent Application No. 201310097177 3.
English Translation of a first office action and search report; issued by the state IP office of the People's Republic of China dated Jul. 22, 2014, which corresponds to Chinese Patent Application No. 201310097142 X.
A supplementary European Search Report; issued by the European Patent Office dated Oct. 17, 2008, which corresponds to European Patent Application No. 04785841.0-1265.
A "Communication pursuant to Article 94(3) EPC," issued by the European Patent Office dated Sep. 12, 2013, which corresponds to European Patent Application No. 04785841.0-1657.
English Translation of Relevant Portion of Office Action; issued by the State of Israel Department of Justice, Patent Office dated Jul. 3, 2013, which corresponds to Israeli Patent Application No. 1704896.
English translation of Notification of Reasons for Refusal; issued by the Japanese Patent Office dated Jun. 11, 2009, which corresponds to Japanese Patent Application No. 2006-508817.
A Summarized English translation of Office Action; issued by the Japanese Patent Office dated Jan. 12, 2010, which corresponds to Japanese Patent Application No. 2006-508817.
A Summarized English translation of Office Action; issued by the Instituto Mexicano de la Propiedad Industrial dated Jul. 4, 2008, which corresponds to Patent Application No. PA/a/2005/009159.
International Search Report and Written Opinion; PCT/US2004/005496; dated May 6, 2005.
English translation of an Office Action; issued by the Japanese Patent Office dated Jan. 22, 2009, which corresponds to Japanese Patent Application No. 2004-515642.
English translation of an office action; issued by the National Institute of Industrial Property, which corresponds to Brazilian Patent Application PI0309579-9.
English translation of an office action; issued by the National Institute of Industrial Property dated Jul. 1, 2013, which corresponds to Brazilian Patent Application PI0309579-9.
English translation of the first office action, and search report; issued by the State IP Office of the People's Republic of China dated Jun. 4, 2014, which corresponds to Chinese Patent Application No. 201210361917.5.

\* cited by examiner

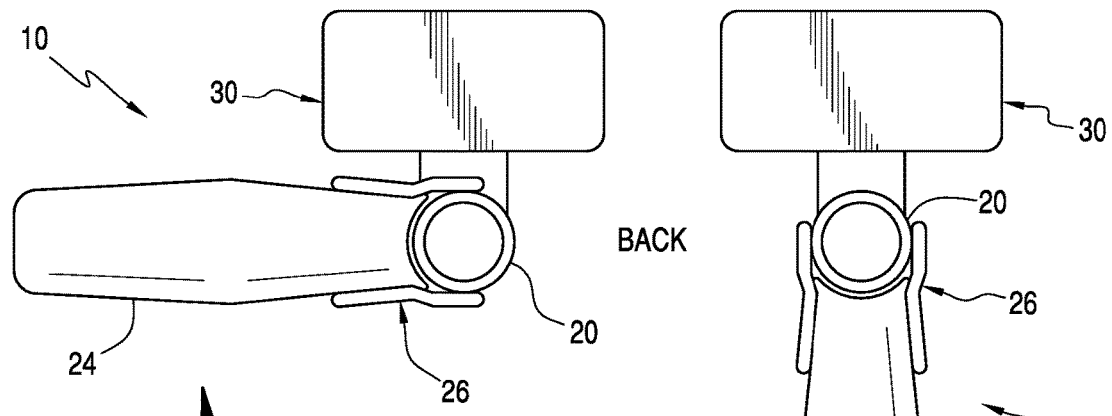
FIG. 3
FIG. 4
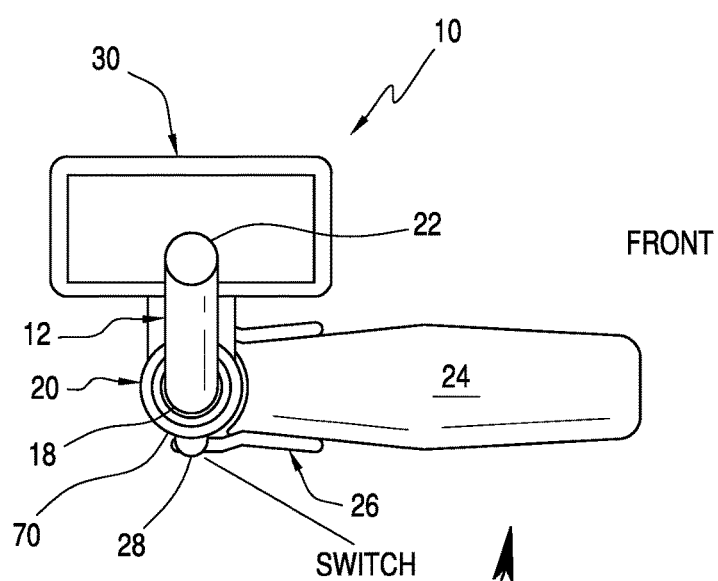
FIG. 5
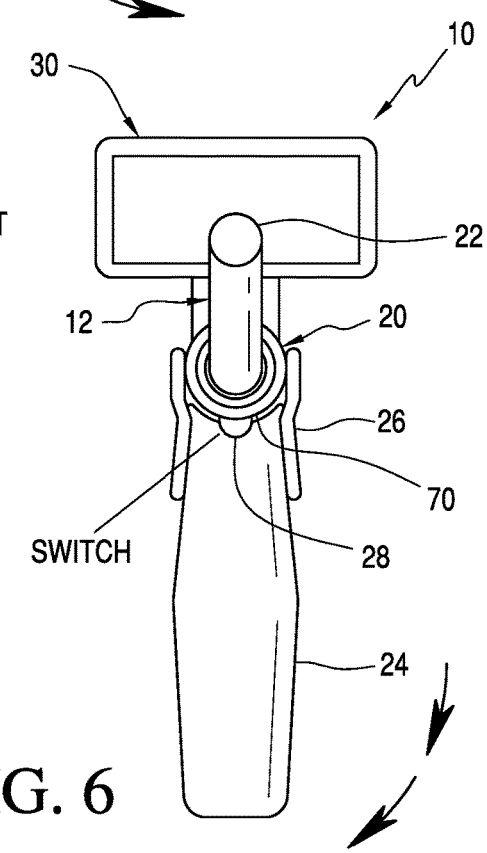
FIG. 6

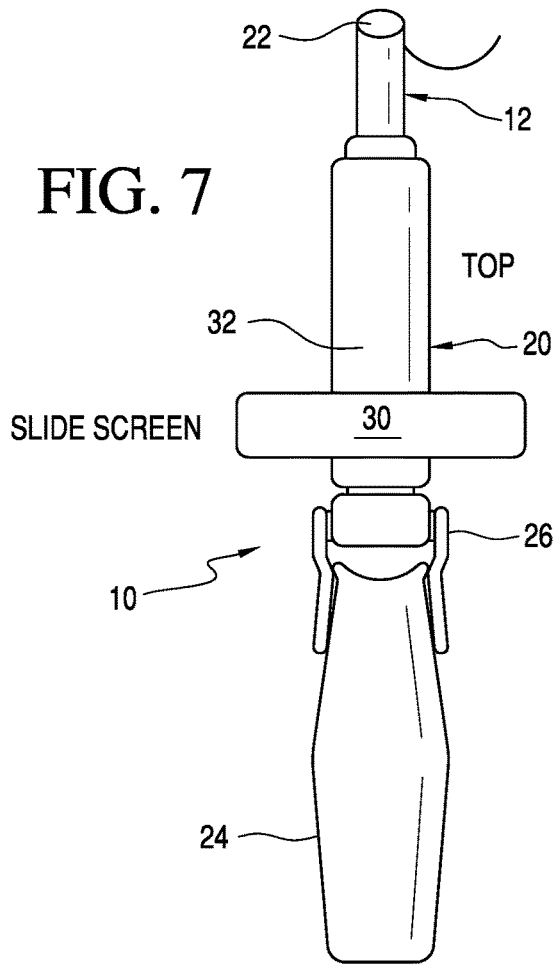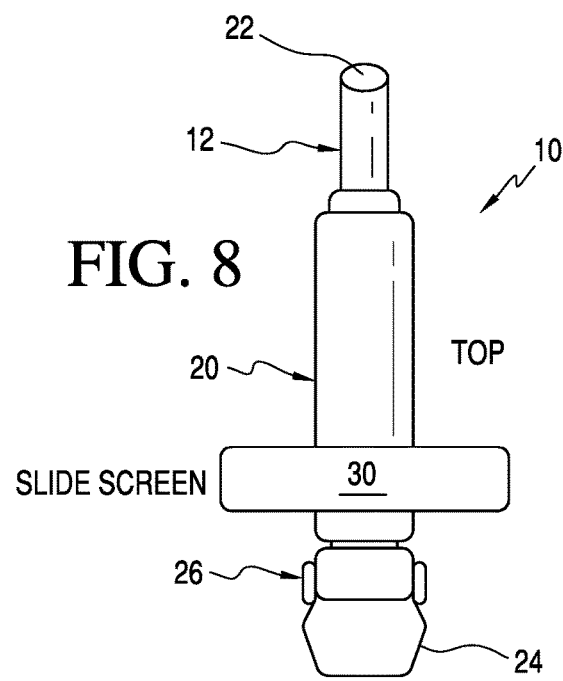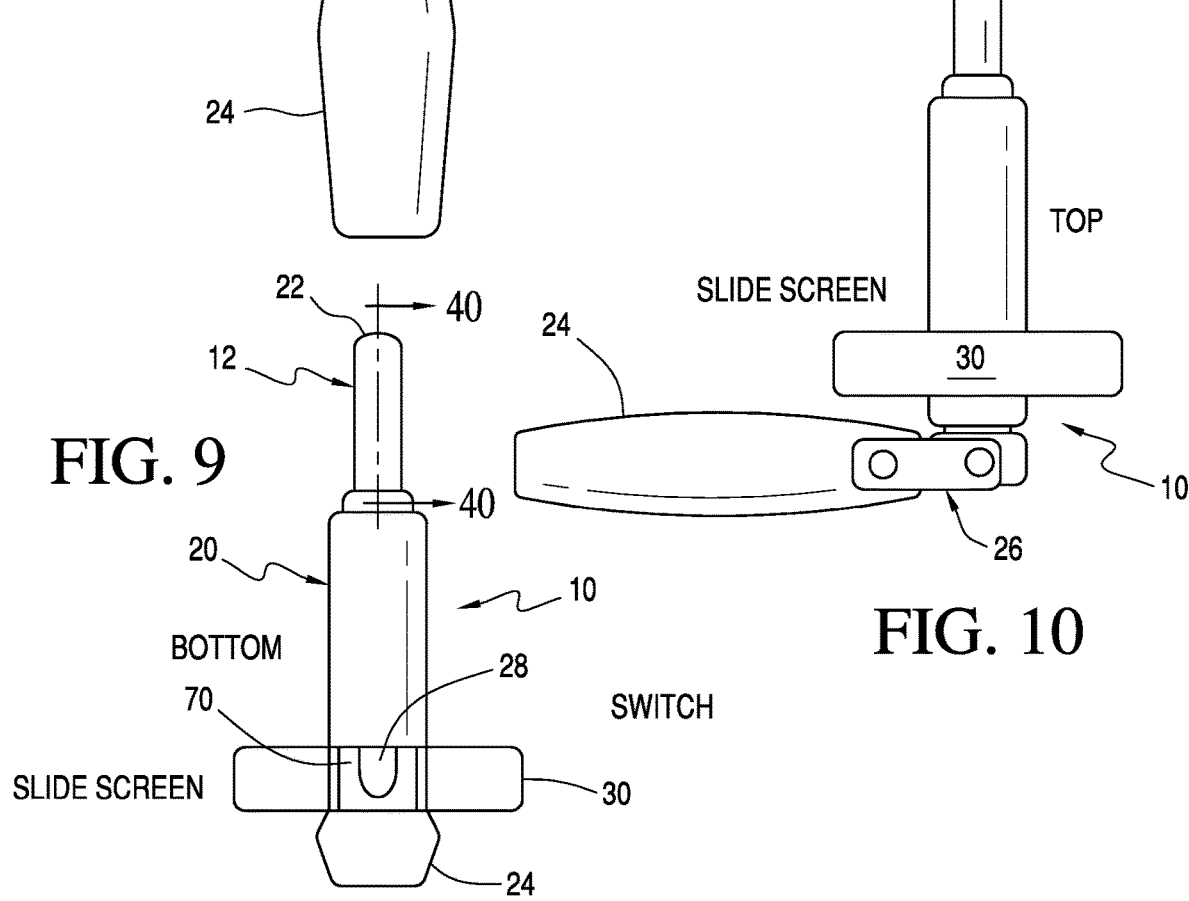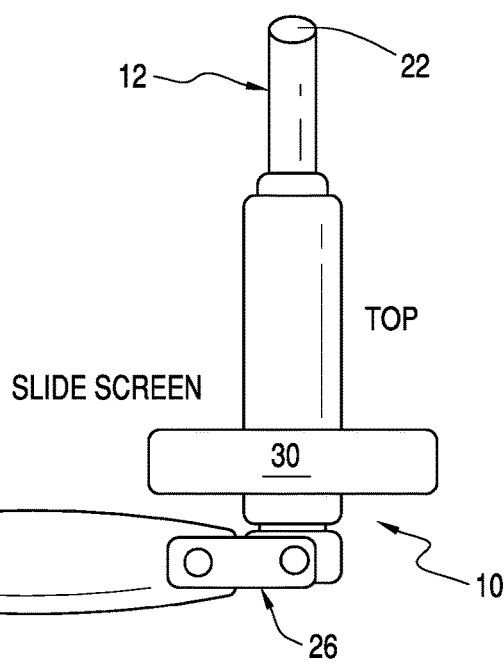

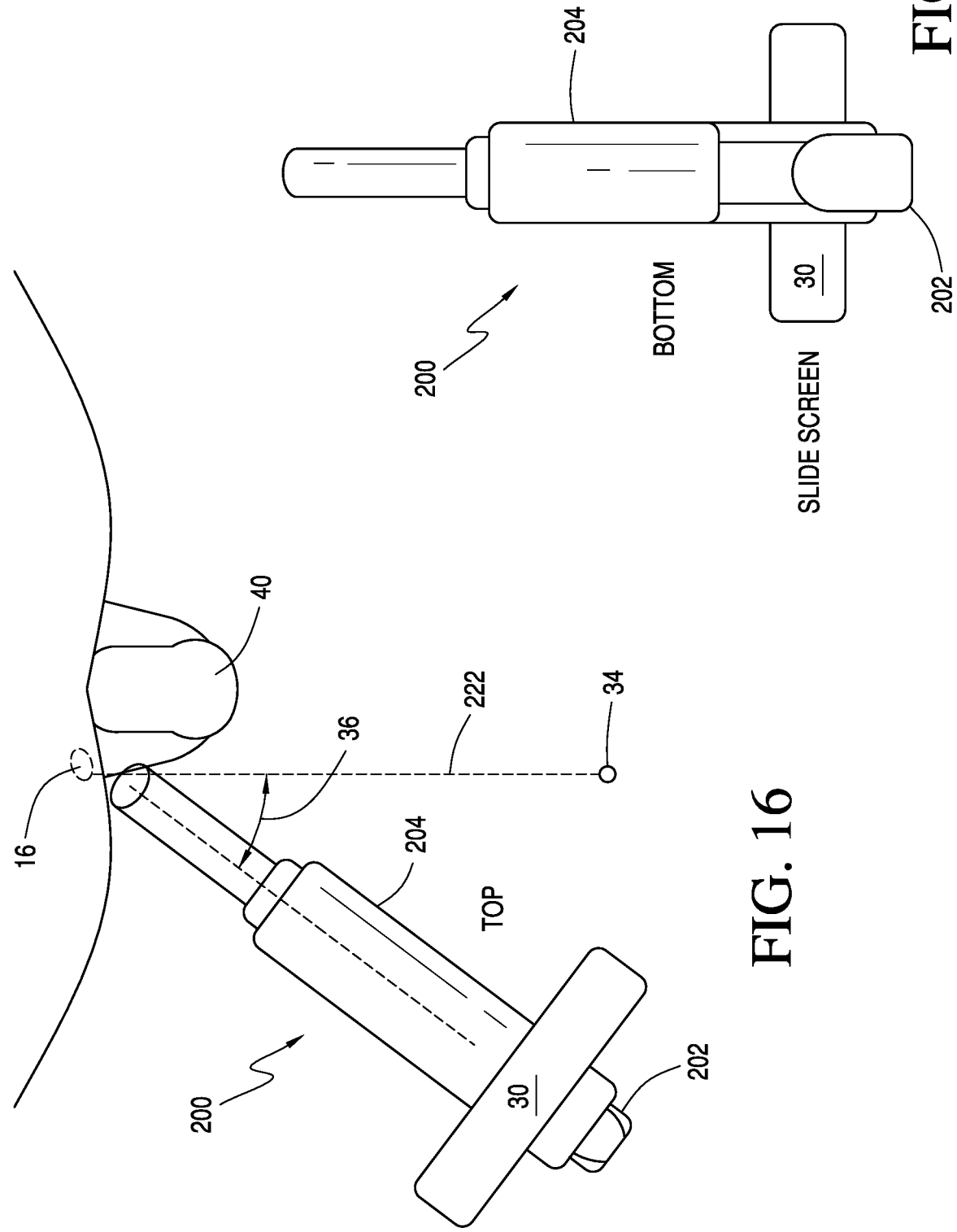

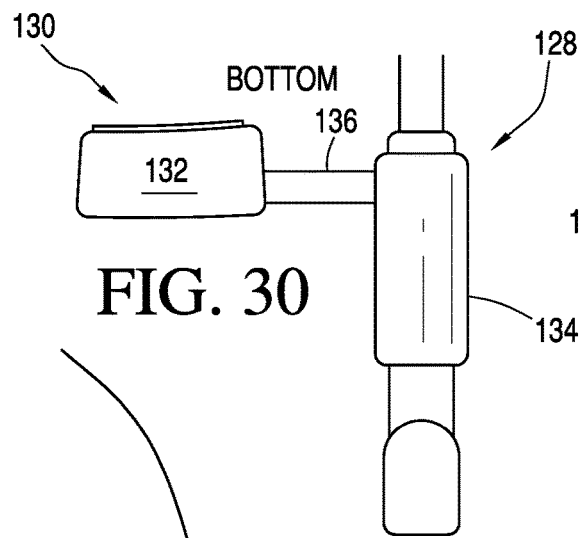
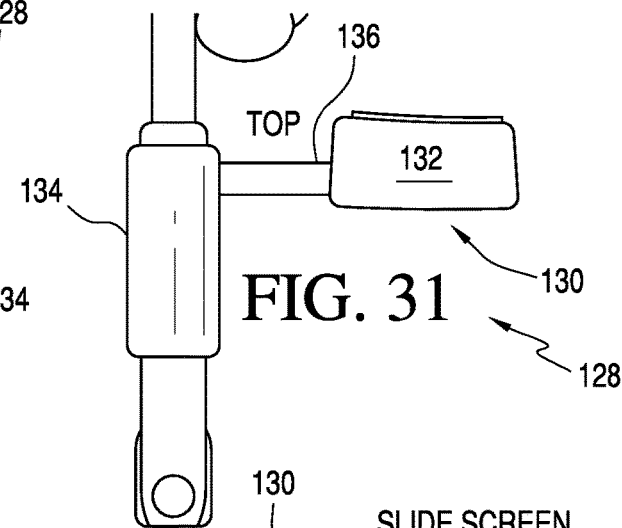
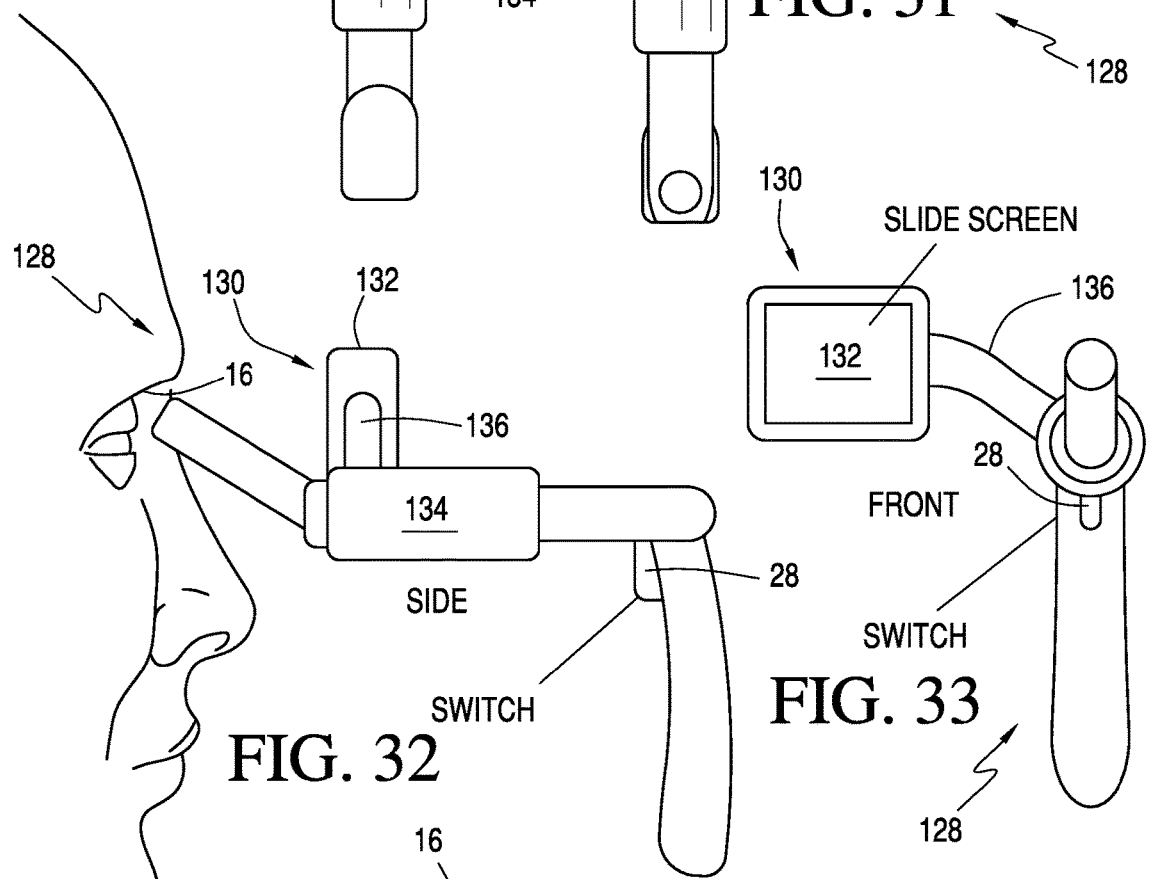
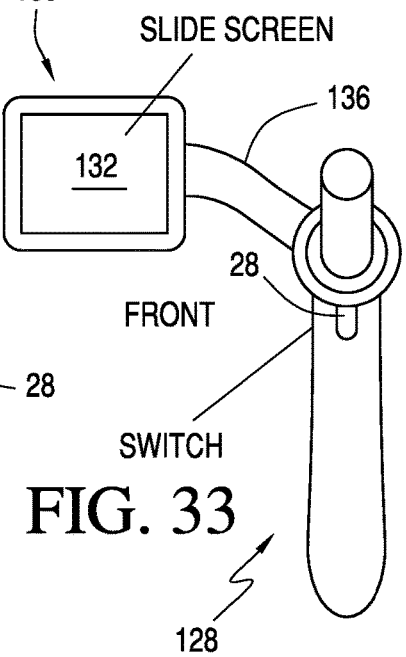
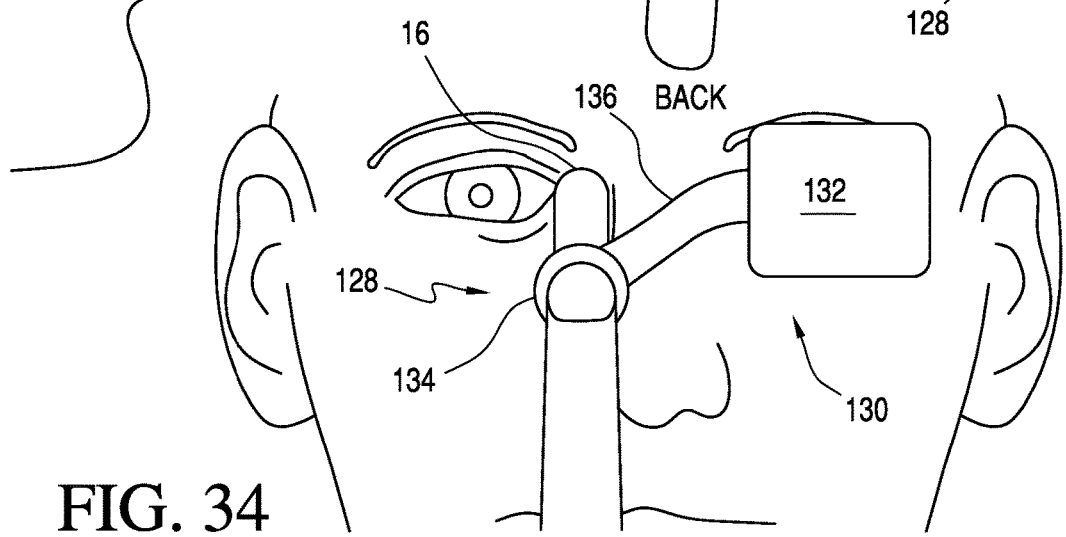

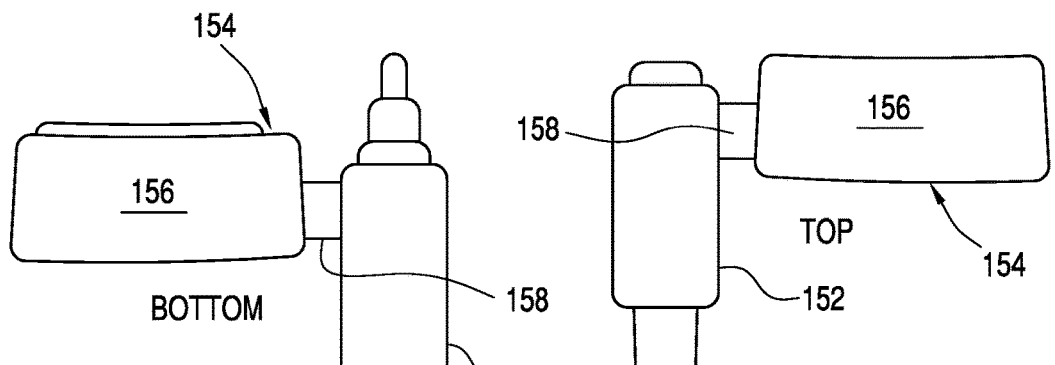
FIG. 35 BOTTOM
FIG. 36 TOP
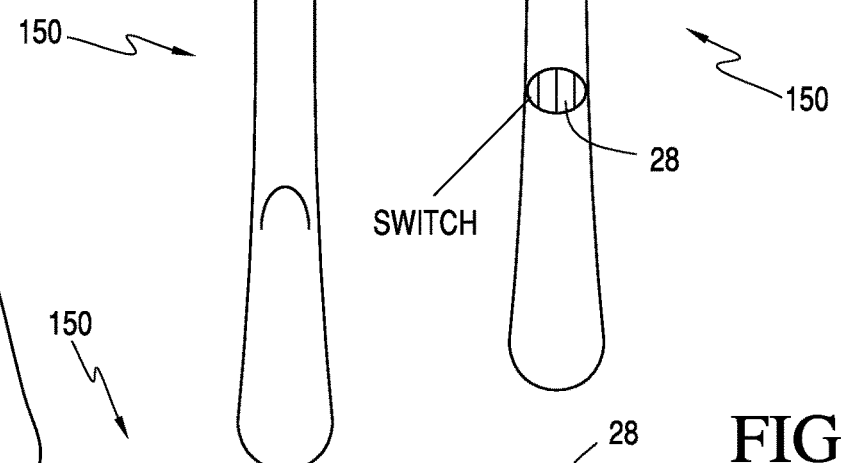
SWITCH
FIG. 37
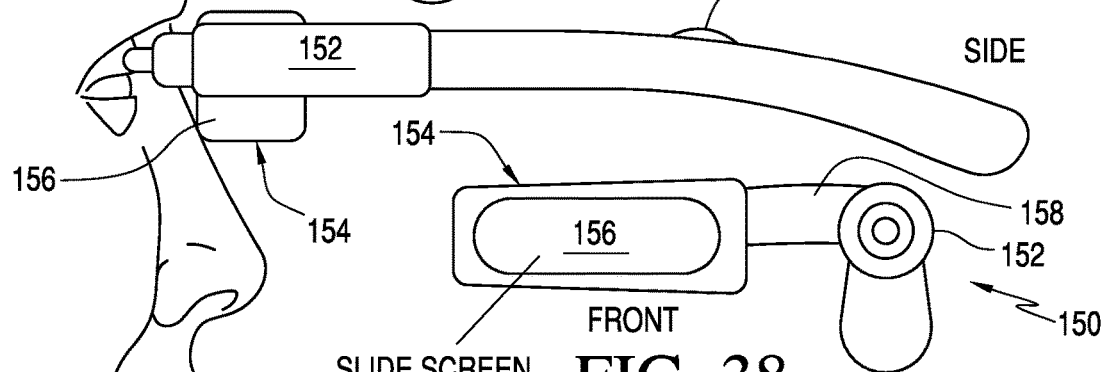
SIDE
FIG. 38 FRONT SLIDE SCREEN
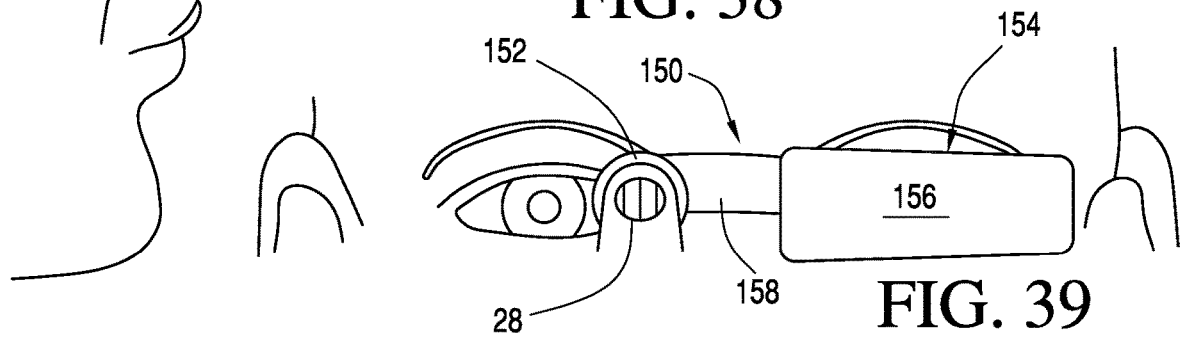
FIG. 39

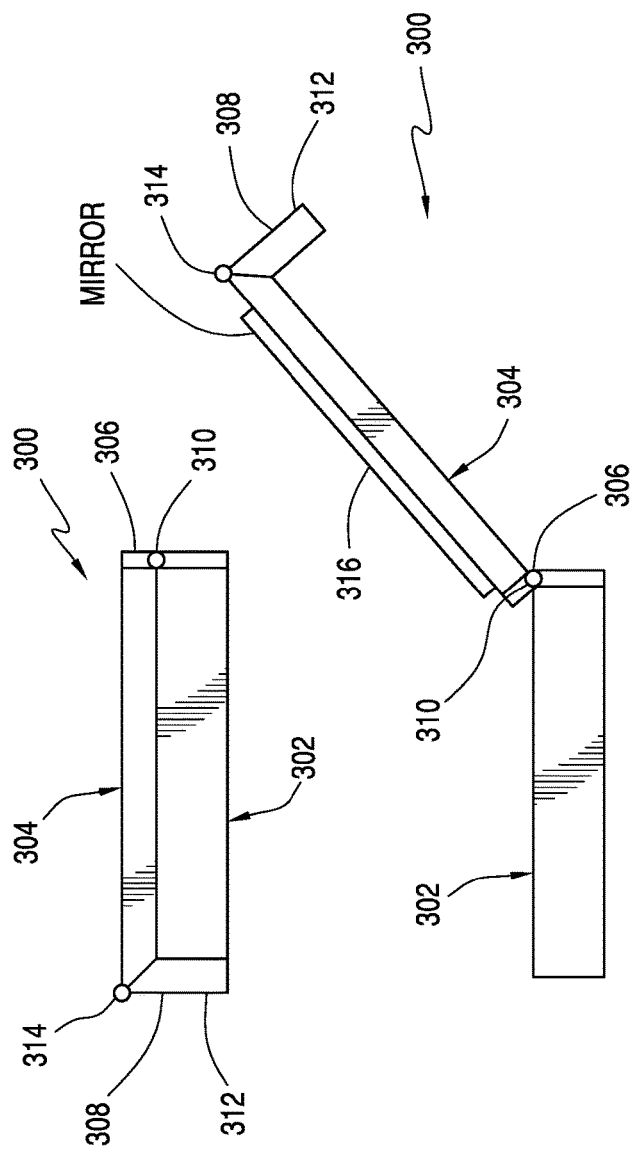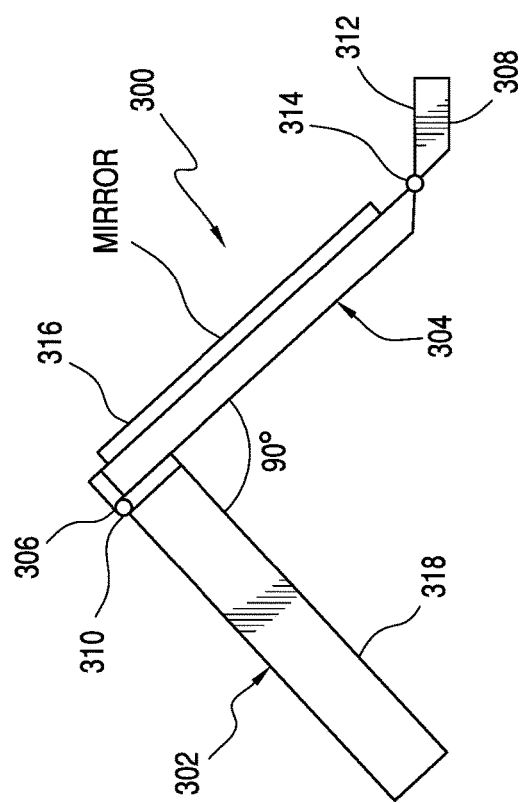
FIG. 49
FIG. 50
FIG. 51

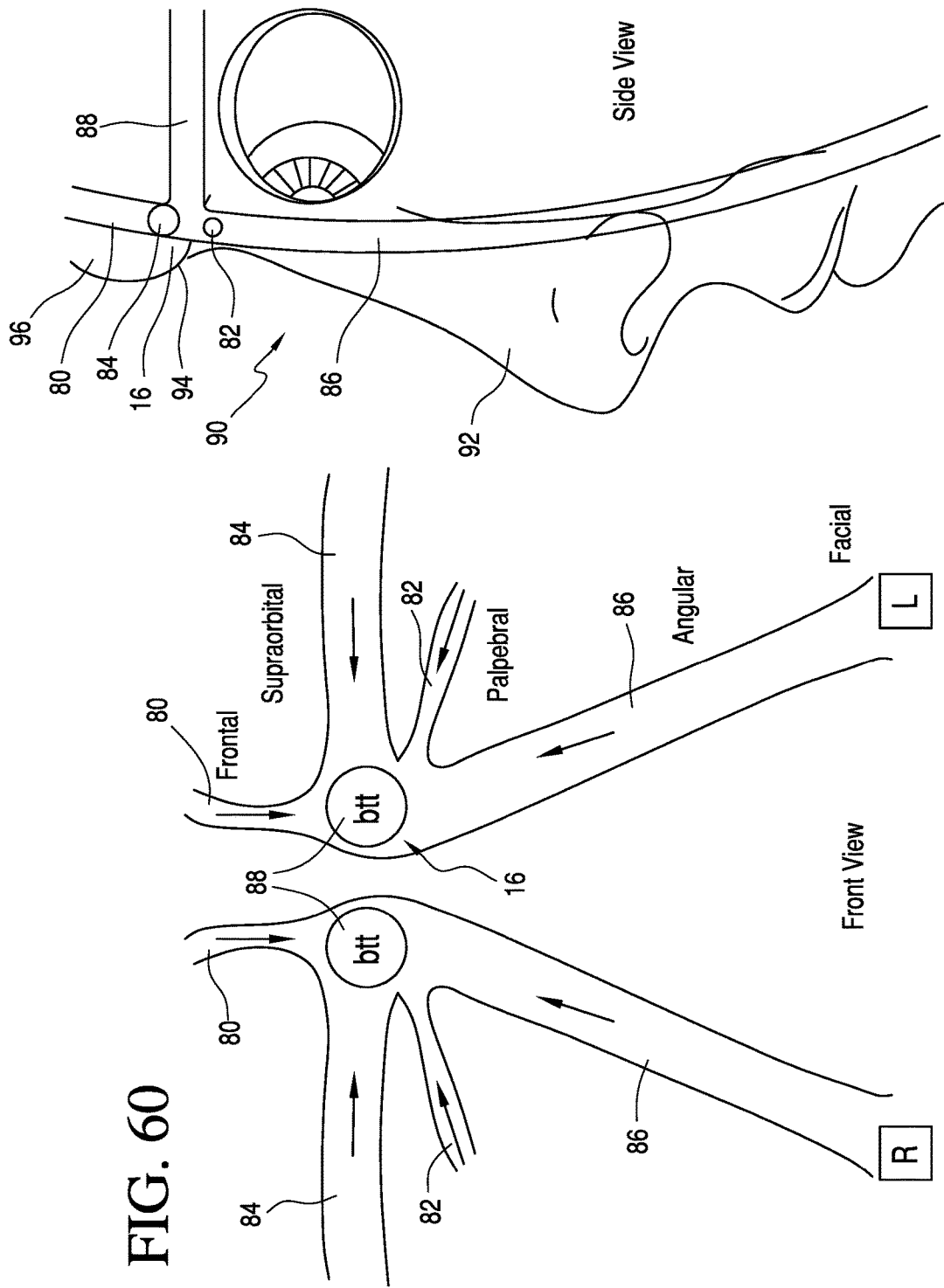

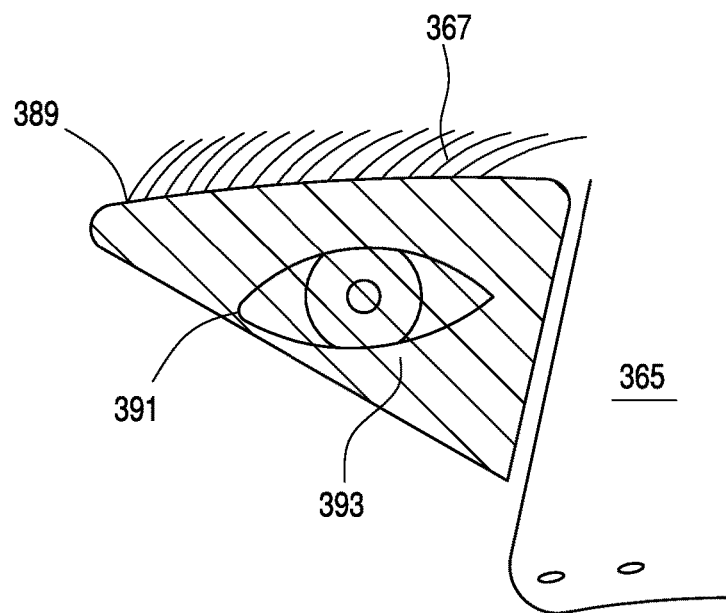
FIG. 63G
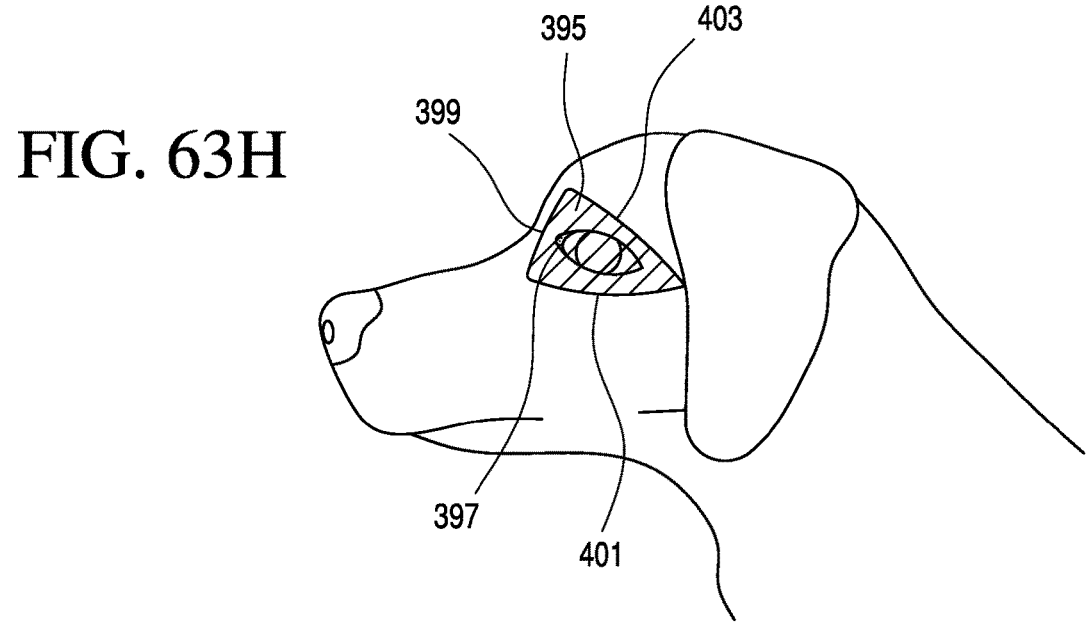
FIG. 63H

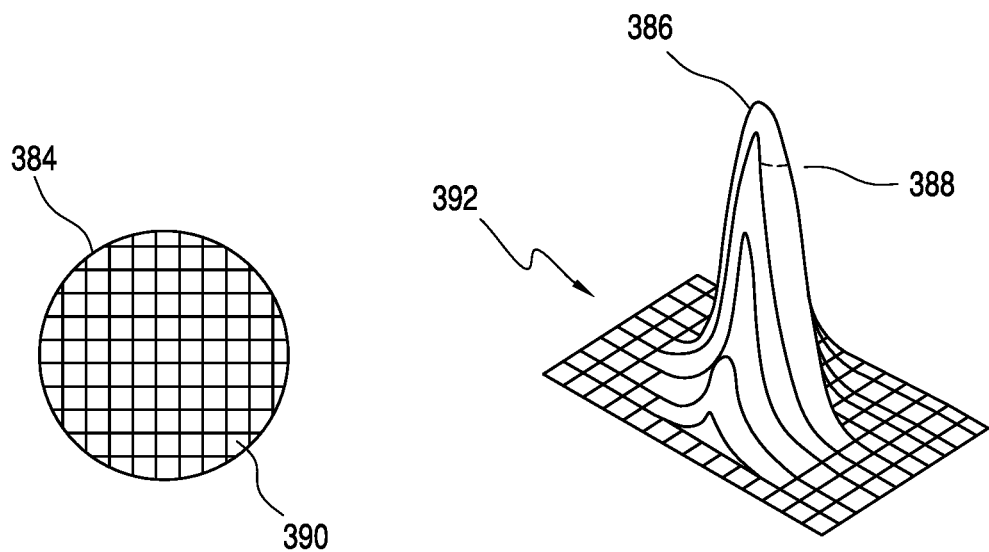
FIG. 66A  FIG. 66B
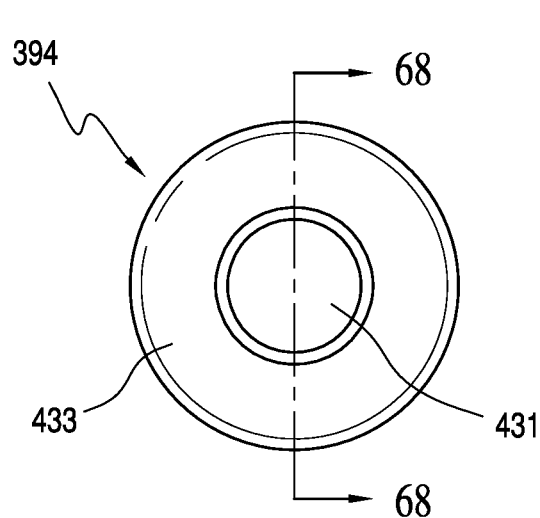
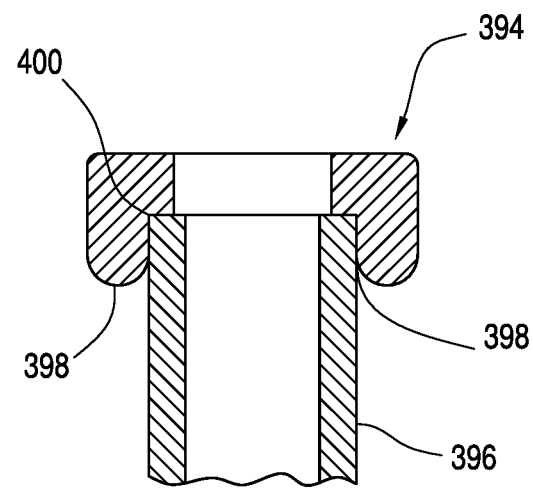
FIG. 67  FIG. 68

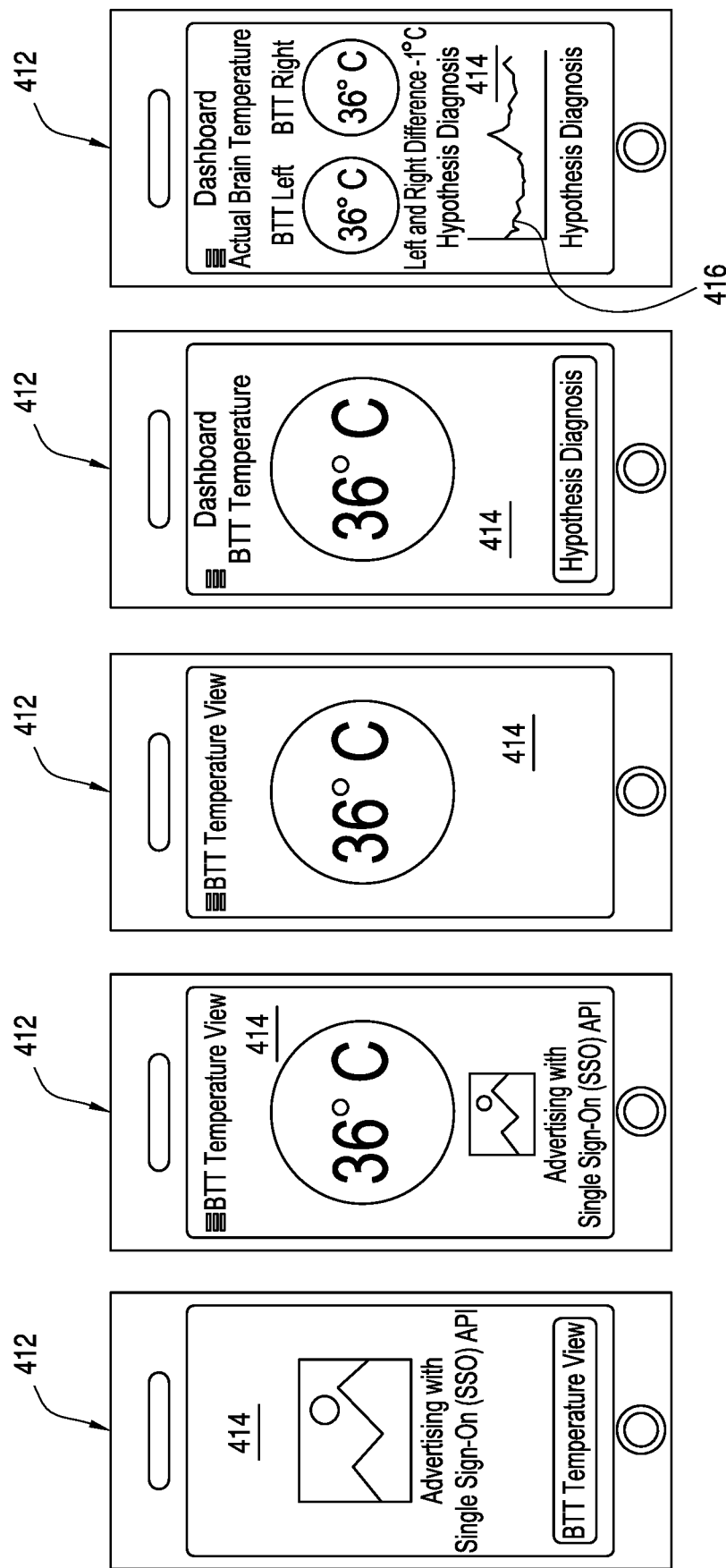

DEVICE FOR MEASURING THE INFRARED OUTPUT OF THE ABREU BRAIN THERMAL TUNNEL

CROSS-REFERENCE TO RELATED APPLICATIONS

This application is a continuation of U.S. patent application Ser. No. 16/542,394, filed Aug. 16, 2019, which is a continuation of Ser. No. 15/972,605, filed May 7, 2018, which is a divisional of U.S. patent application Ser. No. 14/593,848, filed Jan. 9, 2015, which claims the benefit of priority to U.S. Provisional Patent Application No. 61/926,155, filed Jan. 10, 2014, which are hereby incorporated by reference in their entirety.

TECHNICAL FIELD

This disclosure relates to a medical device for monitoring biological parameters.

BACKGROUND

Diagnostics for measuring and monitoring an array of biological parameters exist. Among the many biological parameters that can be measured are pulse, blood pressure, heart function (EKG), brain function (EEG), temperature, etc.

SUMMARY

This disclosure provides a sensing device configured to interface with a human Abreu brain thermal tunnel (ABTT) terminus. The sensing device comprises a body portion, a handle portion, a viewing portion, and a sensing portion. The body portion includes a first end and a second end. The handle portion is positioned on the second end of the body portion. The viewing portion is positioned on the body portion, and the viewing portion includes a display. The sensing portion includes a sensor positioned on the first end of the body portion, and the sensing portion includes a free end. The free end is configured to receive a signal from the ABTT terminus, and having a field of view to capture at least the signal from a center portion of the ABTT terminus.

This disclosure also provides a sensing device configured to interface with a human Abreu brain thermal tunnel (ABTT) terminus. The sensing device comprises a body portion, a handle portion, a viewing portion, and a sensing portion. The body portion includes a first end and a second end. The handle portion is positioned on the second end of the body portion. The viewing portion is positioned on the body portion, and the viewing portion includes a display. The sensing portion includes an infrared sensor positioned on the first end of the body portion. The sensing portion includes a free end and is configured to allow positioning of the free end to receive infrared energy from the ABTT terminus, and includes a field of view to capture at least the infrared energy from a center portion of the ABTT terminus.

This disclosure also provides a sensing device configured to interface with a human Abreu brain thermal tunnel (ABTT) terminus. The sensing device comprises a body portion, a handle portion, a sensing portion, and a display. The body portion includes a first end and a second end. The handle portion is positioned on the second end of the body portion. The sensing portion includes an infrared sensor positioned on the first end of the body portion. The sensing portion includes a free end and is configured to allow positioning of the free end to receive infrared energy from the ABTT terminus, and includes a field of view to capture at least the infrared energy from a center portion of the ABTT terminus. The display is positioned on a separate electronic device configured to display data related to the infrared energy captured by the infrared sensor. The display is configured to present an advertisement while the infrared sensor receives infrared energy.

Advantages and features of the embodiments of this disclosure will become more apparent from the following detailed description of exemplary embodiments when viewed in conjunction with the accompanying drawings.

BRIEF DESCRIPTION OF THE DRAWINGS

FIG. 3 is an end view of the sensing device of FIG. 1, with the handle portion in a third position.

FIG. 4 is an end view similar to FIG. 3, with the handle portion in the first position of FIG. 1.

FIG. 5 is an end view of the sensing device of FIG. 3, shown from an end of the sensing device opposite the end shown in FIG. 3.

FIG. 6 is an end view of the sensing device of FIG. 4, shown from an end of the sensing device opposite the end shown in FIG. 4.

FIG. 7 is a top view of the sensing device of FIG. 2.

FIG. 8 is a top view of the sensing device of FIG. 1.

FIG. 9 is a bottom view of the sensing device of FIG. 1.

FIG. 10 is a top view of the sensing device of FIGS. 3 and 5.

FIG. 16 is a top view of the sensing device of FIG. 13, without a nose interface portion.

FIG. 17 is a bottom view of the sensing device of FIG. 13, without the nose interface portion.

FIG. 30 is a bottom view of a sensing device in accordance with an exemplary embodiment of the present disclosure.

FIG. 31 is a top view of the sensing device of FIG. 30.

FIG. 32 is a side view of the sensing device of FIG. 30.

FIG. 33 is a front view of the sensing device of FIG. 30.

FIG. 34 is a back view of the sensing device of FIG. 30.

FIG. 35 is a bottom view of a sensing device in accordance with an exemplary embodiment of the present disclosure.

FIG. 36 is a top view of the sensing device of FIG. 35.

FIG. 37 is a side view of the sensing device of FIG. 35.

FIG. 38 is a front view of the sensing device of FIG. 35.

FIG. 39 is a back view of the sensing device of FIG. 35.

FIG. 49 is a side view of a transport container in accordance with an exemplary embodiment of the present disclosure.

FIG. 50 is a side view of the transport container of FIG. 49 in an open position.

FIG. 51 is a side view of the transport container of FIG. 49 with a lid portion supporting the transport container.

FIG. 60 is a simplified view of the ABTT and facial veins associated with the ABTT.

FIG. 61 is a simplified partial cross-sectional view through a human skull in a vertical direction, showing the Abreu brain thermal tunnel and certain other facial features.

FIG. 63G shows another exemplary area to be scanned to locate the ABTT terminus.

FIG. 63H shows an exemplary scanning area for an animal in accordance with an exemplary embodiment of the present disclosure.

FIG. 66A is a view of an infrared sensor or detector array in accordance with an exemplary embodiment of the present disclosure.

FIG. 66B is a stylized output of the infrared sensor array of FIG. 66A.

FIG. 67 is a view of an extension positioned on a sensing portion in accordance with an exemplary embodiment of the present disclosure.

FIG. 68 is a view of the extension and sensing portion of FIG. 67 along the line 68-68.

FIG. 71 is a view of a display of an electronic device in accordance with an exemplary embodiment of the present disclosure.

FIG. 72 is another view of the display of FIG. 71, showing the result of a measurement.

FIG. 73 is a view of the display of FIG. 71, in accordance with another exemplary embodiment of the present disclosure.

FIG. 74 is a view of the display of FIG. 71, in accordance with yet another exemplary embodiment of the present disclosure.

FIG. 75 is a view of the display of FIG. 71, in accordance with a further exemplary embodiment of the present disclosure.

DETAILED DESCRIPTION

Figure 1:
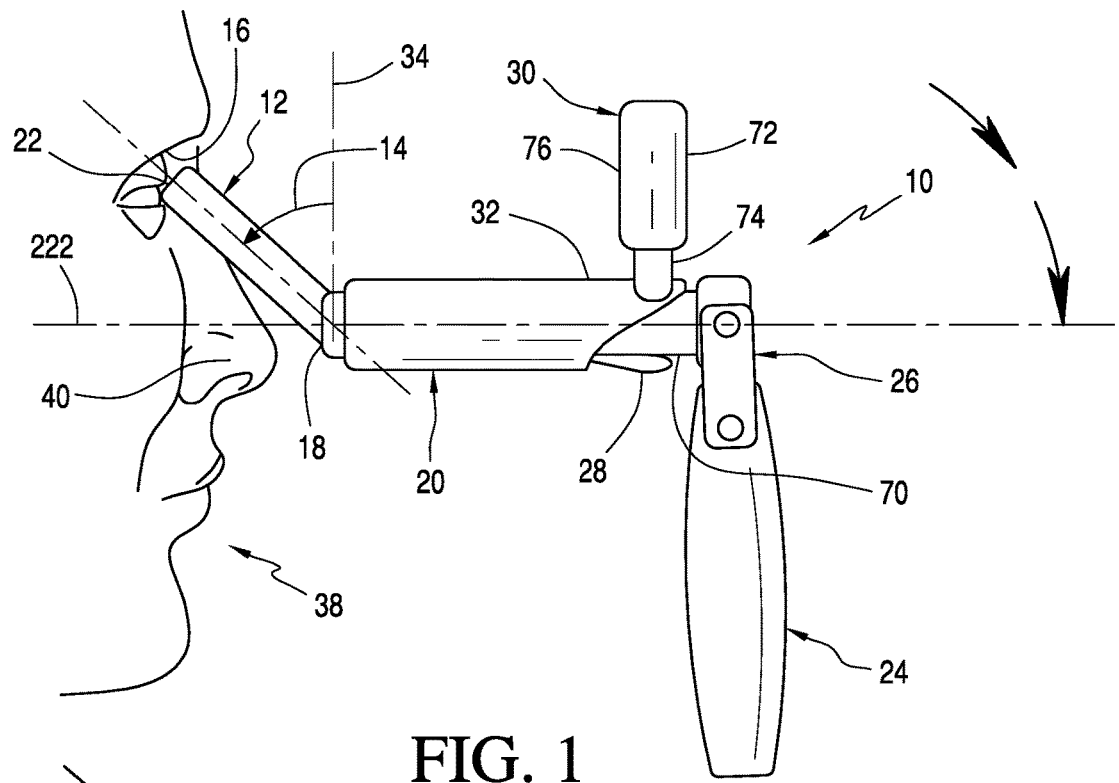
FIG. 1 is a side view of a sensing device in accordance with an exemplary embodiment of the present disclosure, with a handle portion in a first position.

The most precise, accurate, and clinically useful way of evaluating thermal status of the body in humans and animals is by measuring brain temperature. Brain temperature measurement is the key and universal indicator of both disease and health equally, and is the only vital sign that cannot be artificially changed by emotional states. All the other measurable vital signs (e.g., heart rate, blood pressure, and respiratory rate) can be influenced and artificially changed by emotional states or voluntary effort. Currently, brain temperature is difficult to measure. However, the present disclosure describes a device that readily locates the Abreu brain thermal tunnel, described further hereinbelow, and is configured to provide a contact or non-contact temperature reading of the brain. Embodiments of the disclosed device enable an individual to measure their own temperature and enable medical professionals to measure the temperature of others.

Body temperature is determined by the temperature of blood, which emits heat as infrared radiation. Adipose tissue (i.e., fat tissue) absorbs infrared energy, and the body is virtually completely protected with a layer of adipose tissue adherent to the skin. Thus, conventional measurement of temperature on the skin has traditionally been imprecise and inaccurate because previous techniques used sensors placed on skin characterized by the presence of adipose tissue. For example, temperature sensors have conventionally been placed under the tongue, on the forehead, in the armpit, and rectally. Because of the presence of fat, distance from flowing blood, or both, temperature measurements in surface locations typically require adjustment to compensate for the lower temperature level assumed to be in these locations as compared to core body temperature.

In addition to inaccuracy and imprecision, because conventional temperature measurements are contact measurements, such contact risks the transmission of communicable diseases. A non-contact device for the measurement of body core temperature would lower the likelihood of transmission of certain transmittable viruses and other illnesses, such as SARS, influenza and the like. A non-contact device configured to be positioned to read the infrared output of the Abreu brain thermal tunnel (ABTT), whether by an individual for self-measurement or by a medical professional, and configured to properly detect thermal disturbances such as hypothermia and heat exhaustion, would provide a simple, accurate and non-invasive device or apparatus for measuring brain temperature. Such capability is valuable in a clinical environment, such as doctor's offices, which may see many patients during the course of a day, typically requiring sanitary covers and/or sterilization of conventional thermometers. However, simple, accurate, and timely temperature evaluation is also valuable at home, so that urgent cases may be easily more readily diagnosed, such that the necessity of making doctor visits may at times be alleviated. Although many of the exemplary embodiments disclose a non-contact device, it should be understood that embodiments described herein can be used with a contact sensor or detector, such as those shown in exemplary embodiments.

Sensing and reporting systems have been disclosed which may be used individually or in combination, which are designed to access a physiologic tunnel to measure biological, physical, and chemical parameters of a human or an animal. Such systems have been described in U.S. Pat. Nos. 7,187,960, 8,172,459, 8,328,420, 8,721,562, 8,834,020, and 8,849,379, which are incorporated herein by reference in their entirety. Anatomically and physiologically speaking, the Abreu Brain Thermal Tunnel (herein referred to as ABTT), previously described by Applicant as the brain temperature tunnel, is an anatomic path that conveys undisturbed physiologic signals to the exterior of the body. The ABTT includes a direct and undisturbed connection between the source of the function (signal) within the body, which is the hypothalamus region of the brain, and an external point on the skin on, over, or adjacent to an end of the tunnel, which may be described as the ABTT terminus. This physiologic tunnel conveys continuous and integral data on the physiology of the body. As shown by Applicant, the ABTT has a unique configuration that includes high and low thermal conductivity areas, with the skin surface being free of fat (high thermal conductivity) and the internal portion of the ABTT surrounded by fat (low thermal conductivity). An undisturbed signal from within the body is delivered to the external point on the skin over, on, or adjacent to the end of the ABTT. A sensor or detector located at on the skin at the end of the tunnel allows optimal signal acquisition from the brain without interfering constituents and sources of error. In an exemplary embodiment, such signals are infrared signals, and the sensor or detector is an infrared sensor or detector. In another exemplary embodiment, the signals can be radio frequency signals, and the sensor or detector is a radio frequency receiver. In yet another embodiment, the signals are sound signals that may be in a frequency range above and below the typical range of human hearing, and the sensor or detector is a sound sensor or detector with the ability to receive the appropriate frequency range. In a further embodiment, the signals are magnetic or electromagnetic, and the sensors or detectors are magnetometers or other sensors configured to read magnetic energy. It should thus be understood that a plurality of energy forms, e.g., magnetic, sonic, optical, and radio energies, can be detected from the ABTT terminus.

It should also be understood that temperature at the ABTT terminus may also correspond to the core temperature or internal body temperature, which can occur, for example, when a person is at rest in a typical indoor environment, or skin temperature, which can occur, for example, in an environment where the temperature is above 99 degree F., depending on humidity, wind conditions, etc. Generally, core temperature and internal body temperature are synonymous when discussing such temperatures as being the internal temperature of the trunk of the body. Hence, for the purpose of description herein "brain temperature" is used for any temperature measured at the ABTT site.

A set of support structures designed to be attached to the body of a user to measure temperature through contact with the skin of the ABTT target area have been previously discussed and disclosed in one or more of the patents previously referenced. While such structures provide many benefits, an easy to use apparatus configured to measure brain temperature non-invasively without requiring contact to the skin provides benefits, potentially including increased accuracy, reduced chance of transmitting communicable diseases, and increased speed of measurement.

An apparatus configured with an infrared sensor and configured with an appropriate field of view for measuring the temperature of the ABTT target area, without including measurement or estimation of values of the surrounding areas, would also provide benefits to diagnosis and measurement of ABTT temperature. It should be understood, however, that comparative measurements or estimation of the surrounding area with respect to the ABTT terminus are within the scope of the invention. In an exemplary embodiment, an area surrounding the ABTT terminus of 10 centimeters in diameter of a circle truncated at or on the eyebrow may be measured for comparison to the ABTT terminus. In another exemplary embodiment, an area surrounding the ABTT terminus of 8 centimeters in diameter of a circle truncated at or on the eyebrow may be measured for comparison to the ABTT terminus. In yet another exemplary embodiment, an area surrounding the ABTT terminus of 6 centimeters in diameter of a circle truncated at or on the eyebrow may be measured for comparison to the ABTT terminus. In yet a further exemplary embodiment, an area surrounding the ABTT terminus of 3 centimeters in diameter of a circle truncated at or on the eyebrow may be measured for comparison to the ABTT terminus. It should be understood that the larger the area taken for comparison, the greater the processing time needed for analysis, and the longer it will take to receive results. Generally, these areas are centered on the ABTT terminus, which, as described herein, is approximately located in the mid-portion between the eyebrow and the eye, adjacent to the nose. In an exemplary embodiment, processing circuitry is adapted or configured to subtract or remove the surrounding areas around the ABTT terminus from the calculation of temperature. It should be noted that skin areas surrounding the ABTT terminus are typically at a lower temperature than the ABTT terminus. However, conditions can exist where the ABTT terminus is at a lower, cooler, or colder temperature than the ABTT terminus. In an exemplary embodiment, the apparatus is configured with a field of view for viewing an area on the surface of the skin on, over, or adjacent to the ABTT corresponding to the main entry point of the ABTT, which is an area with higher thermal emission compared to surrounding areas. In an exemplary embodiment, this area includes a diameter of 9 mm or less, more preferably an area with a diameter of 6 mm or less, and even more preferably an area with a diameter of 3 mm or less, and most preferably an area with a diameter of 2 mm or less, all of which are centered on the ABTT terminus. It should be understood that the ABTT area includes preferably the upper eyelid area and the area between the eye and the eyebrow. It should further be understood that the region or area used for comparison to the ABTT target area or terminus also includes the area of the caruncle and corner of the eye surface as the area measured by many embodiments of the present disclosure.

In an alternative embodiment, the field of view is larger than the ABTT terminus. In an exemplary embodiment, the apparatus is configured with a field of view for viewing an area on the surface of the skin on, over, or adjacent to the ABTT terminus corresponding preferably to an area with a diameter of 20 mm or less, more preferably to an area with a diameter of 15 mm or less, yet more preferably to an area with a diameter of 10 mm or less, and most preferably to an area with a diameter of 7 mm or less. In this embodiment, the apparatus is configured to resolve or locate the peak temperature of the ABTT region, which is representative of brain temperature. To resolve or locate the peak temperature, the apparatus may be configured with a controller or processor to analyze the input from an infrared sensor or any non-contact temperature sensor or detector. It should also be understood that a contact thermal sensor can be used and is within the scope of the invention. As described further herein, the controller may analyze the infrared (IR) intensity of individual pixels in the IR sensor and correlate the intensity to temperature. Alternatively, cumulative readings of the entire ABTT area may be acquired, and the resultant data may be mathematically adjusted by the controller to eliminate the regions outside the ABTT. Although some estimation may be required to calculate the temperature of the ABTT, as there may be anatomic differences among different people, the view of the hottest area can be calculated, despite using a view for seeing a spot or area larger than 3 mm.

In an exemplary embodiment, the wave guide of the infrared detector has a field of view for viewing an area of, by way of illustration, measuring 5 mm. This area includes the main entry/exit point of the ABTT terminus, which is typically the highest or hottest temperature, in addition to surrounding areas of a different, typically lower, temperature. The processor calculates the temperature of an annulus having a width of about 1 mm surrounding the ABTT and uses that number to determine the temperature of the hottest area. For example, if the 3 mm ABTT area has a temperature of 37 degrees C., and the surrounding area has a temperature of 36 degrees, then by viewing a 5 mm diameter an average temperature may be 36.5 degrees C., meaning approximately 0.5 degrees C. below the peak temperature of the ABTT area. The controller or processor then adds 0.5 degrees C. to achieve the temperature of the hot area (37 degrees C.).

In another exemplary embodiment, the apparatus is configured to include a field of view of 7 mm in diameter. The controller or processor then calculates the temperature of the area around the ABTT terminus, which may be an annulus that is 2 mm wide about the ABTT terminus, and the temperature difference of the area away from the ABTT terminus is added to the overall numerical value measured. As an example, an ABTT terminus of 3 mm in diameter measures 36.5 degrees C., and an apparatus with a 7 mm field of view measures the entire area at 35.6 degrees C. A temperature difference of approximately 0.9 degrees C. occurs because of the colder area surrounding the ABTT. In a manner of speaking, the ABTT is like an island of fire surrounded by a lake of cold water in which it becomes colder with distance from the ABTT "island." Thus, the controller or processor estimates that the surrounding 2 mm wide ring or annulus area of the ABTT causes about a 1 degree loss (predetermined loss used by the controller or processor to calculate the temperature of the ABTT terminus), and then the controller adds the 1 degree to the measurement obtained with a 7 mm spot or diameter field of view. Thus, in the present example, with a field of view of 7 mm and a measured average temperature of 35.6 degrees C. over the entire field of view, by adding 1 degree C. the final result is 36.6 degrees, which is very close to the true measurement of 36.5 degrees. A similar technique can be applied to any size area by increasing the numerical value of the added factor. It should be understood that this methodology and device or apparatus can include an array of infrared sensors, thermopiles, and the like in a variety of configurations, including but not limited to, preferably a 3×3 sensor array, a 4×4 sensor array, and a 5×5 sensor array. However, depending on the size of the sensor, a range between a 6×6 array to a 20×20 array can be used and it is within the scope of the invention. It should be further understood that the array may not be symmetrical, including one sensor in the center surrounded by, as way of illustration, two to twenty sensors, and preferably surrounded by four or less sensors, most preferably eight or less sensors, and yet most preferably by twelve or less sensors. It should also be understood that the centrally located sensors can include more than one sensor, including, but not limited to, three centrally located sensors surrounded by other sensors. Processing for such an array or multiple sensors occurs in a similar fashion as described for identifying the temperature at the main entry point, and further includes the highest temperature and surrounding temperature. As disclosed, in certain situations, the highest temperature is not the main entry point of the ABTT (equivalent to brain temperature), and in this instance the lower temperature is the chosen temperature as the brain temperature, or the target temperature. It should also be understood that this methodology and device or apparatus can be used in other fields in which viewing the exact target is not possible and there is viewing of surrounding areas, or in which there is an undefined target area surrounded by areas of different temperature in the body.

In yet another exemplary embodiment, a thermal imaging camera views more than the ABTT terminus area, and by knowing the actual temperature of the surrounding areas, a controller of the thermal imaging camera can calculate the exact peak temperature level of the ABTT terminus. The controller uses the temperature of the area surrounding the ABTT terminus, which is represented by a temperature adjustment or compensation factor F. Temperature factor F is added to the measured temperature value in case the area surrounding the ABTT terminus is colder, or, alternatively temperature factor F is subtracted from the measured temperature value in the case the area surrounding the ABTT terminus is hotter than the main area. In a typical situation where the skin on, over, or adjacent to the ABTT terminus is hotter or warmer than skin surrounding ABTT terminus, temperature factor F increases with distance from the edge of the ABTT, or increases as a diameter of detector spot size increases; i.e., temperature adjustment or compensation increases with a detector field of view. In an exemplary embodiment, the apparatus includes a controller or processor adapted or configured to analyze the IR image or data and determine a temperature of the ABTT terminus, as well as including a non-transitory memory to store the values used in the calculation by the processor as well as the results of the calculation.

In a further exemplary embodiment, the present disclosure includes a hand-held apparatus for measuring brain temperature by way of the ABTT terminus, which serves as a useful tool in a variety of settings, from doctors' offices to personal homes. In an exemplary embodiment, the tool is configured to remove a degree of a "fright factor" that can accompany measurements taken at the ABTT target area, i.e., the ABTT terminus, and any apparatus being placed near the eyes of the person whose measurements are being taken. In an exemplary embodiment, the apparatus or device is configured to provide convenience in storing, carrying, and operation.

The presently disclosed embodiments are exemplary, and a person of ordinary skill will understand that certain changes and modifications of the present embodiments are inherent in the scope of the present disclosure.

The present disclosure describes embodiments of an apparatus for measuring temperature at the ABTT terminus or target region that is non-invasive and does not require contact of the sensor with the skin of a subject or patient. Alternatively, the tip of a probe or a wave guide may rest on the skin of a patient or subject at a physiologic tunnel, such as the ABTT terminus site positioned at a location that is in a region between the eye and the eyebrow.

The present disclosure includes an apparatus for collecting thermal radiation from an ABTT terminus, which may convert said thermal radiation, i.e., the intensity of the thermal radiation, into a brain temperature or core temperature, or the temperature of the skin itself. Such conversion is possible because the emissivity of human skin is known, and the IR sensor measures intensity. From these two values, temperature can be determined.

The present disclosure also provides methods for determining body temperature with such methods including steps of collecting thermal emission from the ABTT terminus, producing a signal corresponding to the thermal emission (i.e., intensity) collected, processing the signal (i.e., calculating the temperature), and reporting the temperature. It should be understood that a further step of adjusting the temperature according to the temperature of the surrounding area of the ABTT can be included, and is within the scope of the invention. It should also be understood that other biological parameters can be measured in a similar fashion, including chemical compounds such as glucose, cholesterol, alcohol, any analytes present in the body, any chemicals received by the body, any element produced by the body, such as antibodies, and any microorganisms present in the body. In embodiments where other biological parameters are identified, the radiation signature or the thermal signature of the element as received from the ABTT terminus is used to identify its presence or its concentration.

In a further exemplary embodiment, the value of the signal measured at the ABTT terminus is added to a Brain temperature Factor "BF" to determine the exact brain temperature. In this exemplary embodiment, factor BF can be calculated empirically by measuring the actual brain temperature and identifying the difference between temperature measured at the skin, and temperature measured inside the brain. The BF factor is then used to provide the actual brain temperature when measuring temperature at the ABTT terminus or ABTT skin site. The controller or processor uses the BF factor value stored in the memory, and then adjusts the value calculated by the apparatus to a value corresponding to the brain temperature. The method and apparatus includes a controller or processor and non-volatile memory that uses the values obtained at the ABTT skin terminus site to calculate the actual brain temperature based on the brain temperature values, i.e., the BF factor, measured experimentally. The BF factor calculated from brain parenchyma temperature provided the range of adjustment for determining brain temperature from the ABTT terminus on the eyelid skin. By way of example, but not of limitation, a preferred BF factor is equal to or less than 1.7 degrees C., more preferably the BF factor is equal to or less than 1.0 degrees C., even more preferably the BF factor is equal to or less than 0.5 degrees C., and yet most preferably the BF factor is equal to or less than 0.3 degrees C. The empirical or experimental measurements of brain temperature as well as the temperature at the ABTT terminus can be acquired by an apparatus or device described herein configured to measure temperature in the range of the ABTT terminus, including contact sensors, non-contact sensors (including infrared), and thermal imaging.

It should be understood that while the foregoing discussion describes adjustment or compensation factor BF, such factor is typically a relatively small value in humans given that the ABTT terminus is directly linked to the brain core in the region of the hypothalamus, but in certain situations of extreme hot or cold, the BF factor can be of larger magnitude. Furthermore, empirical measurements indicate that measurements of temperature at the ABTT terminus are the most accurate type of temperature measurements of the human body, with variation from actual core temperatures equal to or less than 0.2 degrees C. Accordingly, the BF factor, while useful in providing very precise and accurate temperatures of the brain, is generally not a significant adjustment for humans. Furthermore, it should also be understood that the inherent configuration of the ABTT terminus is such that the BF factor value is, for most practical purposes, identical between human individuals. Thus, the same BF factor value can be used for compensation of temperature measurements for all people.

Additionally, while having a very precise and accurate measurement of brain temperature may be valuable in some circumstances, one of the most valuable benefits of measuring temperature at the ABTT terminus is the variation in relative temperature with time. Thus, having precise temperatures is often less important than analyzing temperature variation with time. Thus, the BF factor value in humans is more for the few situations where accuracy and precision are necessary.

While the BF factor value may be relatively unimportant for humans, animals do not have an ABTT terminus positioned on the skin and animals may have fur which reduces thermal conductivity, shifting the position of the equivalent of ABTT terminus in animals to an area of transition skin-mucosa located in the corner of the eye, frequently adjacent to the tear duct and caruncle or conjunctival surface (referred to herein as Transition Area). In some species, such as canines, felines and other predators, the equivalent of the ABTT terminus is located in the anterior (or medial) portion of the corner of the eye, in swine tend to be located in the posterior (lateral) corner of the eye, ovine tend to be located in the anterior corner of the eye, and primates such as chimpanzees tend to be located in both the medial corner and the lateral corner of the eye. The location in animals does provide a difference in temperature that benefits from the BF factor value, which ideally should be determined for each species of interest. The BF factor calculated from brain parenchyma temperature in canines provided an exemplary range of adjustment for determining brain temperature from the transition area. By way of example, but not of limitation, an exemplary BF factor for canines is equal to or less than 2.6 degrees C., more preferably the BF factor for canines is equal to or less than 1.6 degrees C., even more preferably, the BF factor for canines is equal to or less than 1.0 degrees C., and most preferably, the BF factor for canines is equal to or less than 0.5 degrees C.

In an exemplary embodiment, the components of the apparatus include a sensing portion for evaluating biological parameters, for example, the body temperature of a person using infrared wavelength sensors. This sensing portion can be hand held or fastened to a body portion so that it is at an optimal angle to access the Abreu brain thermal tunnel terminus or target area, or transition area in animals. This optimal angle is approximately perpendicular to the ABTT terminus, though variations of angle up to 30 degrees from perpendicular yield useful and relatively accurate measurements. Another preferred exemplary angle may include a 30 to 45 degree angle in which the sensor is viewing the ABTT terminus from below and in a diagonal position. The apparatus also includes an adjustable handle portion connected to the body portion of the device using a hinge or other adjustable connection apparatus, which allows a user to manipulate the apparatus for an optimal holding position for comfort during use. The apparatus includes a switch for operation. The apparatus may also include a viewing or display portion (e.g., slide screen, an electronic digital viewer, or any suitable display capable of displaying images and/or alphanumerical characters), which is mounted on an upper side of the main body portion so that the display is preferably located directly in the line of sight of the person whose measurements are being taken. In one exemplary embodiment, the viewer has a double sided display allowing viewing the display from the front or back, thus allowing a subject being measured to view the display and also an operator (e.g., a doctor, scientist, other medical practitioner, etc.) also to view the display. Another aspect of the invention as disclosed herein presents a box to enable safe storage, transportation, and use of the apparatus. In one exemplary embodiment, the apparatus includes a photo or video camera, preferably facing the ABTT.

Figure 62:
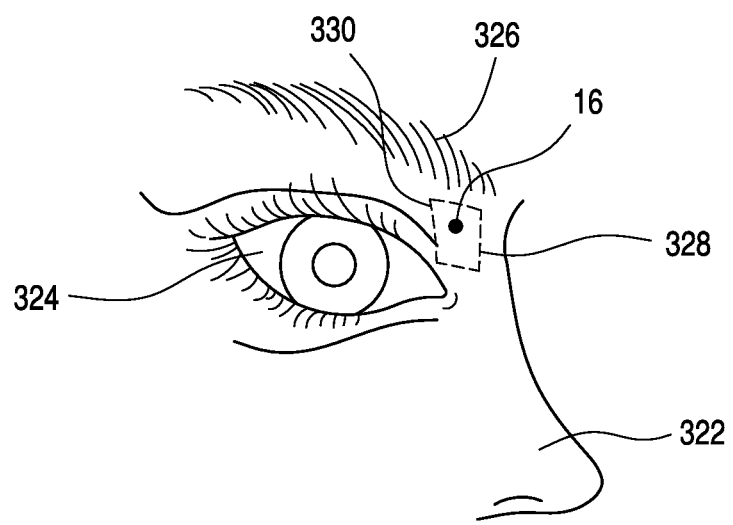
FIG. 62 is a view of a face showing an ABTT terminus in an ABTT scan area.

Dissection of cadavers was undertaken as a part of understanding the unique characteristics of the ABTT. Cadaver dissection delineated anatomy, which may be seen in FIGS. 60, 61, and 62, showing the convergence of four veins at ABTT target area or terminus 16; frontal 80, superior palpebral 82, supraorbital 84, and angular 86. This area is unique, and is the only such area in the head, in which a vein, ABTT 88, courses transversally with respect to the longitudinal extent of the human body into the center of the brain, with the opposite end terminating on the skin.

Additionally, ABTT target area 16 is extremely vascularized and is the only skin area in which a direct branch of the cerebral vasculature is located and covered by a thin skin without a fat layer. The main trunk of the terminal branch of the ophthalmic vein is located right at ABTT target area 16, just above the medial canthal tendon supplied by the medial palpebral artery and medial orbital vein. ABTT target area or terminus 16 on the skin, supplied by a terminal and superficial blood vessel ending in a particular area without fat and void of thermoregulatory arteriovenous shunts, provides a superficial source of undisturbed biological signals including brain temperature, metabolic function, physical signals, and body chemistry such as glucose level, and the like.

Briefly, the blood from veins under the surface of a face 90 flows into ABTT 88. Having converged at ABTT terminus 16, the blood from these veins 80, 82, 84, and 86 flows into the brain from ABTT terminus 16, into ABTT 88, and then into the center of the brain, at the cavernous sinus (not shown), which Applicant identified as a thermal storage area, and which is adjacent to the thermoregulatory center of the brain. From the thermal storage area, thermal energy in the form of hot or cold blood is distributed throughout tissues of the brain. It was also recognized by the Applicant that ABTT 88 includes bidirectional blood flow, from the brain to ABTT terminus 16 and from ABTT terminus 16 to the brain. Applicant recognized that the flow of blood through ABTT 88 represented a unique diagnostic to determine the condition of the brain and the body by measuring the thermal condition of ABTT terminus 16. As seen in the histology of ABTT terminus 16, as shown by Applicant in an unpublished co-pending application, the skin at ABTT terminus 16 is void of fat, thereby allowing thermal energy transmission from ABTT 88 through the skin at ABTT terminus 16, where the thermal energy may be measured and analyzed to provide information regarding the condition of the brain and the body.

The approximate locations of the veins 80, 82, 84, and 86 are shown in FIGS. 60 and 61 with respect to other facial features. Angular/facial vein 86 runs up alongside nose 92, superior palpebral vein 82 runs along eyebrow 94, and frontal vein 80 and supraorbital vein 84 run under forehead 96. It should be understood that arterial blood also runs in parallel in some areas, but said arterial blood does not go toward the center of the brain as the venous blood does.

Anatomically and physiologically speaking, the Abreu Brain Thermal Tunnel (ABTT) 88 includes a continuous, direct, and undisturbed connection between a thermal signal source within the brain and an external point on the skin at the end or terminus of the tunnel. Thus, the skin on, over, or adjacent to the end of ABTT 88 may be considered the ABTT terminus given the proximity of the skin to the end of the tunnel, and the lack of adipose tissue between the end of the tunnel and the interior surface of the skin. In the absence of insulating fat, skin is a good conductor, and thus the temperature of the skin over the end of ABTT 88 is nearly the temperature of ABTT 88 itself. Accordingly, the physical and physiological events at one end of the tunnel, inside the brain, are reproduced at the opposite end on the skin. ABTT 88 enables direct thermal signal transfer through the tunnel without interference by heat absorbing elements; i.e., elements that can absorb thermal energy transmitted by blood within the brain. The end of ABTT 88, herein referred to as the "terminus" or "target area" on the skin, is located in a region between the eye and the eyebrow that measures about 14 mm in diameter measured from the medial corer of the eye at the canthal tendon and extends superiorly for about 12 mm, and then extends into the upper eyelid in a horn-like projection for another 22 mm. The lower portion of the ABTT terminus is adjacent to the punctual area (or tear duct), which can serve as a measurement area and/or a reference for placement of an ABTT support structure.

The ABTT terminus is located in a crowded anatomic area. Thus, positioning of a sensor or detector to measure a signal from the ABTT terminus requires appropriate geometry for optimal alignment with the end or terminus of the tunnel. The clinical usefulness of the tunnel can only be achieved with the proper positioning of a sensor in relation to anatomic landmarks and a support structure for the sensor. The tunnel is located in a unique position on the human body, with distinctive anatomic landmarks that help define the external geometry and location of the end of the tunnel. The main entry point of the tunnel is the preferred location for positioning the sensor, which is preferably positioned in a central area of a surface of a support structure and facing the skin. The support structure and supported sensor facing and/or touching the skin at the ABTT terminus includes an exemplary maximum dimension equal to or less than 18 mm, a more preferred exemplary maximum dimension equal to or less than 14 mm, an even more preferred exemplary maximum dimension equal to or less than 10 mm, and a most preferred exemplary maximum dimension equal to or less than 8 mm for optimum signal acquisition. A preferred exemplary embodiment for the measurement of biological parameters by accessing the physiologic tunnel includes sensors positioned in a particular geometric position on or in the support structure including an eccentric position.

In describing exemplary embodiments of the invention, specific terminology will be used for the sake of clarity. However, exemplary embodiments are not intended to be limited to the specific terms selected, and it should be understood that each specific term includes all technical equivalents which operate in a similar manner to accomplish a similar purpose. It should also be understood that each individual part or component and/or each individual embodiment or a combination of said parts or components and any embodiment is within the scope of the invention.

The support structure disclosed herein comprises a handheld device that includes a sensor or detector adapted to receive and measure a signal from the ABTT terminus when the sensor is positioned to view the ABTT "target area," positioned on the ABTT "target area," or positioned adjacent to the ABTT "target area." It should be understood that besides a hand held device, any other configuration is within the scope of the disclosure, including table top, lap top, wall mounted, anchored to the body or head, and the like. The following aspects of the disclosed embodiments are described herein, these aspects being employed either separately or in any combination to comprise a device to measure, continuously or non-continuously, the temperature of the brain or any other biological parameters by contact or non-contact measurement of the skin of the ABTT "target area." A sensing device or apparatus, an exemplary embodiment of which is shown in, for example, FIG. 1, and generally indicated at 10, includes the following features:

A sensing portion 12 fixed at a predetermined angle 14 for capturing a signal by contact or non-contact from ABTT terminus 16, with one end, which is a first end 18, of sensing portion 12 connected to a body portion 20, and a second free end 22 containing the sensor to receive energy from ABTT terminus or target area 16. In an exemplary embodiment, the sensor is an infrared sensor. However, it should be understood that ABTT 88 and ABTT terminus 16 emit a plurality of energies and/or wavelengths. Accordingly, in other exemplary embodiments, the sensor, which in some circumstances may also be described as a detector, may be, for example, a sound or vibration sensor, a magnetometer, an electromagnet sensor, etc., configured to receive the signals transmitted through ABTT 88 and ABTT terminus 16. Accordingly, when a particular type of sensor is described herein, such as an infrared sensor or detector, it should be understood that other types of sensors may be used as well, with any modifications required for the energy or frequency being measured or received. It should be understood that first end 18 may include a rotating mechanism to allow adjusting the angle. An exemplary predetermined angle 14 with respect to a line perpendicular to the ground, with a human patient or subject standing, head held level, is equal to or less than 20 degrees, or more preferably, an exemplary predetermined angle 14 is equal to or less than 45 degrees, or even more preferably, an exemplary predetermined angle 14 is equal to or less than 60 degrees, and most preferably, an exemplary predetermined angle 14 is equal to or less than 75 degrees;

A handle portion 24, which may be adjustable in angle by an adjustable connection mechanism 26 that attaches or connects handle portion 24 to body portion 20, or may be fixed to body portion 20 in a position optimized for holding sensing device 10;

At least one switch 28 for activating the functions of sensing device 10;

Viewing portion 30 (e.g., a slide screen portion, electronic digital display, standard display, projection display, transparent display, and the like) mounted on an upper portion 32 of body portion 20, which provides an output for displaying information to people whose measurements are being taken, in part so that the attention of the subject or patient is diverted away from sensing portion 12; and Body portion 20, which may comprise a printed electric circuit board or any circuitry, including a controller or processor or apparatus for processing, recording, activating, displaying, and transmitting data gathered by the sensor. Switch 28 may be positioned on body portion 20. The at least one switch includes switch 28 or other actuating mechanism for turning the apparatus on and off. Switch 28 may also activate measurements, or a separate switch or other actuating mechanism (not shown) may be provided for activating measurements. An external device such as cell phone, watch, eyeglasses, computer, and the like may also activate the apparatus.

It should be understood that although temperature is the biological parameter used to illustrate the exemplary embodiments of the present disclosure, other biological parameters and analytes can be measured and/or analyzed at any portion of the brain tunnel described in the disclosure, including from the skin surface, the periorbital and intracranial portion, and the opposite end of the brain tunnel, including the hypothalamus, thalamus and other brain tissues as the cerebral cortex. A radiation signature of any chemical compound can be quantified in the thermal emission of ABTT terminus 16, or application of infrared energy to ABTT terminus 16 can generate a reflected infrared signal suitable for determining the concentration of analytes as well as determining the presence of any antigen, antibodies, or other substances, such as chemical compounds (e.g., drugs) present in the body or in the blood.

The disclosed embodiments comprise at least sensing portion 12 that is connected to body portion 20 of apparatus or device 10 according to the aspects of the disclosure. Sensing portion 12 serves as the free end of device 10. Sensing portion 12, to measure the temperature of the brain or other biological parameters using ABTT target area 16 most effectively, should be positioned so that it forms an optimal angle for measuring ABTT terminus area 16. For brain temperature evaluation, tunnel area 16 includes mostly the area between the eye and the eyebrow, including the medial part of the upper eyelid area. Free end 22 of sensing portion 12 is most preferably located at the main entry point 16 of the tunnel, which is located on the skin 2.5 mm medial to the corner of the eye and about 3 mm above the medial corner of the eye. However, it should be understood that this location is approximate, and that the position of ABTT terminus 16 can vary by several millimeters, for example, plus or minus 5 mm, and most frequently plus or minus 3 mm. The diameter of main entry point 16, i.e., ABTT terminus or target area 16, is about 6 to 7 mm with the highest or peak thermal and infrared emission being within a diameter of about 5 mm or less, more likely within a diameter of about 3 mm or less, and most likely within a diameter of about 2 mm or less. It should also be understood that ABTT terminus 16 is not a perfect diameter, and may be somewhat oval, oblong, or irregular. The positioning of sensing portion 12 at main entry point 16 of the Abreu tunnel provides the optimum site for measuring physical and chemical parameters of the body as represented by the output of the tunnel. It should be understood that portion 26 may be fixed at any of the preferred angles described herein.

In order to position sensing portion 12 at the optimum location for measurement, sensing portion 12 as described herein as one of the exemplary embodiments is situated at a particular angle in relation to the ground, which will be illustrated with a subject being in a standing position and the body approximately perpendicular to the ground, as described herein. In this illustration, an exemplary angle 14, which is measured from a line 34 extending perpendicular to the ground and extending parallel to the face, is equal to or less than 60 degrees, and is more preferably equal to or less than 45 degrees, as is shown in, for example, FIGS. 1 and 2. It should be understood than an angle smaller than 45 degrees can be used, and such an angle would provide a beneficial interface angle with respect to the anatomic features of ABTT "target area" 16 since ABTT "target area" 16 tends to face or angle downwardly. It should also be understood that a sensor such as that shown in FIG. 16, also is preferably oriented at an angle 36 to an axis 222 that is perpendicular to vertical axis or line 34. An exemplary angle 36 is equal to or less than 10 degrees, a preferred exemplary angle 36 is equal to or less than 25 degrees, and a more preferred exemplary angle 36 is equal to or less than 55 degrees. An exemplary embodiment comprises sensor portion 12 that views ABTT terminus 16 from the bottom, i.e., sensor portion 12 looks or is angled upwardly, and from the side of a face 38, or angled toward the center of face 38, i.e., toward a nose 40, achieving thus a preferred viewing angle, so for right ABTT 16, the position of detector or sensing portion 12 is for viewing from the bottom and from the right side of face 38 from the perspective of the patient or subject being measured, and for the left ABTT (not shown), the position of detector or sensing portion 12 is for viewing from the bottom and from the left side of the face from the perspective of the patient or subject being measured.

Figure 46:
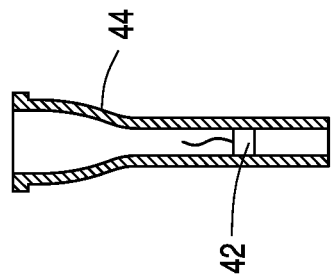
FIG. 46 cross-sectional view of the wave guide of FIG. 45 along the line 46-46.
Figure 47:
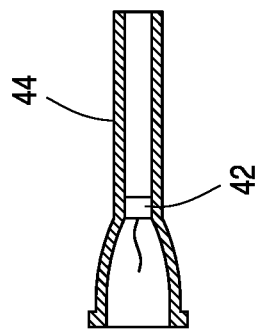
FIG. 47 is a cross-section view similar to FIG. 46, showing the infrared sensor is a position different from FIG. 46.
Figure 45:
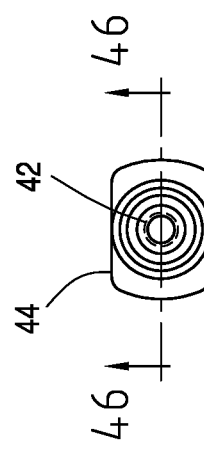
FIG. 45 is an end view of a wave guide in accordance with an exemplary embodiment of the present disclosure.

In an exemplary embodiment, sensing portion 12 includes a non-contact infrared (IR) sensor 42. Exemplary embodiments of IR sensor 42 and associated apparatus and different positions of IR sensor 42 are shown in FIGS. 40-44, as well as an internal end position shown in FIG. 47, a mid position shown in FIG. 46, and external end position (shown in FIG. 44). It should be understood that other sensors may be employed that measure temperature or other biological parameters of ABTT target region 16, including those that require contact with the skin, such as thermistors, and those that do not require skin contact. The IR measurement is based on the Stefan-Boltzmann law of physics in which the total radiation is proportional to the fourth power of the absolute temperature, and the Wien Displacement law in which the product of the peak wavelength and the temperature are constant. The field of view of the non-contact infrared apparatus 10 of the disclosure is adapted to match the size and geometry of ABTT terminus area 16 on the skin, with an exemplary diameter (dimension) of a spot size viewed by infrared sensor 42 being equal to or less than 12 mm, and preferably equal to or less than 7 mm, another exemplary diameter being equal to or less than 5 mm, another exemplary diameter being equal to or less than 3 mm, and yet a further exemplary diameter being equal to or less than 2 mm. In an exemplary embodiment, the field of view of sensor 42 of apparatus 10 is approximately 9 degrees in order to measure a point that is preferably no greater than 3 mm in diameter. Any diameter greater than 3 mm potentially includes skin surrounding ABTT target area 16 that, because the skin surrounding ABTT target area 16 has a different surface temperature than ABTT terminus area 16, would cause temperature measurements to be less accurate, and potentially require additional compensation or correction for increased accuracy.

Sensor portion 12 of apparatus 10 may include a wave guide 44. Wave guide 44 is represented herein by the structure that receives the infrared radiation prior to the IR radiation reaching IR sensor 42. Specialized wave guide 44 of the present disclosure guides IR radiation to reach IR sensor 42 properly, including the size of the area being measured and distance from the area being measured. Specialized wave guide 44 can take any shape or configuration, but in an exemplary embodiment is a cylinder or a barrellike structure configured for optimizing collection of infrared radiation, and for ease of manufacture. FIGS. 45-48 show several views of an illustrative wave guide 44 of the present invention. Exemplary embodiments of specialized wave guide 44 are described hereinbelow.

Figure 40:
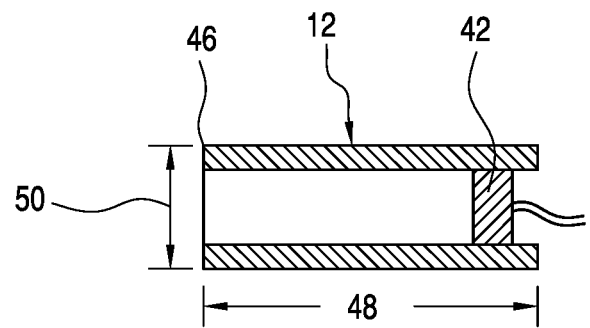
FIG. 40 is a sectional view of a sensing portion along the line 40-40 in FIG. 9 in accordance with an exemplary embodiment of the present disclosure.
Figure 43:
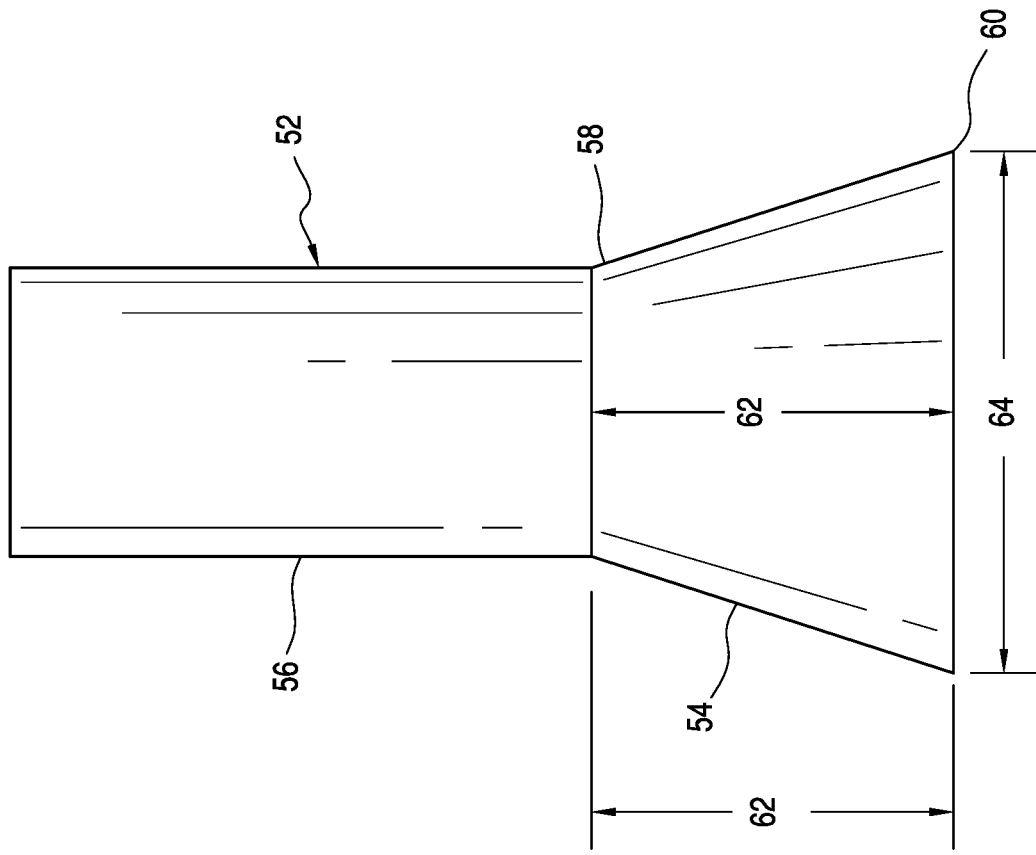
FIG. 43 is a view of a cylindrical structure of a sensing portion in accordance with an exemplary embodiment of the present disclosure.
Figure 48:
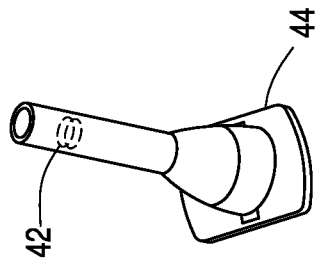
FIG. 48 is a partially sectioned view of a wave guide similar to the wave guide of FIG. 45, showing the infrared sensor in a position different from FIGS. 46 and 47.

The field of view for a conventional IR sensor is approximately 90 degrees. This large field of view is acceptable for measuring body temperature on the forehead or in the ear canal. Such a large field of view is too large to take an accurate reading of the relatively small ABTT target area 16. In order to obtain an IR sensor which has a field of view of the preferred full angle of 15 degrees or less, more preferably 12 degrees or less, and most preferably 9 degrees or less, sensing portion 12 according to one aspect of the disclosed embodiments may comprise IR sensor 42 located at a fixed end of a cylindrical "barrel" structure 46, this barrel structure 46 being well insulated and including, in an exemplary embodiment, a longitudinal length 48 of 70 mm or less, preferably 30 mm or less, more preferably of 15 mm or less, and most preferably of 10 mm or less, as shown in FIG. 40. In particular, an exemplary length 48 of the barrel is equal to or less than 90 mm, a preferred exemplary length 48 is equal to or less than 60 mm, a more preferred exemplary length 48 is equal to or less than 30 mm, an even more preferred exemplary length 48 is equal to or less than 20 mm, and a most preferably exemplary length 48 is equal to or less than 10 mm. An exemplary barrel or cylinder outside diameter 50 is equal to or less than 25 mm, is preferably equal to or less than 15 mm, is more preferably equal to or less than 10 mm, and is most preferably equal to or less than 5 mm. It should also be understood that body portion 20, or any portion of sensing device or apparatus 10 housing electronics and one or more batteries may have any dimensions necessary to house those elements. It should also be understood that an exemplary embodiment wave guide 52, as shown in FIG. 43, can end in a conical structure 54. Wave guide 52 includes a preferably cylindrical structure 56 which terminates as conical structure 54. The dimensions of conical end or structure 54 have to fit with the crowded anatomy of ABTT terminus 16. IR sensor 42 is disposed at first end 18 of sensing portion 12, which may also be described as probe 12. The preferred dimensions of the cone of conical structure 54, i.e., the distance from first cone end 58 of the cone, which may also be described as device end 58, to second cone end 60 resting on the skin or in a non-contact location adjacent to the skin, which may also be described as skin surface end 60, requires specialized dimensions to fit with the anatomy surrounding ABTT terminus 16. An exemplary cone length 62 of the cone is equal to or less than 20 mm, is preferably equal to or less than 15 mm, is more preferably equal to or less than 10 mm, is even more preferably equal to or less than 6 mm, and yet most preferably equal to or less than 3 mm. An exemplary outside diameter 64 of conical structure 54 at second cone end 60 is equal to or less than 25 mm, is preferably equal to or less than 15 mm, is more preferably equal to or less than 11 mm, and is even more preferably equal to or less than 8 mm, and is most preferably equal to or less than 5 mm. In another exemplary embodiment shown in FIG. 44, a conical structure 66 is encased in a cylindrical structure 68. In yet another embodiment, the conical end is replaced by a kidney (or beam) shaped structure (not shown), so as to conform better to the anatomic region between the eye and the eyebrow.

Figure 41:
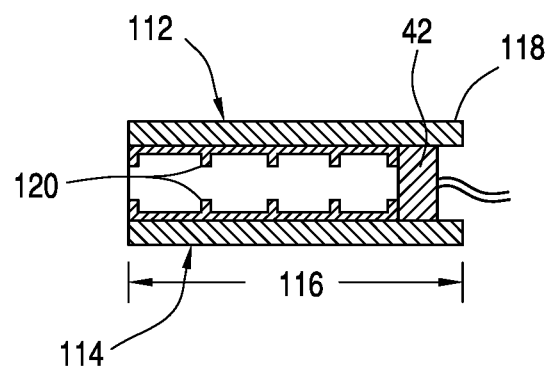
FIG. 41 is a sectional view of another sensing portion similar to the sectional view of FIG. 40 in accordance with an exemplary embodiment of the present disclosure.

In an alternate embodiment, as depicted in FIG. 41, an JR sensing portion 112 may comprise a barrel structure 114 including an exemplary longitudinal length 116 of 10 mm, with IR sensor 42 located near a first end 118, which is similar to first end 18 of the exemplary embodiment shown in FIG. 1, which is at the fixed or attachment end of barrel 114. Barrel 114 includes one or more internal baffles 120 that may be equally spaced and arranged longitudinally therein along the longitudinal length 116 of barrel 114. Baffles 120 may be formed of materials that do not absorb infrared radiation. One benefit of baffles 120 is to provide a field of view that helps to limit data gathering to ABTT terminus 16.

Figure 42:
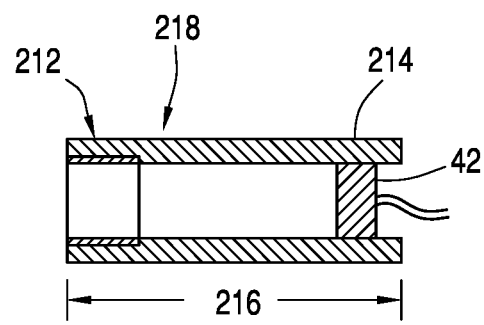
FIG. 42 is a sectional view of another sensing portion similar to the sectional view of FIG. 40 in accordance with an exemplary embodiment of the present disclosure.
Figure 44:
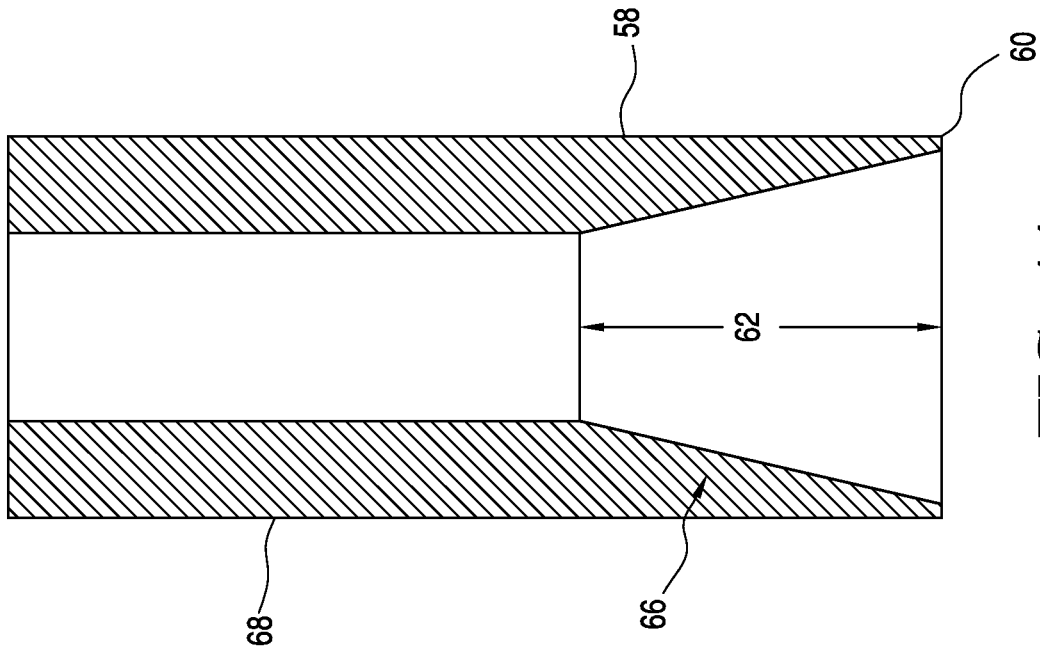
FIG. 44 is a sectional view of a cylindrical structure of a sensing portion in accordance with an exemplary embodiment of the present disclosure.

In another exemplary embodiment, shown in FIG. 42, an IR sensing portion 212 comprises a barrel structure 214, including a longitudinal length 216 of preferably 10 mm with a suitable lens assembly 218 positioned to focus IR light onto IR sensor 42. According to this aspect of the disclosed embodiments, the IR energy emitted by ABTT terminus 16 produces a field of view of 9 degrees, with the area being measured having a diameter of approximately 3 mm. Preferred exemplary longitudinal lengths 116 and 216 of the barrels 114 and 214 are equal to or less than 70 mm, more preferred exemplary longitudinal lengths 116 and 216 are equal to or less than 50 mm, even more preferred exemplary longitudinal lengths 116 and 216 are equal to or less than 30 mm, yet more preferred exemplary longitudinal lengths 116 and 216 are equal to or less than 20 mm, and most preferred exemplary lengths 116 and 216 are equal to or less than 10 mm.

The sensing portions disclosed herein may also comprise one or more wires, cables, and other electric connectors or circuitry adapted to join IR sensor 42 with a suitable supply of power, such as a battery or power source, or to enable signals generated or transmitted by IR sensor 42 to be communicated to a controller, processor, non-transitory memory, PC board, wireless transmitter, or other suitable circuitry or apparatus that may be located in, for example, body portion 20 of sensing device 10, including devices and apparatuses configured to transmit, such as wireless transmitters and/or connection devices and apparatus configured to connect to the internet or a computer network (not shown) via a wireless receiving device including a cell phone, computer, watch, and the like.

This infrared-based system, as provided in the present disclosure, is preferably (but not limited to) being integrated as part of a portable or band-held unit completely disconnected from a human or animal body. It should be understood, however, that the infrared-based system of the present disclosure can be integrated in a support structure in contact with a body, such as, for example, a sticker, bandages, adhesives, medial canthal pad, eyeglasses, goggles, masks, helmets, headbands, head-mounted gear, neck-mounted gear, or other such structures that may be designed to support the ABTT infrared measuring device. Sensing apparatus 10 of the present disclosure may be held by an operator that aims sensing apparatus 10 at ABTT area 16 to perform measurement. Apparatus 10 may also be integrated into a support that is not connected to a body or held by an operator, such as a swing or mount (not shown).

Hand-held sensing device or apparatus 10 should be positioned at a predetermined distance to obtain accurate measurements. To ensure that measurements are being taken at a consistent distance, it is proposed to use optical distance measurement. The optical distance measurement device or apparatus may comprise an alignment mechanism or beam which is connected to viewing portion 30 or other display to inform an operator when the optimal alignment distance has been obtained. It is also understood that optical distance measurement apparatus may be connected to second free end 22. In another exemplary embodiment, the optical distance measurement may comprise an alignment apparatus that is connected to a circuit board or processor (not shown) that will cause the device to automatically take a measurement when the optimal distance has been obtained, thus reducing or eliminating the chance for operator error during measurement using the infrared device. Other distance measurements such as optical by reflectance, ultrasound, lasers, and the like can also be used.

Figure 52:
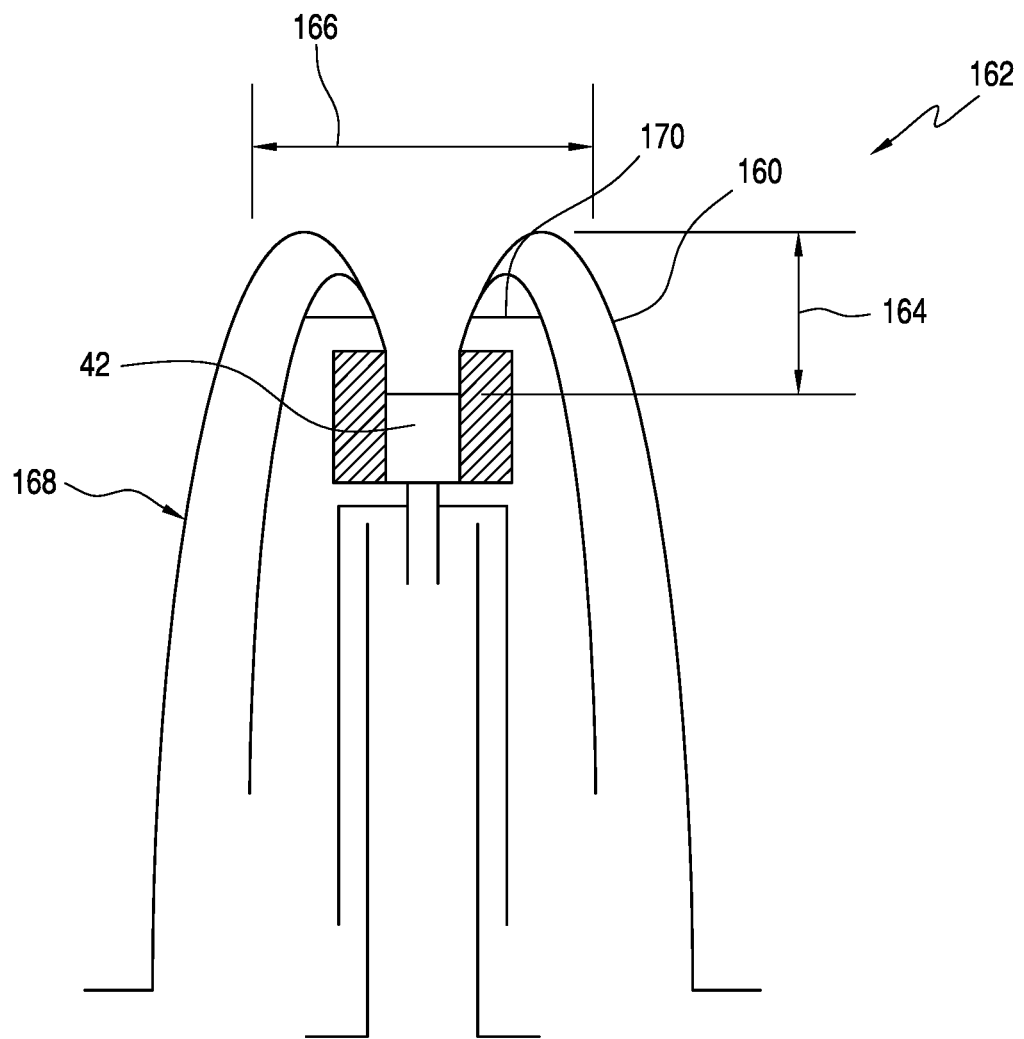
FIG. 52 is a view of a wave guide in accordance with an exemplary embodiment of the present disclosure.

Embodiments of the sensing apparatus as described in this disclosure may further include an extension or tip shaped to be comfortably positioned at ABTT terminus site 16 for measuring temperature and biological parameters without discomfort to the subject or patient. The extension in contact with the skin at ABTT terminus 16 is shaped in accordance with the anatomic landmarks and the geometry and size of ABTT terminus site 16. IR radiation sensor 42 is positioned in the extension, and in an exemplary embodiment, sensor 42 is spaced away from the skin. However, sensor 42 may also rest directly on the skin of ABTT terminus 16. Sensor 42 may also be positioned within the volume of second free end 22, but spaced a distance from the skin of ABTT terminus 16 during measurement. Another exemplary embodiment specialized wave guide for receiving radiation emitted from ABTT site 16 is disclosed FIG. 52 and indicated generally at 162. Wave guide 162 includes IR sensor 42 disposed at a first end 160 of a probe 168, which is the end intended to be positioned on or adjacent the skin of ABTT terminus 16. An exemplary distance 164 of R sensor 42 from the end of probe 162 to the location of IR sensor 42 inside the probe is equal to or less than 30 mm, is preferably equal to or less than 15 mm, is more preferably equal to or less than 10 mm, and is most preferably equal to or less than 5 mm. An exemplary outside diameter 166 of the open end of the probe is equal to or less than 12 mm, is preferably equal to or less than 8 mm, is more preferably equal to or less than 6 mm, and is most preferably equal to or less than 4 mm. An exemplary diameter 168 of the active region of IR sensor 42 is equal to or less than 8 mm, is preferably equal to or less than 5 mm, is more preferably equal to or less than 3 mm, and is most preferably equal to or less than 2 mm. Probe 162 houses IR sensor 42 and associated electrical connections between IR sensor 42 and signal processing circuitry (not shown). First end 160 of probe 162 is preferably an open end to permit IR transmission to IR sensor 42. However, first end 160 may incorporate a window or lens that readily transmits IR energy. It should be understood that probe 162 may incorporate a disposable probe cover 172 that can be replaced to avoid cross-contamination among patients.

The entire sensing portion, including the extension, may be disposable, to help prevent the spread of germs or diseases that may be transmitted through contact with an eye or related fluids. In an alternate embodiment, the IR sensing portion itself, the extension, or both may be covered by a sheath or sleeve of a disposable, sterile material. A variety of wave guides, as disclosed herein, can be used in accordance with the geometry of ABTT terminus 16 and the principles of the disclosure.

In the present disclosure, infrared sensor 42 is used in the sensing portion of the device to measure body temperature through ABTT terminus area 16. In alternate embodiments, reflectance spectroscopy, ultrasound, Raman spectroscopy, and the like may be used in the device to determine biological parameters, such as temperature or measurement of analytes, including glucose, cholesterol, ethanol, sodium, potassium, urea, creatinine, liver enzymes, heart enzymes, and the like, measurement of antibodies, and the like, from ABTT target area 16.

Figure 63:
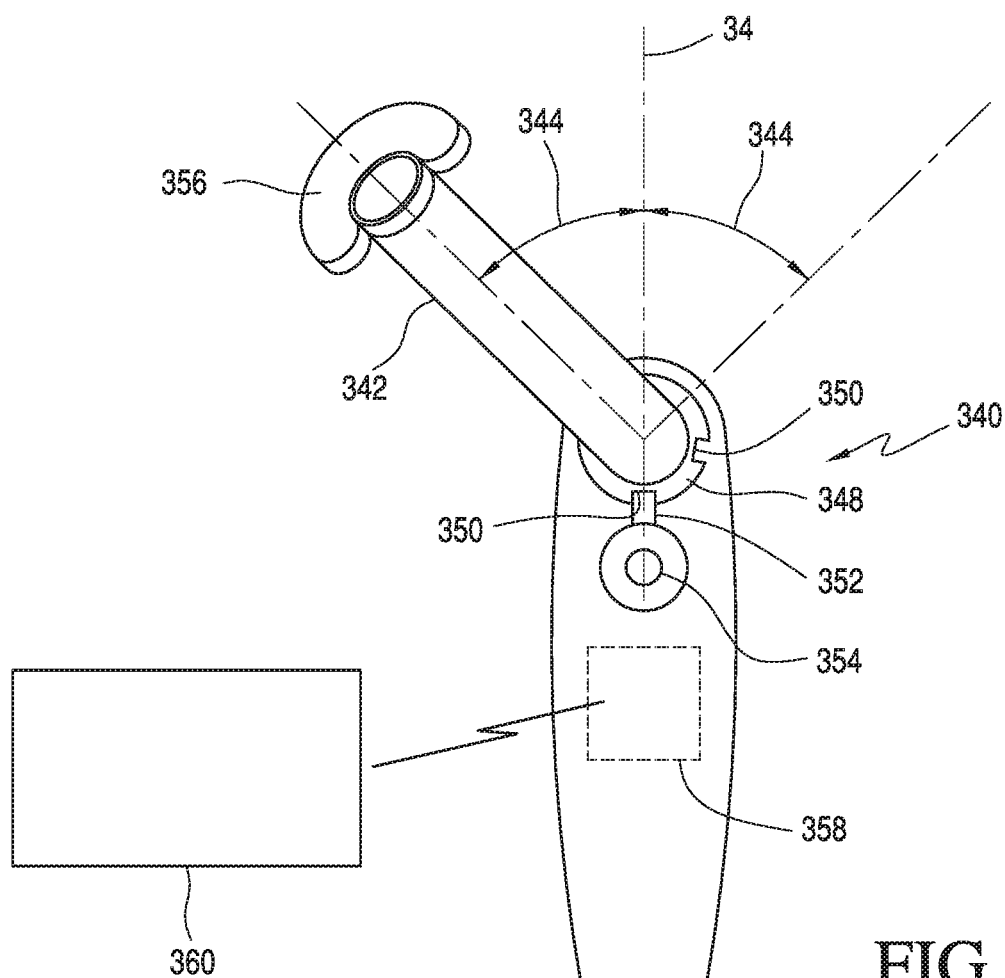
FIG. 63 is an end view, which may be considered a front view, of a sensing device in accordance with an exemplary embodiment of the present disclosure.
Figure 64:
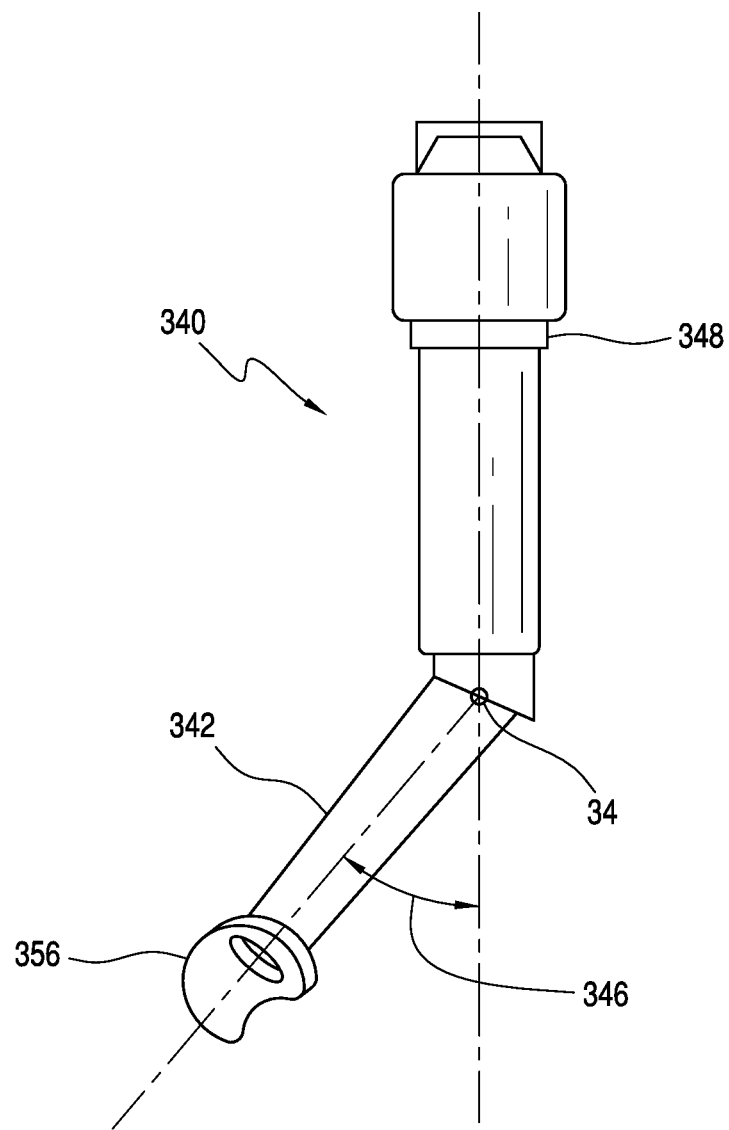
FIG. 64 is a top view of the sensing device of FIG. 63.

FIGS. 63 and 64 show another sensing device or apparatus in accordance with an exemplary embodiment of the present disclosure and indicated generally at 340. Sensing device 340 includes a sensing portion 342 that is at a first angle 344 when viewed from a front or end of sensing device 340, as shown in FIG. 63, and a second angle 346 when viewed from a top of sensing device 340, as shown in FIG. 64. Exemplary embodiments of first angle 344 can be the same as for predetermined angle 14. Exemplary embodiments of second angle 346 can be the same as angle 36 shown in FIG. 16. One benefit to the configuration of FIGS. 63 and 64 is that sensing portion 342 is angled to optimally mate with ABTT terminus 16, which can make it easier for some subjects or patients to orient sensing device 340 with respect to ABTT terminus 16 when making a measurement of ABTT terminus 16.

Sensing device 340 includes other features that may be incorporated in other sensing device embodiments described herein. Sensing device 340 is configured to rotate from the orientation shown in FIG. 63 by two times angle 346 to enable sensing device 340 to measure either right or left ABTT terminus 16. In an exemplary embodiment, rotation of sensing portion 342 from the left to the right may be accomplished by a rotating interface 348. Rotating interface 348 may be positioned in a fixed orientation by engagement of a detent 350 with an engaging apparatus, device, or mechanism 352, which may be operated or actuated by an actuation device or button 354. Each detent 350 is located to establish second angle 346 in a left, or counter clockwise rotation from a vertical direction along axis 34, or to establish second angle 346 in right, or clockwise rotation from a vertical direction along axis 34.

Sensing device 340 further includes an extension 356 that is configured to mate with the unique area around ABTT terminus 16 to aid in positioning sensing portion 342 for measurement. Extension 356 is configured to be removable such that extension 356 can be configured in a right version and a left version to mate with right ABTT terminus 16 and left ABTT terminus 16. In an exemplary embodiment, extension 356 is formed of a dark colored, semi-rigid plastic, which may be sterilized or may be disposable. It should be understood that extension 356, or a similarly configured extension 356, can be attached to any of the sensing devices disclosed herein.

Figure 63A:
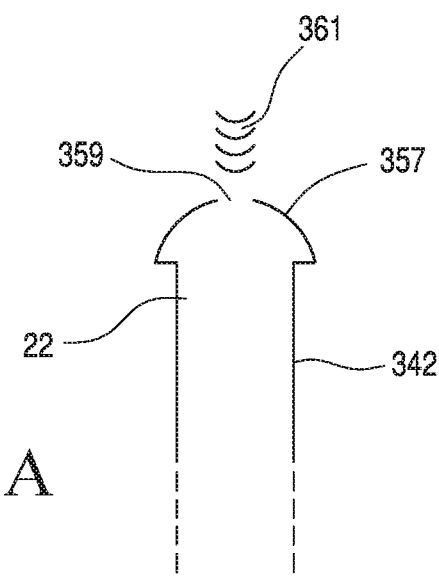
FIG. 63A is a side view of a second free end of a sensing portion in accordance with an exemplary embodiment of the present disclosure.

It should be understood, as shown in FIG. 63A, that second free end 22 of sensing portion 342 can preferably include an essentially convex or round surface 357 configured to mate with the unique essentially concave area of ABTT terminus 16 to aid in scanning the area of ABTT terminus 16 by moving second free end 22 around the center of ABTT terminus 16. Convex end 357 preferably includes an opening 359 configured to receive radiation 361 emitted from ABTT terminus 16. It should be understood that this disclosure includes a method for determining the center of ABTT terminus 16 or hot spot, including a first step of moving second free end 22 in apposition to the skin of ABTT terminus 16 along the "scanning area," the scanning area including the region along the side of the nose and the area of the medial half of the upper eyelid between the eye and the eyebrow, a second step of determining the highest temperature, and a third step of reporting the detected highest temperature. It should be understood that the method may include a non-contact method for scanning the "scanning area".

To accomplish the method, second free end 22 is configured to have a maximum diameter equal to or less than 15 mm. In another embodiment, second free end 22 is configured to have a maximum diameter equal to or less than 12 mm. In yet another embodiment, second free end 22 is configured to have a maximum diameter equal to or less than 7 mm. In a further embodiment, second free end 22 is configured to have a maximum diameter equal to or less than 5 mm.

Figure 63B:
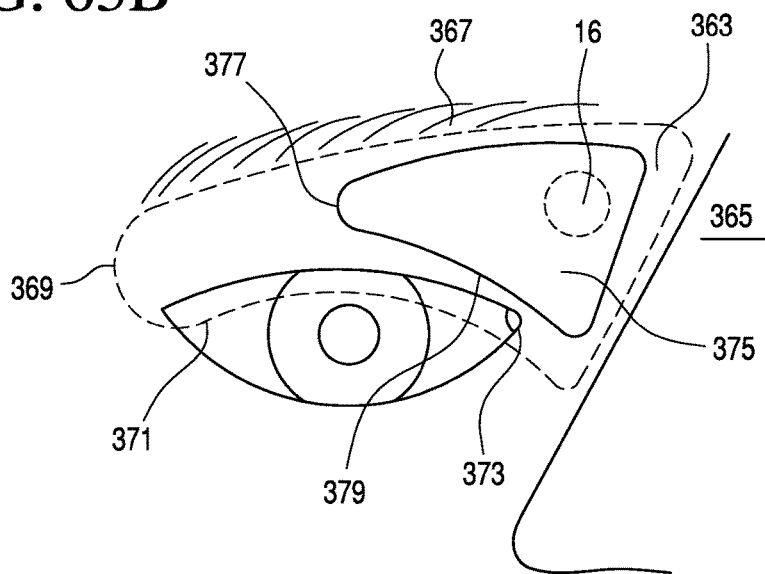
FIG. 63B shows exemplary areas to be scanned to locate the ABTT terminus.

FIGS. 63B to 63F show exemplary scanning methods and preferred areas being scanned. FIG. 63B shows the most frequent location for ABTT terminus 16 and two preferred boundaries of an area 363 and an area 375 to be scanned or covered by a sensor, by contact or non-contact with a sensor. Larger area 363 demarcated by dashed lines includes the following boundaries: a nose 365, an eyebrow 367, which includes eyebrow 367 but not the forehead, a lateral end of an upper eyelid 369, and a superior portion of an eyeball 371, including the caruncle and tear duct 373. Smaller scanning area 375 is demarcated by solid lines has the following boundaries: nose 365, eyebrow 367, including eyebrow 367, but not the forehead, the mid half of upper eyelid 377, and a free edge of an eyelid 379.

Figure 63C:
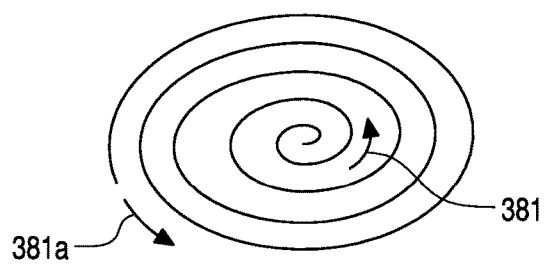
FIG. 63C shows a first method of scanning for the ABTT terminus in accordance with an exemplary embodiment of the present disclosure.
Figure 63E:
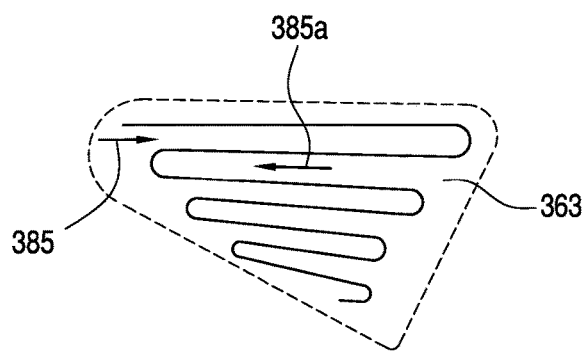
FIG. 63E shows a third method of scanning for the ABTT terminus in accordance with an exemplary embodiment of the present disclosure.
Figure 63D:
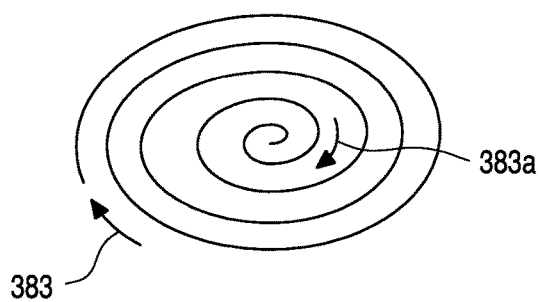
FIG. 63D shows a second method of scanning for the ABTT terminus in accordance with an exemplary embodiment of the present disclosure.
Figure 63F:
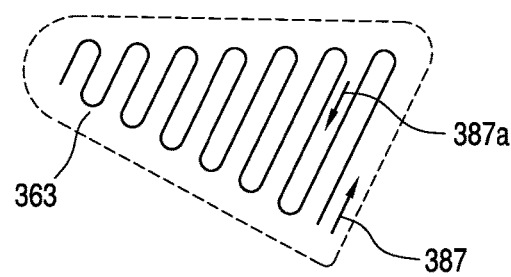
FIG. 63F shows a fourth method of scanning for the ABTT terminus in accordance with an exemplary embodiment of the present disclosure.

Considering the most likely position of ABTT terminus 16, scanning a smaller area reduces time for detecting the main point or hot spot of ABTT terminus 16. FIG. 63C shows a first exemplary method, including a preferred spiral motion for scanning, initiating at a center around ABTT terminus 16 and moving to a periphery as per arrows 381 and 381 *a*. FIG. 63D can represent a second exemplary method or step that includes a spiral motion starting at the periphery and moving to ABTT terminus 16 as shown by arrows 383 and 383 *a*. FIG. 63E shows a third exemplary method for scanning area 363, including a left to right horizontal motion toward the nose as per arrow 385 for left ABTT terminus 16, followed by a right to left motion as per arrow 385 *a*. FIG. 63F can represent fourth exemplary method or a second step to the step of FIG. 63E that includes an up and down motion for scanning area 363, starting at a lower edge adjacent to the nose as per arrow 387 and moving upwards, followed by a downward motion as per arrow 387 *a*. It should be understood that a method that focuses on the most frequent location of ABTT terminus 16, may include focusing on ABTT terminus 16 with short right and left motion, and short right and left motion that includes a preferred area measuring from the center of the ABTT terminus a diameter equal to or less than 25 mm, preferably a diameter equal to or less than 15 mm, and most preferably a diameter equal to or less than 10 mm.

FIG. 63G shows another exemplary scanning area 393 that is demarcated by solid lines, and that has an essentially triangular shape and the following boundaries: nose 365, eyebrow 367, including eyebrow 367 but not the forehead, and a line that starts at the lateral end of an eyebrow 389 and a lateral corner of an eye 391 terminating at nose 365.

FIG. 63H shows an exemplary scanning area for an animal to identify the equivalent of the ABTT terminus in humans, represented in FIG. 63H by a canine species. A scanning area 395 demarcated by solid lines has an essentially triangular shape and the following boundaries: an upper portion of a nose 399, an edge of an upper eyelid 403, and an edge of an lower eyelid 401, including the transition area 397 previously described (encompassing an anterior corner of an eye and lacrimal duct area.

Figure 63I:
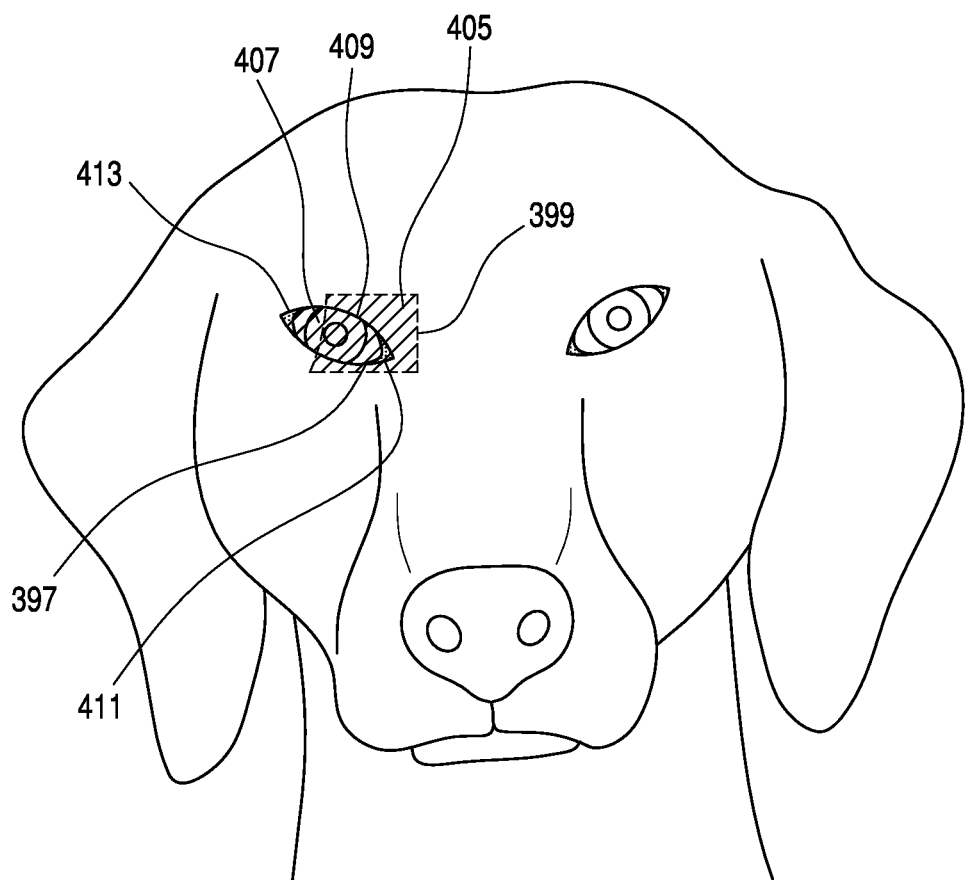
FIG. 63I shows another exemplary scanning area for an animal in accordance with an exemplary embodiment of the present disclosure.
Figure 63J:
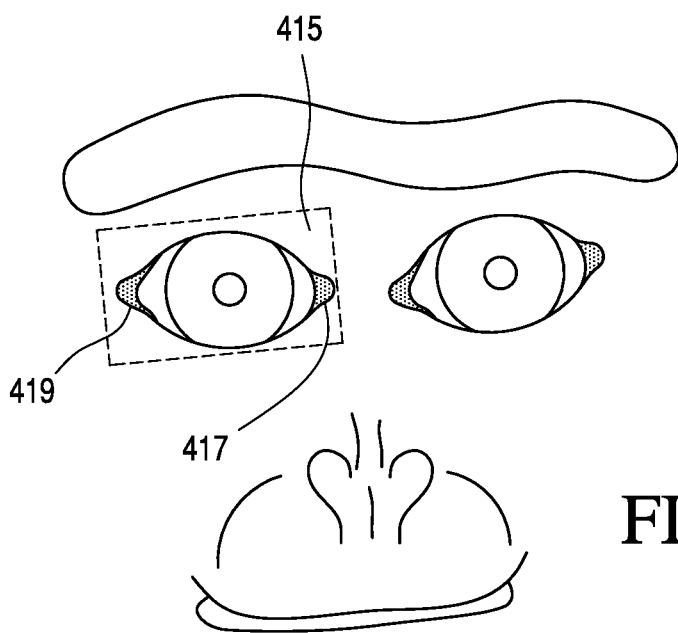
FIG. 63J shows yet another exemplary scanning area for an animal in accordance with an exemplary embodiment of the present disclosure.

FIG. 63I shows another exemplary scanning area configured with a smaller dimension 405 in accordance with the present disclosure, demarcated by dashed lines that have the following boundaries: an upper portion of nose 399, a mid portion of an eyeball 407 at a level of an edge of an upper eyelid 409, and an edge of a lower eyelid 411, including the transition area and a medial eye corner, but not a lateral eye corner 413. Scanning area 415 is preferable for scanning the ITP for primates, including chimpanzees, and preferably includes both a transition area 417 at a medial corner and a lateral eye corner 419, as shown in FIG. 63J. Motions similar to the motions shown in FIGS. 63C-63F can be used for scanning areas 395, 405, and 415.

Sensing device 340 further includes a transmitter 358 configured to receive data from a sensor such as those described herein. Transmitter 358 then transmits the data to a receiving device 360, such as a cell phone, computer, tablet, etc., which displays the received data. Sensing device 340 may be configured to transmit complete video information to receiving device 360, or receiving device 360 may include an application or program formatted to display information received from sensing device 340.

Figure 65:
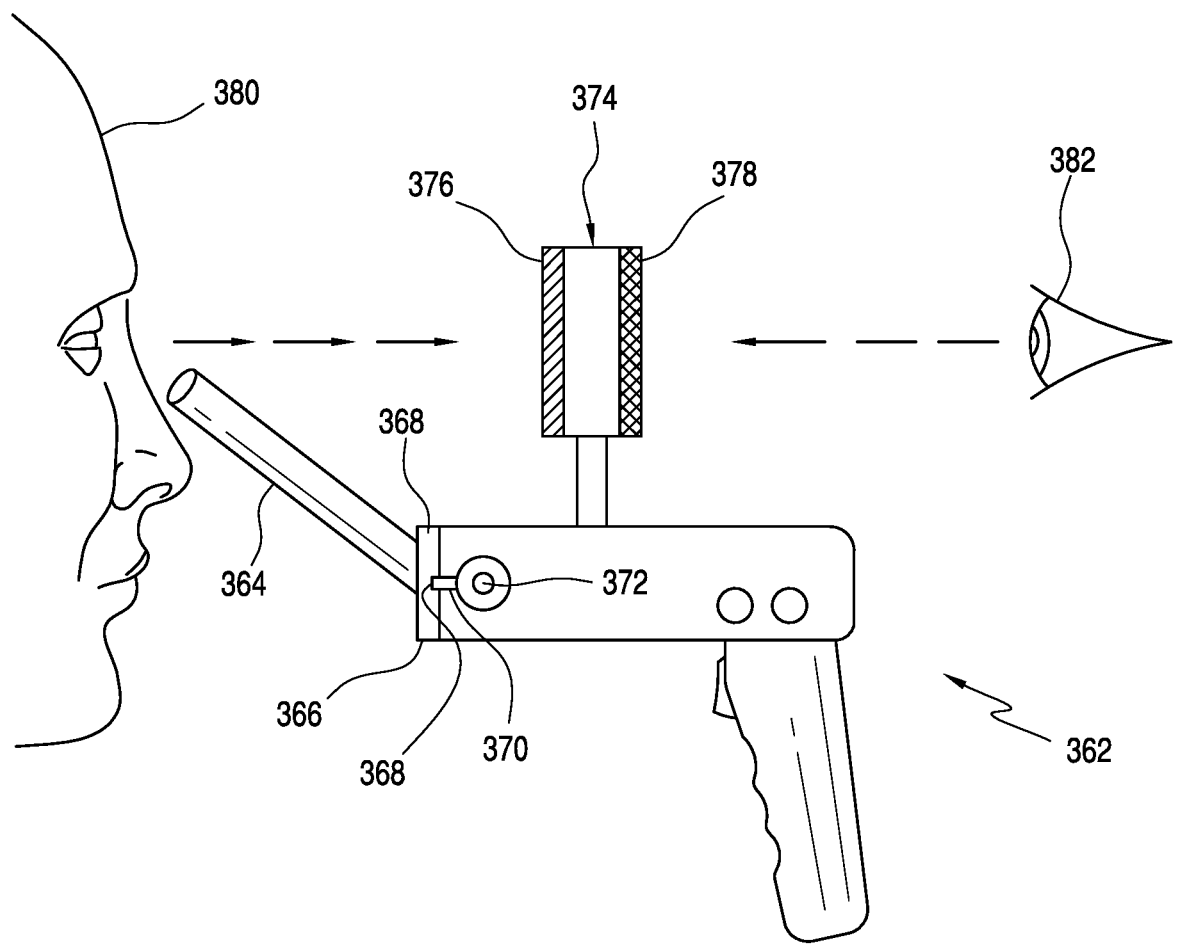
FIG. 65 is a view of another sensing device in accordance with an exemplary embodiment of the present disclosure.

FIG. 65 is a side view of another sensing device or apparatus in accordance with an exemplary embodiment of the present disclosure and indicated generally at 362. Sensing device 362 includes a sensing portion 364 that is rotatable about a rotating interface 366 that is positionable at predetermined angles, similar to the configuration of FIGS. 63 and 64. Rotating interface 366 can include detents 368 configured to receive an engaging apparatus 370, which may be operated by an actuation device, apparatus, or mechanism 372. Sensing apparatus 362 further includes a viewing or display apparatus 374 that includes a first display 376 configured to be in a location readily viewable by a subject or patient 380, and a second display 378 configured to be in a location readily viewable by an operator 382, which can be a nurse, doctor, technician, care giver, or other person conducting a measurement on subject 380. It should be understood that in an exemplary embodiment, display apparatus 374 may be configured to include only one display such as first display 376 that can be rotated to allow first display 376 to be viewed by either patient 380 or operator 382.

The dual display configuration of apparatus 374 is beneficial for multiple reasons. When sensing device 362 is used on a child, for example, first display 376 may present a short subject, such as an animation, humorous event, action event, or the like, while the operator, which may be a parent in this example, receives information about the child's condition. The displayed image for the child helps to reduce tension of the child and may even encourage the child to accept the device in exchange for seeing the short subject. Of course, first display 376 and second display 378 may also present the same information, or may present a display selected by subject or patient 380 while operator 382 views data output of sensing device 362.

In an exemplary embodiment, an IR sensor may be an array of infrared sensitive pixels configured as a camera, such as the IR sensor shown in FIG. 66 and indicated generally at 384. FIG. 663 also shows a stylized output of IR sensor 384, which may be analyzed in a controller to determine, for example, a peak temperature 386 of ABTT terminus 16, and an average temperature 388 of ABTT terminus 16. In an exemplary embodiment, peak temperature 386 is the highest temperature indicated by a limited number or one pixel element 390 of IR sensor 384. Also in an exemplary embodiment, average temperature 388 of ABTT terminus 16 can be determined as a region of temperatures within a particular temperature band of the peak temperature, such as a percentage of peak temperature 386, or a band measured in degrees, such as 0.1 degrees of the peak temperature. IR sensor 384 can also be configured to provide a map 392 of temperatures around ABTT terminus 16, which can then be analyzed for abnormalities.

As previously discussed, a sensing device or apparatus may include an extension that is configured to be attached to an end of a sensing portion to separate the sensing portion from a patient or subject and that permits sterilization or disposal of the extension. An exemplary extension in accordance with the present disclosure is shown in FIGS. 67 and 68 and indicated generally at 394. Extension 394 is configured to be securely attached or positioned on a sensing portion, such as sensing portion 396 shown in FIGS. 67 and 68. Extension 394 includes open area 499 and may include an interior chamfer 398 to aid sliding extension 394 over a corner 400 of sensing portion 396. In an exemplary embodiment, extension 394 is configured to include a ring-like configuration 433 and is formed of a dark, semi-rigid or rigid plastic, with dark including dark gray, dark blue, dark red, black, etc. In an exemplary embodiment, extension 394 is configured as an annulus or ring. A benefit of extension 394 is that it is readily removable for sterilization or disposal.

Figure 69:
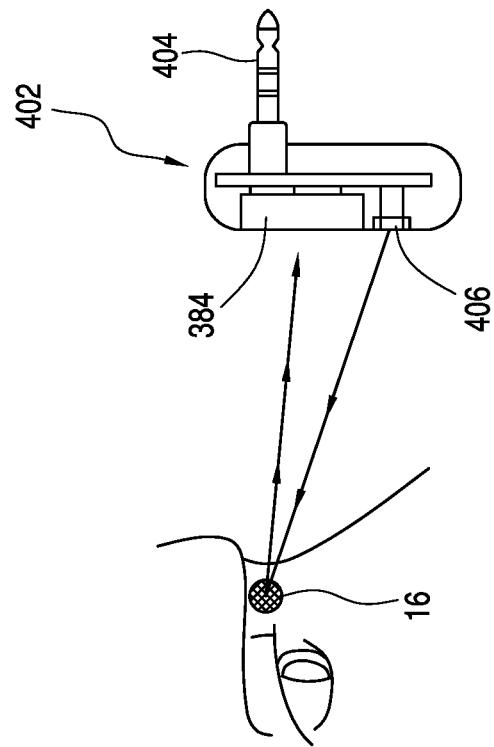
FIG. 69 is a view of a sensing device or apparatus configured to be attached to a separate device in accordance with an exemplary embodiment of the present disclosure.

Though sensing devices and apparatuses to measure ABTT terminus 16 have generally been shown as including a handle, buttons, and the like, a sensing device may be small device configured to mate with, for example, a cell phone, tablet, or other small electronic device, such as sensing device shown in FIG. 69 and indicated generally at 402. Sensing device 402 can include, in an exemplary embodiment, IR imaging array 384. In an exemplary embodiment, sensing device 402 includes a plug 404 for mating with a cell phone or other compatible device. In an exemplary embodiment, sensing device 402 is configured to include an IR led 406 to provide illumination for IR receiver or imaging array 384 to improve the image provided on imaging array 384 to help locate ABTT terminus 16.

Figure 70:
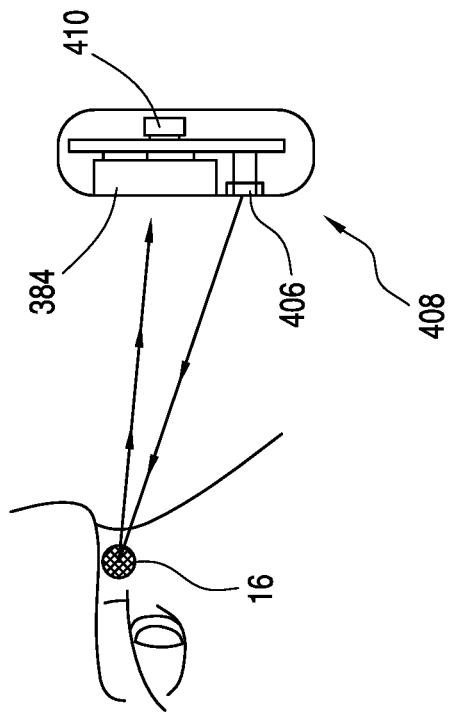
FIG. 70 is a view of a sensing device or apparatus similar to the sensing device of FIG. 69, only configured to communicate with a separate device wirelessly.

FIG. 70 shows another sensing device in accordance with an exemplary embodiment of the present disclosure and indicated generally at 408. Sensing device 408 is similar to sensing device 402, but uses a wireless transmitter or transceiver 410 in place of or in addition to plug 404.

FIGS. 71-75 show exemplary configurations of the output of the sensing devices and apparatus of the present disclosure, including, as an example, sensing devices 402 and 410. In the exemplary embodiment of FIG. 71, an electronic device 412 includes a display 414. The software for display of data from a sensing device in this embodiment is free or very low cost, but appears with advertisements to help subsidize the cost of the software or the sensing device, or both. After the advertisement portion is complete, which can be configured to play during measurement or data acquisition and analysis, the results of the measurement can be displayed, for example, as shown in FIG. 72.

An upgraded version of display software, such as is shown in FIG. 73, can be configured to provide additional information to a user, such as, for example, risk of infection, risk of stroke, etc. Such upgraded software may be provided at an additional cost, as an incentive to purchase a more sophisticated sensing device, or free.

Software may be further upgraded as shown in FIGS. 74 and 75 to provide data for both ABTT terminuses 16, to provide analysis and/or diagnostics, as shown in display area 416 of electronic device 412, including displayed data, such as map 392 in FIG. 66B, and may be without advertisements. As with the embodiment shown in FIG. 73, this embodiment may be provided at an additional cost, as an incentive to purchase a more sophisticated sensing device, or free, for example, as a promotional device.

Sensing device 10 in accordance with an exemplary embodiment of the present disclosure includes handle portion 24. Handle portion 24, which may also be described as an arm portion 24, may be used by an operator or user for holding sensing device 10. In an exemplary embodiment, as shown in FIGS. 1-17, arm or handle portion 24 is connected to body portion by adjustable connection mechanism 26, and thus handle portion 24 is adjustably positioned with and adjustably connected to body portion 20 wherein a plurality of orientations of handle portion 24 may be obtained. The adjustable nature of arm or handle portion 24 allows for a plurality of device holding configurations. Exemplary embodiment sensing apparatus 10 including handle portion 24 is configured so that an operator may either take a temperature measurement of another person, or of himself or herself.

In a first scenario, a doctor or other medical practitioner may use sensing apparatus 10 for measuring the body temperature of a patient or subject. For a single sensing device 10 to have the dual uses described herein, one aspect of the disclosed embodiments is that adjustable arm portion 24 allows for better balance of sensing device 10 during measurement. In one embodiment, arm portion 24 is connected to body portion 20 using adjustable connection mechanism 26, which may include a hinge, screw fastener, and/or other suitable adjustable method of connection which allows the arm position to be rotated from a straight or 180 degree configuration related to body portion 20, as shown in FIG. 1, to a 90 degree vertical orientation, as shown in FIG. 2.

Figure 2:
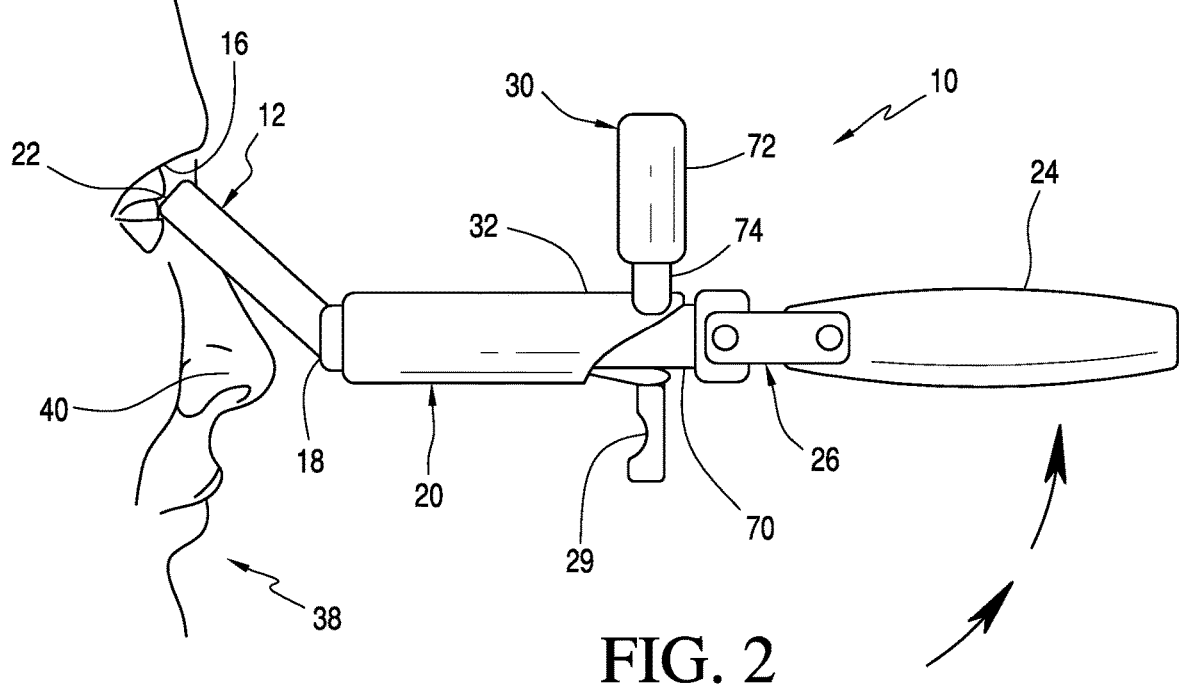
FIG. 2 is a side view of the sensing device of FIG. 1, with the handle portion in a second position.

The 180 degree orientation of FIG. 2 enables an operator to use IR sensing device 10 on himself, so that sensing device 10 is optimally balanced and stable during use. The operator may comfortably use sensing device 10 with his arm extended, so as to achieve the ideal angle for reaching ABTT target area 16 with sensing device 10. Alternatively, the 90 degree orientation of FIG. 2 provides better stability and balance for an operator to take measurements of another person. The 90 degree orientation also allows for better arm positioning for the operator during use, as the elbow can be easily kept near the body without affecting balance. This orientation enables sensing device 10 to be used in a clinical setting, such as a doctor's office-type setting, where space may be limited.

Figure 11:
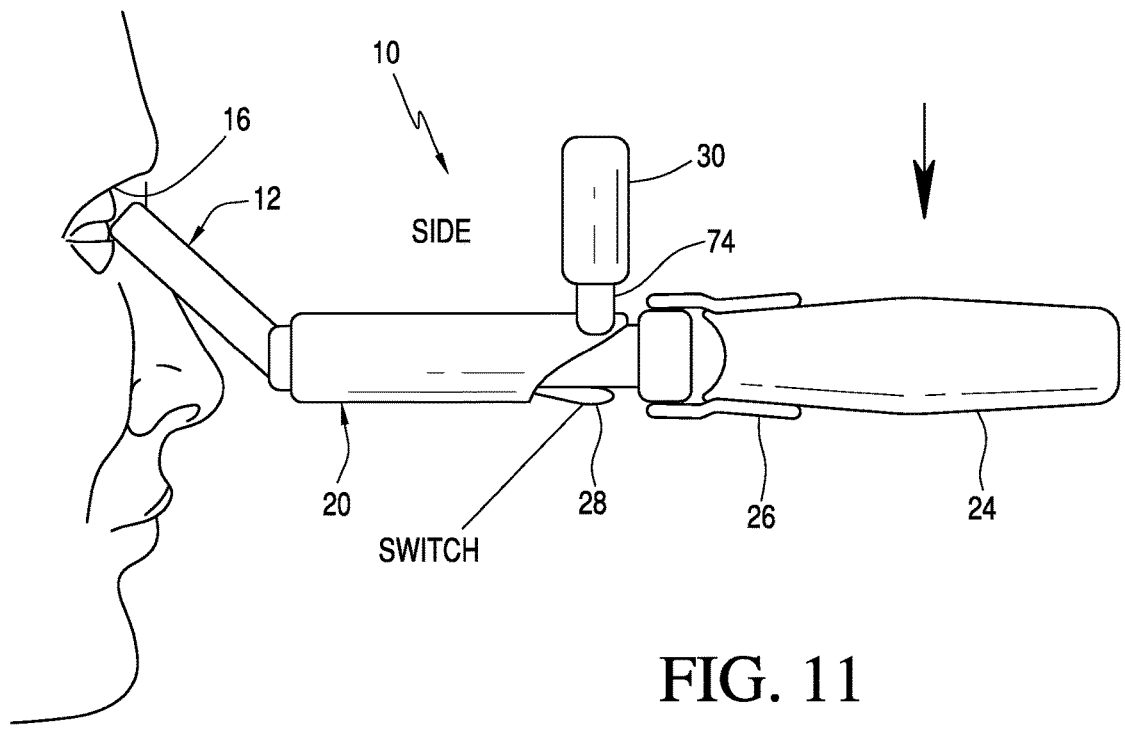
FIG. 11 is a view of the sensing device similar to the view of FIG. 2, with the handle portion rotated by 90 degrees about an axis of the sensing device.
Figure 12:
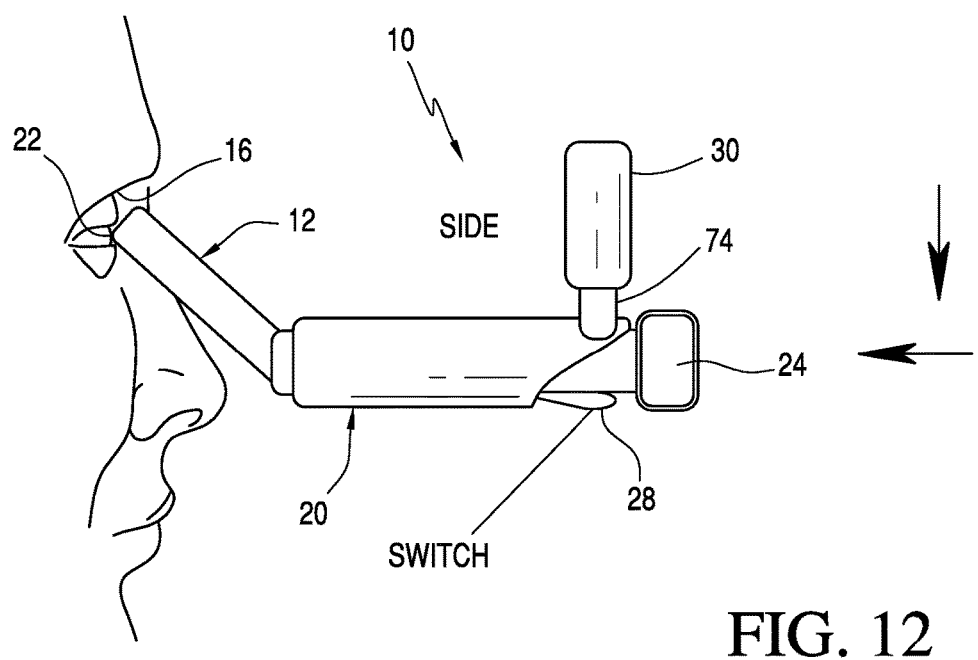
FIG. 12 is a side view of the sensing device of FIGS. 3 and 5.

In alternate embodiments, arm portion 24 may also be positioned to any suitable vertical orientation between 90 and 180 degrees. As is presented in FIGS. 2-6, arm portion 24 may also be joined to body portion 20 by adjustable connection mechanism 26 that allows arm portion 24 to be rotated 90 degrees to the left or right, allowing handle portion 24 to rest at a 90 degree orientation in the horizontal plane with body portion 20, as shown in FIGS. 3 and 5, contrasted with the aforementioned vertical orientation of handle portion 24 shown in FIGS. 1, 4 and 6. In alternate embodiments, adjustable connection mechanism 26 may allow for 360 degrees of rotation, so that when handle portion 24 is at the 90 degree orientation in relation to body portion 20, it may be rotated in a full 360 degrees around body portion 20. As shown in FIGS. 11 and 12, adjustable connection mechanism 26 may also allow handle portion 24 to be rotated around body portion 20 when handle portion 24 is oriented 180 degrees in relation to body portion 20. The many adjustable orientations of arm portion 24 related to body portion 20 allows an operator to position arm portion 24 so that it is most comfortable for use and, most importantly, adjusted for the anatomy of ABTT terminus area 16, thereby allowing optimal measurements.

Figure 13:
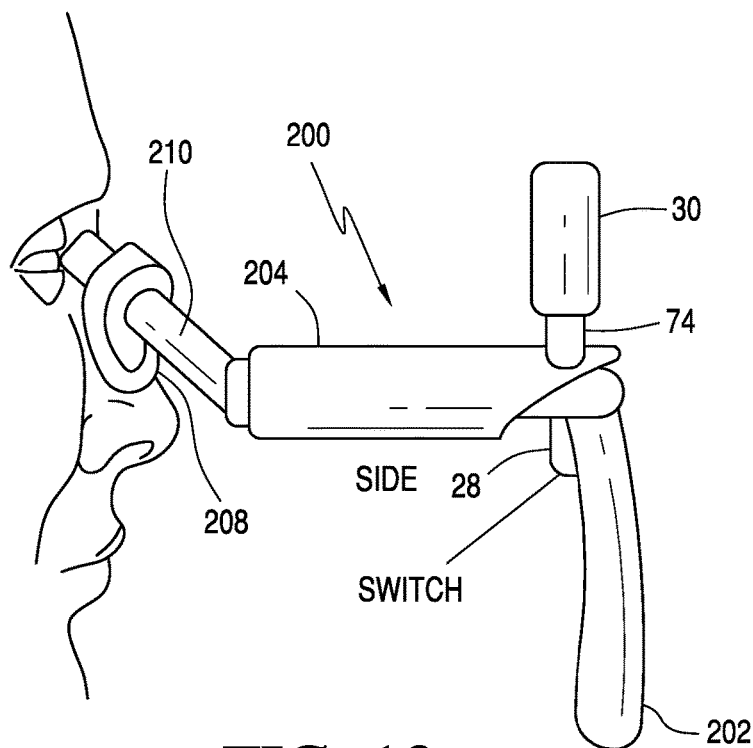
FIG. 13 is a side view of a sensing device in accordance with an exemplary embodiment of the present disclosure.
Figure 14:
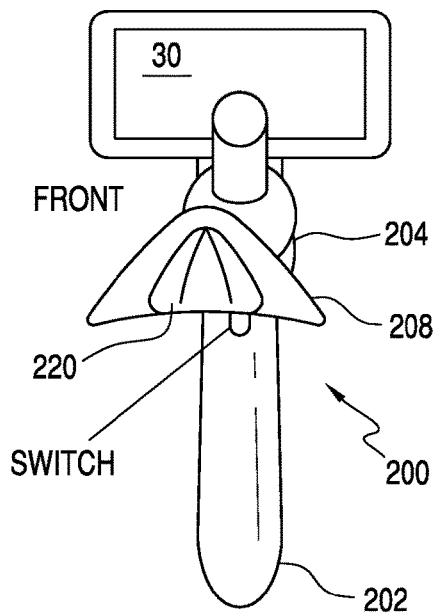
FIG. 14 is a front view of the sensing device of FIG. 13.
Figure 15:
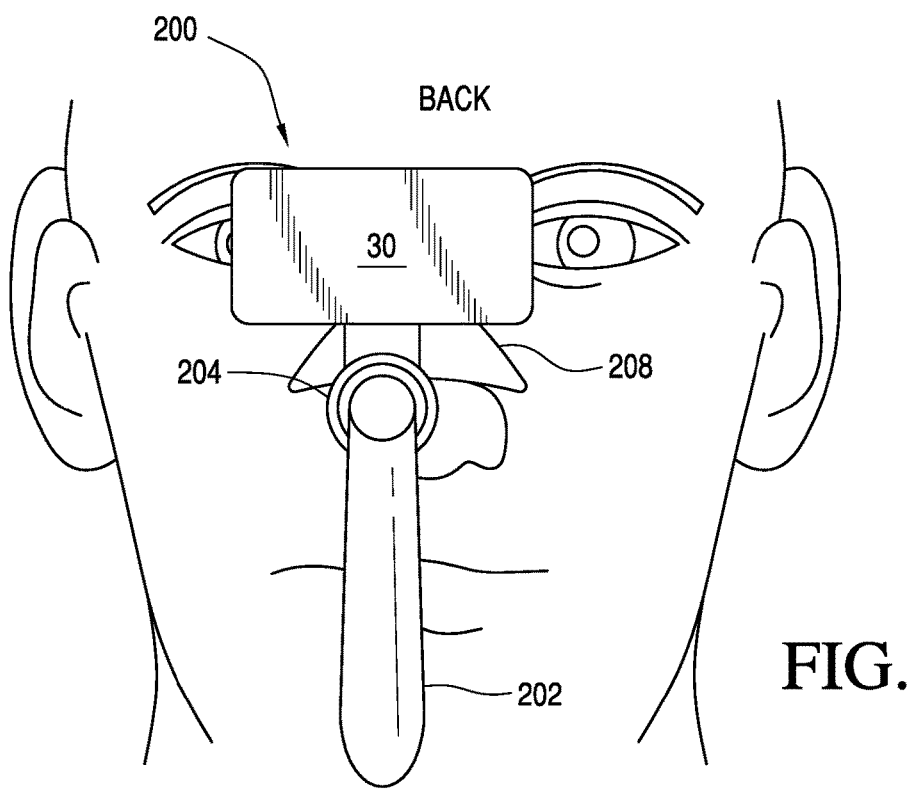
FIG. 15 is a back view of the sensing device of FIG. 13.

Alternate embodiments may be found in FIGS. 13-39, in which an arm portion is immovably fastened to a body portion so that the handle orientation is fixed and may not be adjusted. FIGS. 13-15 show an example of a sensing device 200 where an arm portion 202 is immovably fixed in an approximately 90 degree orientation with respect to a body portion 204. This orientation would be ideal for a device used in a setting such as a doctor's office, where an operator administers a measurement of another person. FIGS. 18-22 show a sensing device 230 where an arm or handle portion 232 is immovably fixed in an approximately 180 degree orientation with respect to a body portion 234. This orientation is ideal for sensing devices for home use or similar settings where an operator takes temperature measurements on himself.

It may be challenging for some users to find ABTT terminus 16 easily. Accordingly, in an exemplary embodiment, as shown in FIGS. 13-15, a nose interface 208 may be attached to a portion of sensing device 200. Nose interface 208 may be positioned on a sensing portion 210 of sensing device 200. Nose interface 208 may include a cavity 220 configured to interface with a human nose. Nose interface 208 may be adjustable for varying nose sizes and shapes, and nose interface 208 will typically be formed of a soft or padded material, such as plastic or foam. Nose interface 208 may also be adjustable in orientation with respect to sensing portion 210 to refine the orientation of sensing portion 210 with respect to ABTT terminus 16. Nose interface 208 may be permanently fixed or removable and disposable.

It should be understood that the handle or arm portions disclosed in the various embodiments may be comprised of any suitable material, such as wood, metal, metal alloys, plastic, or other synthetic substances. The arm portion may also be covered in a rubber, plastic, or other natural or synthetic gripping surface, that can be removable or non-removable, disposable, reusable, or the like. The arm portion may also be configured to have an ergonomic shape, with finger grips, with a slight bulge, curvature, or rounding of the free end. The arm portion may also be appropriately weighted to provide for better balance and control.

Figure 18:
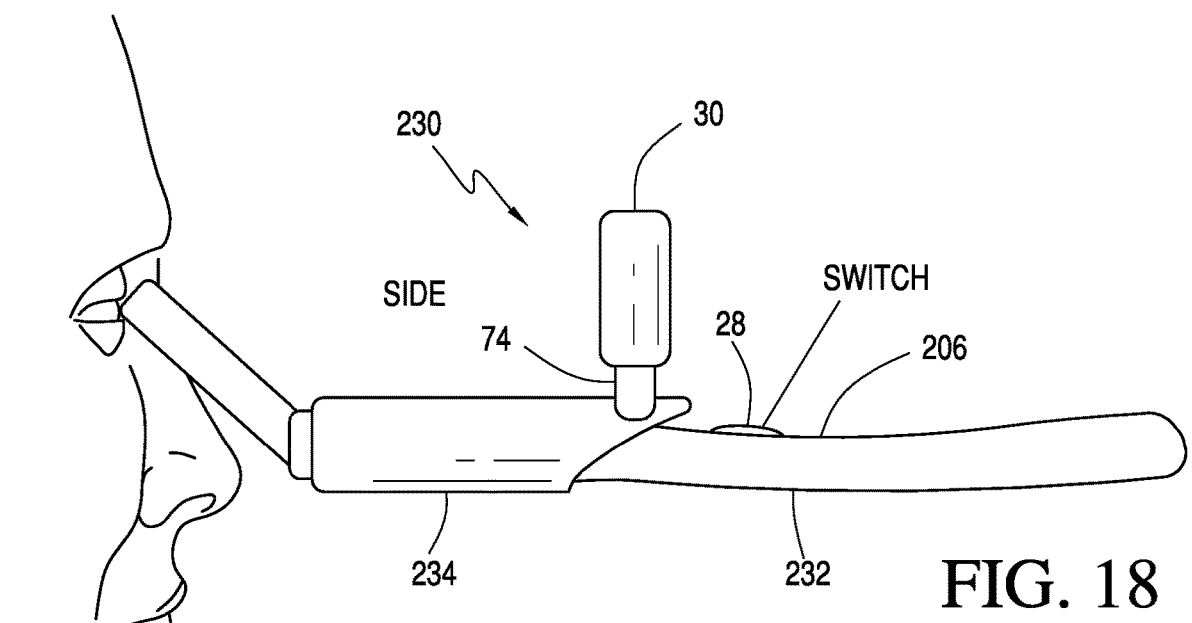
FIG. 18 is a side view of a sensing device in accordance with an exemplary embodiment of the present disclosure.
Figure 19:
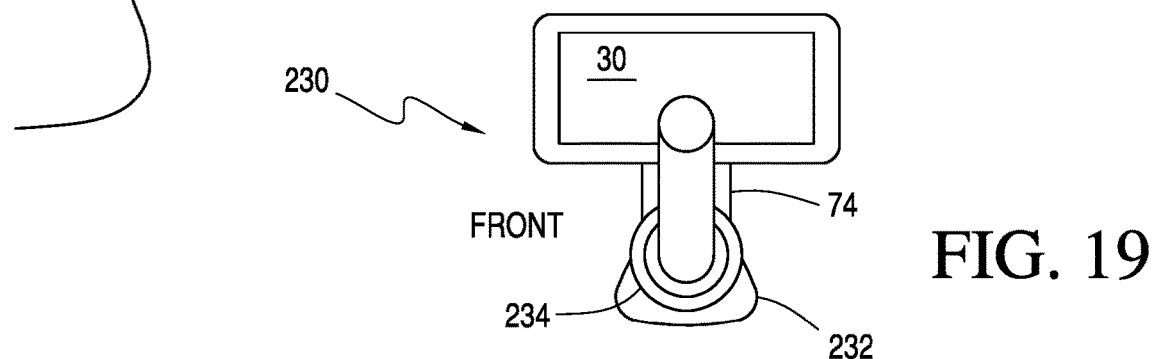
FIG. 19 is a front view of the sensing device of FIG. 18.
Figure 20:
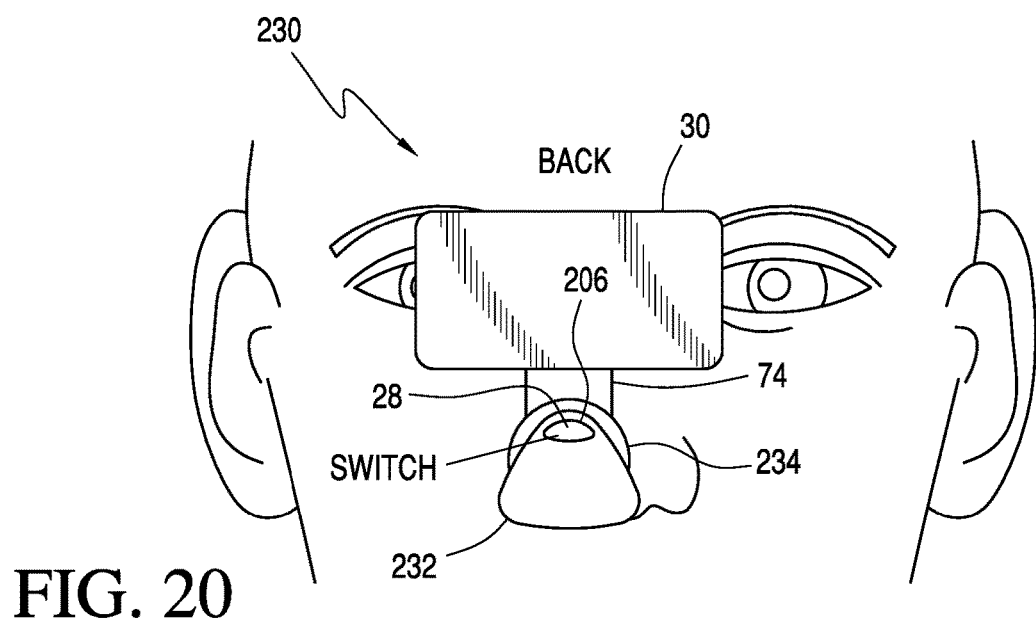
FIG. 20 is a back view of the sensing device of FIG. 18.
Figures 21, 22:
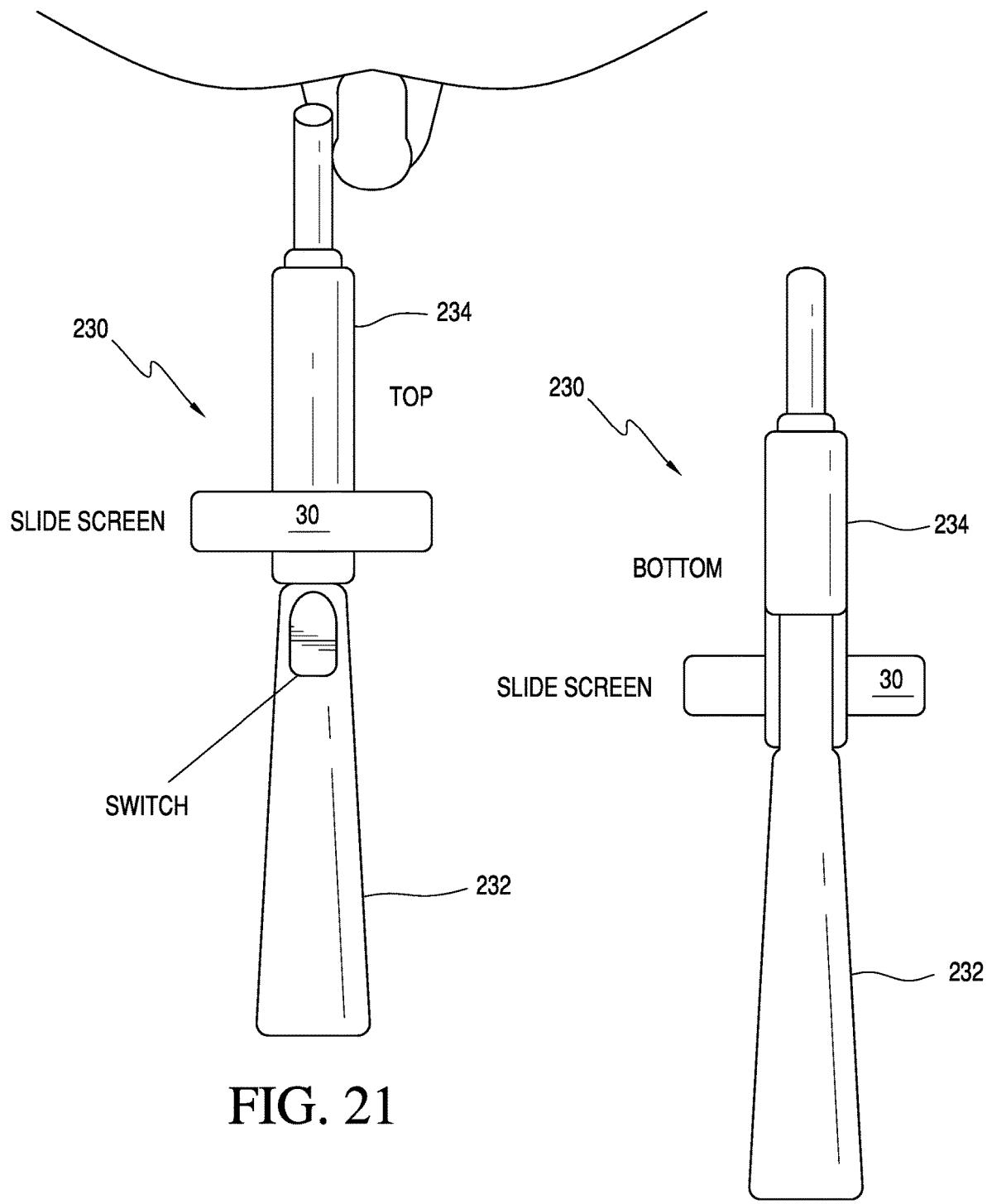
FIG. 21 is a top view of the sensing device of FIG. 18.
FIG. 22 is a bottom view of the sensing device of FIG. 18.
Figure 23:
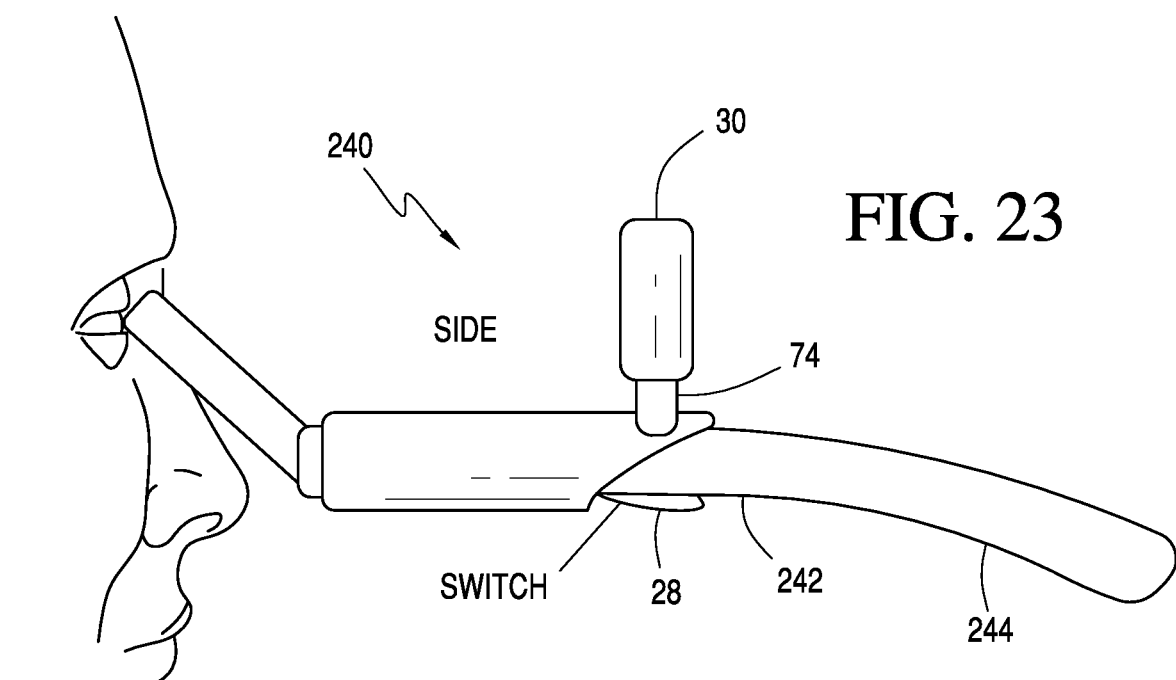
FIG. 23 is a side view of a sensing device in accordance with an exemplary embodiment of the present disclosure.
Figure 24:
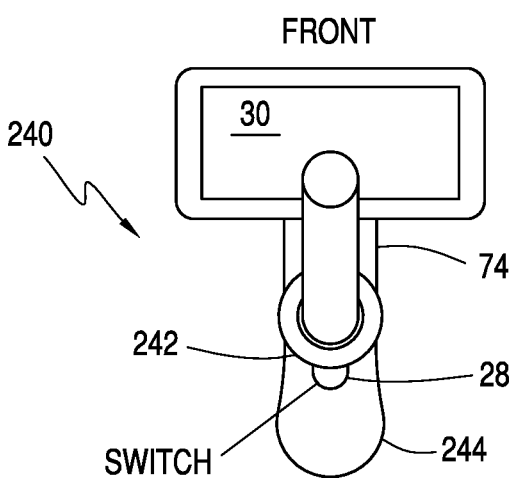
FIG. 24 is a front view of the sensing device of FIG. 23.
Figure 25:
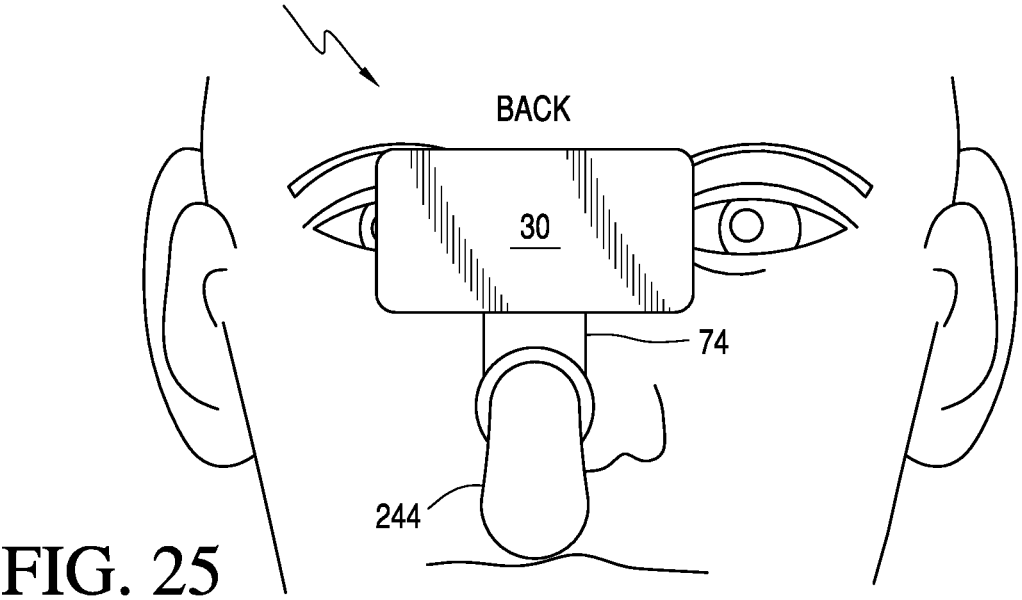
FIG. 25 is a back view of the sensing device of FIG. 23.
Figure 26:
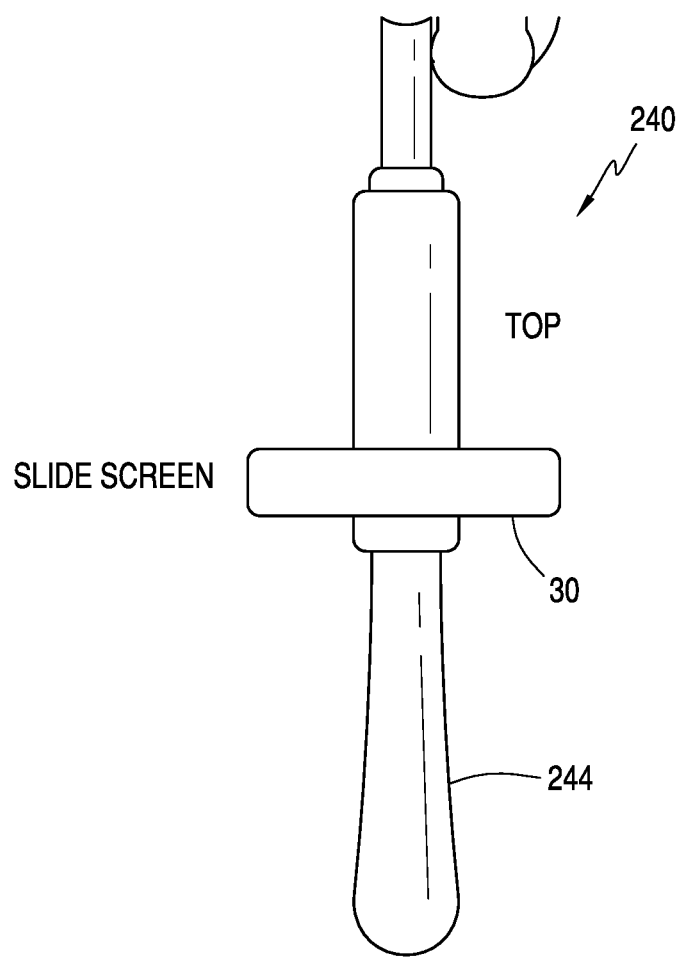
FIG. 26 is a top view of the sensing device of FIG. 23.

In an exemplary embodiment, sensing device 10 includes switch 28 located on an outer portion of sensing device 10 for activating the measurement function and other functions of the device. In one exemplary embodiment, as shown in FIG. 1, switch 28 may be located on an underside 70 of body portion 20 of sensing device 10, on an outer surface of body portion 20 of sensing device 10. This configuration is ideal for a sensing device configuration that comprises an adjustable handle feature, as switch 28 is not affected by the changing orientation of arm portion 24. It should be understood that in another exemplary embodiment the switch can be configured as a trigger switch 29 as shown in FIG. 2. In an alternate embodiment, as shown in FIGS. 13 and 14, when arm portion 202 is immovably fixed in the 90 degree orientation in relation to body portion 204, switch 28 may be located alongside arm portion 204. This orientation is ideal for use when a measurement is being administered by an operator on another person. In this "trigger-like" configuration, sensing device 200 may be activated by a simple action of the forefinger, for example. In yet another embodiment, as is shown in FIGS. 18 and 20, when arm portion 232 is immovably fixed in the 180 degree orientation with respect to body portion 234, switch 28 may be located on an upper side 206 of arm portion 202. This configuration allows for easier administration of an operator on himself using a forefinger when gripping arm portion 202. In FIGS. 23 and 24, this 180 degree orientation is also shown with switch 28 positioned on an underside 242 of an arm portion 244 of a sensing device 240. This configuration would allow self-administration with sensing device 240 being activated by an action of the thumb, for example. It should be understood that any combination of switches can be used, as well as multiple switches.

In an exemplary embodiment, switch 28 is of a hard key-type, which is physically activated by the operator. In alternate embodiments, switch 28 may be activated using one or more soft-keys, a touch screen, voice commands, remote control, or other activation configurations, including wireless or wired activation via a cell phone, watch, tablet, or any computing device.

In an exemplary embodiment, switch 28 is configured to activate temperature measurement or other measurements such as concentration of substances or any analytes by activating the IR sensing portion, such as sensing portion 12. In alternate embodiments, switch 28 may also be used to turn the sensing device on/off, or to activate the display, storage, or transmission of information created by the sensing device.

When a measurement is being taken using the ABTT IR sensing device as described herein, many times a viewer, or the person whose temperature is being measured, will have a fright reaction to the sensing portion, which, because of the location of ABTT terminus 16, is directed to a position very close to the eye during measurement. When an object appears to be heading toward the eye, it is often a first instinct to flinch, recoil, or otherwise move the head from the object in question. To alleviate some of the fright reaction associated with the use of the ABTT infrared sensing device, an exemplary ABTT sensing device is configured to include viewing portion 30, which assists in diverting the attention of the patient or subject away from sensing portion 12, to reduce a flinch, recoil, or other head movement during the approach of sensing portion 12 and while measurements are being taken. Viewing portion 30 may include, for example, patient friendly animation, an amusing short subject, videos, pictures, etc.

Exemplary embodiments of the sensing device or apparatus disclosed herein often include a viewing portion, such as viewing portion 30 shown in FIG. 1. Viewing portion 30 can be represented by a slide screen, a digital viewer, a standard display, or the like. Viewing portion 30 may include, as shown in at least FIG. 1, an upper portion 72 and a lower portion 74. Lower portion 74 is positioned on and attached to body portion 20 of sensing device 10, and may be positioned on and attached to body upper portion 32. Upper portion 72 is positioned on and attached to lower portion 74, and is configured to extend into a patient or subject's field of view. It should be understood that the sensing device or apparatus can include a video camera or photo camera (not shown) for filming ABTT terminus 16 and facilitate positioning the apparatus in the proper location to interface with ABTT terminus 16, with the acquired images being displayed on viewing portion 30, or alternatively on the screen of separate device such as a cell phone, computer, watch, and the like.

It should be understood that the word "slide screen" as used in this disclosure may refer to any apparatus or device for viewing an image or words, including any screen such as electronic, digital, LED, OLED, LCD, plasma, and the like.

A slide screen is defined herein as a relatively small component, which in an exemplary embodiment has a rectangular or square shape, and which may be either movably or immovably fixed to body portion 20 of sensing device or apparatus 10 for measuring body temperature or any biologic parameter through the ABTT by measurements made at the ABTT terminus 16. Lower portion 74 of the slide screen or viewing portion 30 is fixed to upper side 32 of body portion 20 of sensing device or apparatus 10, and is made of a rigid material so that a free or unsupported end 76 of slide screen or viewing portion 30 extends into the patient or subject's field of view or vision when sensing device or apparatus 10 is in use. A rigid material may be, for example, plastic, rigid paper, or other synthetic materials. It should be noted that a person looking at viewing portion or slide screen 30 may be a patient, subject, doctor or other medical practitioner, or other individual taking a measurement, and any person looking at viewing portion or slide screen 30 may be described as a viewing person or viewer. Because viewing portion 30 may be configured to display an image in two, opposite directions, a viewer on the same side as sensing portion 12 may be described as a patient or subject viewer, and a viewer on the opposite side of viewing portion 30 may be described as a testing or monitoring person, such as, for example, a nurse.

As is shown in FIGS. 1-29, viewing portion 30 comprises upper, horizontally oriented rectangular or square portion 72, and lower, vertically oriented portion 74. In an alternative embodiment shown in FIGS. 30-34, sensing device 128 includes a viewing portion 130 and a body portion 134. Viewing portion 130 includes a square side or upper portion 132, which is attached to body portion 134 by lower or attachment portion 136. In another alternative embodiment shown in FIGS. 35-39, a sensing device or apparatus 150 includes a body portion 152 and a viewing portion 154 positioned and/or attached to body portion 152. Viewing portion or slide screen 154 includes an upper or side portion 156 that is shown as a thin, smaller rectangle, and a lower or attachment portion 158 configured to attach upper portion 156 to body portion 152. It should be understood that slide screen or viewing portion 154 may be any one of a plurality of shapes and sizes so long as slide screen 154 extends into the field of view of a viewer, which may be a patient, subject, tester, or monitor.

Slide screen or viewing portion 30 shown in FIGS. 1-29 is positioned, mounted, or attached to a lateral center of a body portion of the sensing device, such as body portion 20 of sensing device 10, near to the arm portion of the device, such as arm portion 24 of sensing device 10. As such, when the sensing device is in use, as is shown in FIGS. 1, 2, 11, 12, 13, 15, 16, 18, 20, 21,23, and 25, slide screen 30 is positioned directly in the line of sight of the patient or subject and may be seen with both eyes. In an exemplary embodiment, slide screen or viewing portion 30 is mounted or attached to a specific, fixed position on the body portion of the sensing device, for example body portion 20 of sensing device 10. In another embodiment, the slide screen may be moved horizontally along the axis of the body portion, closer or farther from the viewer, to better facilitate the viewer's ability to focus on the slide screen display. The slide screen may include a variety of lenses for facilitating focusing of an image if the slide screen is located relatively closely to the eye, for example, at less than 15 cm from the eye.

Figure 27:
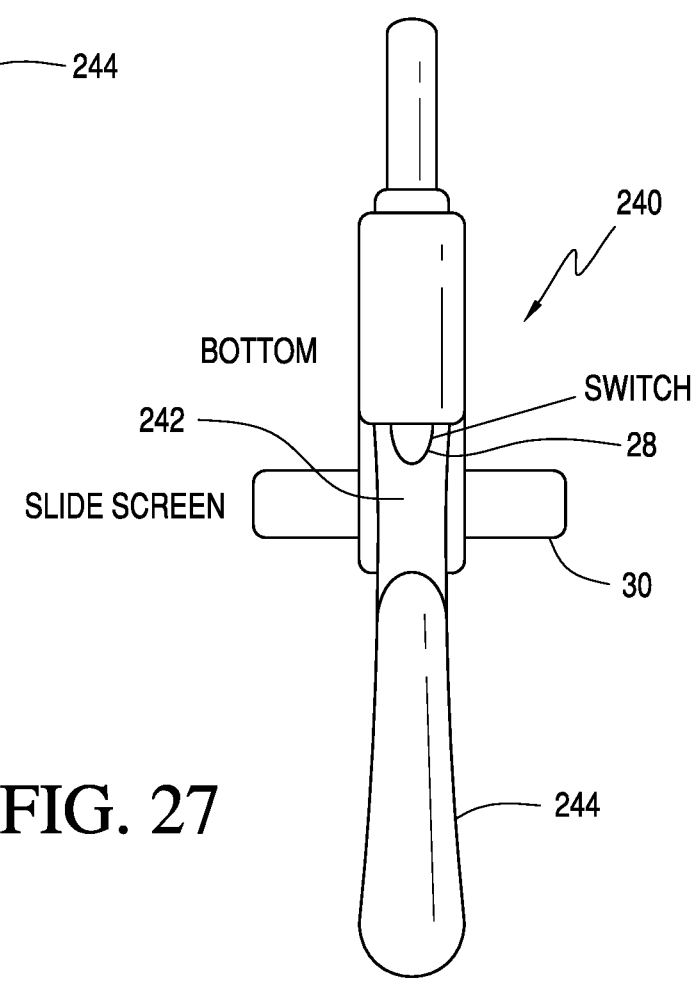
FIG. 27 is a bottom view of the sensing device of FIG. 23.
Figure 27A:
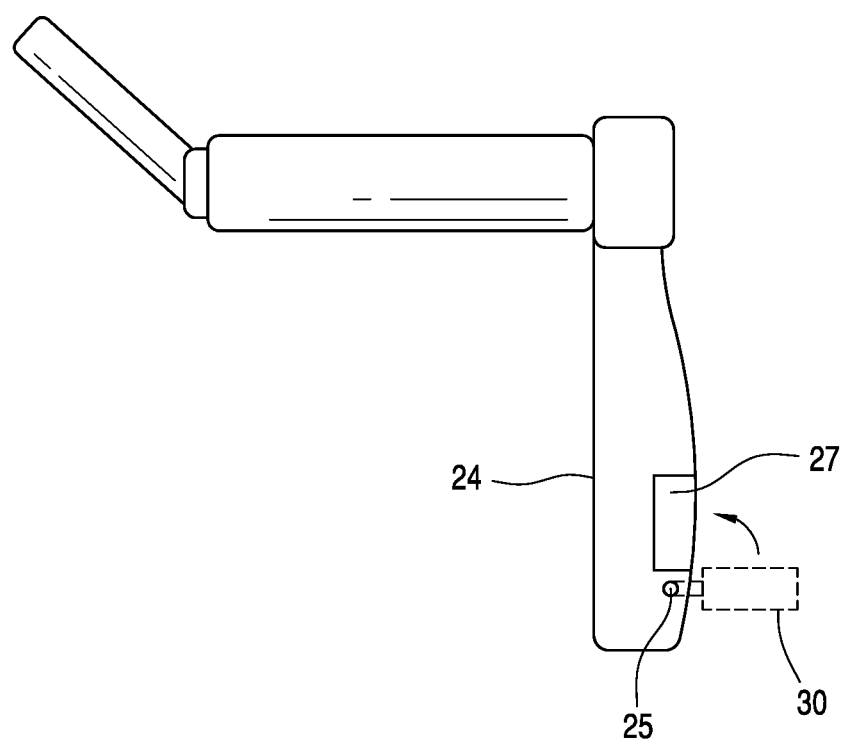
FIG. 27A is a side view of a sensing device in accordance with an exemplary embodiment of the present disclosure.
Figure 28:
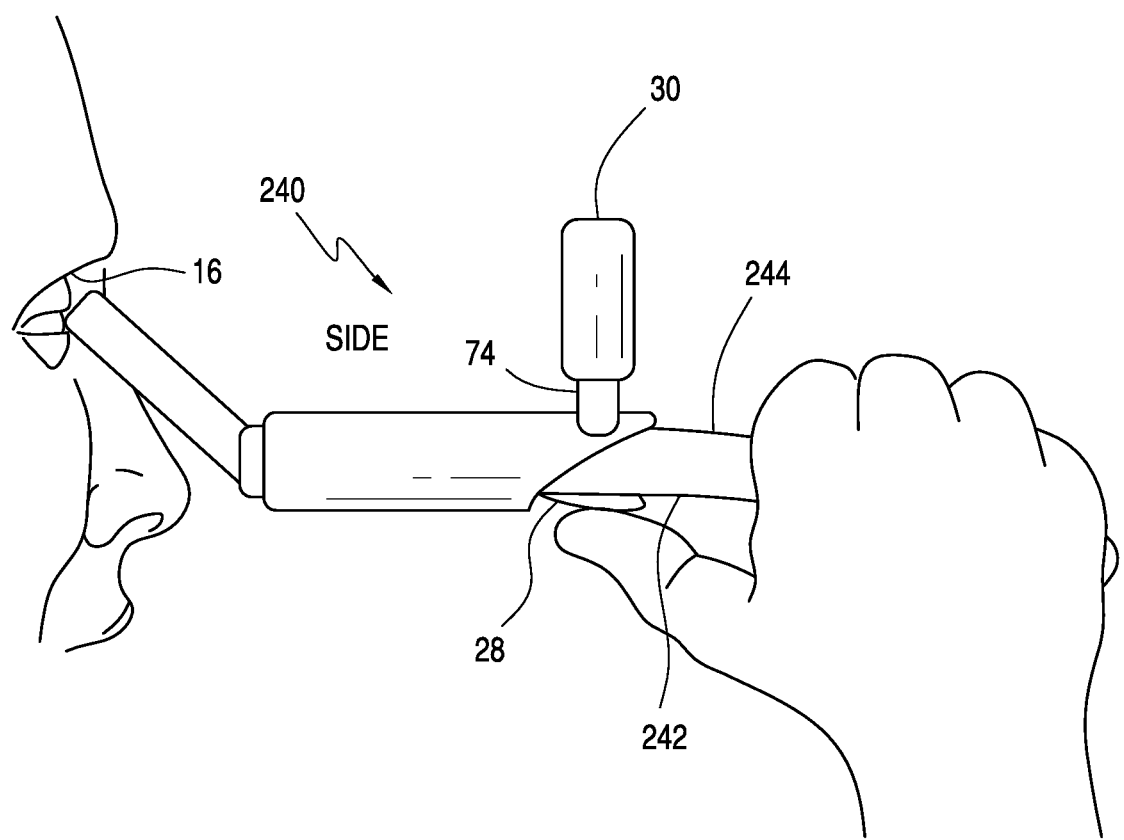
FIG. 28 is a side view of the sensing device of FIG. 23 in operation.
Figure 29:
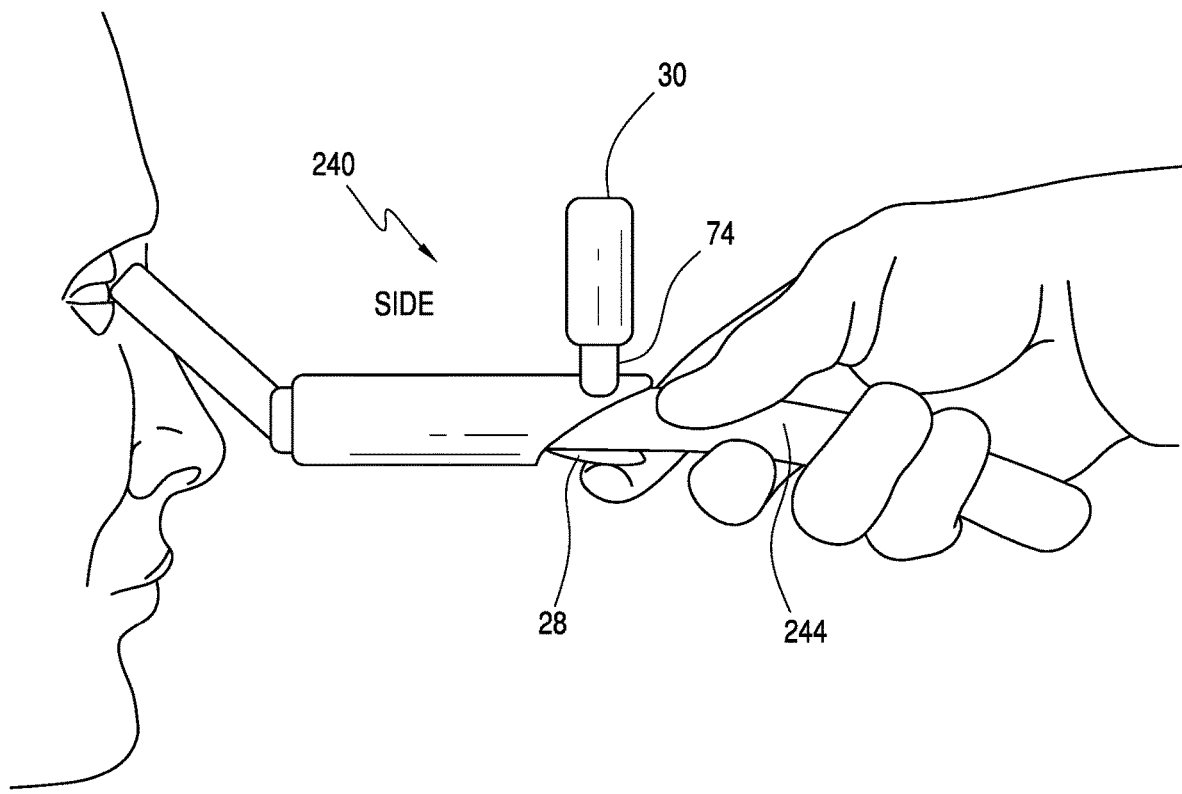
FIG. 29 is a side view of the sensing device of FIG. 23 in operation.

An exemplary distance of viewer portion 30 from second flee end 22 to body 20 adjacent to device 26 is 10 cm, the distance of viewer portion 30 from second free end 22 to body 20 adjacent to device 26 is preferably 15 cm, and the distance of viewer portion 30 from second free end 22 to body 20 adjacent to device 26 is more preferably 25 cm, and the distance of viewer portion 30 from second free end 22 to body 20 adjacent to device 26 is most preferably 40 cm. In FIG. 27A, viewer portion 30 is configured to include a rotating mechanism 25. Viewer 30 is configured to be mounted or positioned on handle 24. In an exemplary embodiment, handle 24 is configured to include a housing 27 for storage of viewer 30. The position of viewer 30 in handle 24 allows a better distance for a patient to see viewer 30, as shown in FIG. 27A.

In the alternate embodiments shown in FIGS. 30-39, the lower or attachment portion 136 or 158 is mounted, positioned, or attached to one side of body portion 134 or 152, respectively, as opposed to other embodiments where the lower or attachment portion is mounted, positioned, or attached on an upper surface of the body portion. The slide screen or viewing portion may be positioned on either side of the body portion of the sensing device. The slide screen or viewing portion may also be configured to be easily repositioned or moved between sides to meet the viewer's preference and depending on which ABTT target area is being measured; i.e., the left ABTT terminus or the right ABTT terminus.

In an exemplary embodiment of the disclosure, the slide screen portion will have a design in the form of images or text displayed thereon to divert the viewer's attention form the sensing portion of the device. In this embodiment, the images or text may be a printed, drawn, or projected image; for example, a cartoon, quote, photograph or other still image, video clip, or an advertisement may be displayed. It should be understood that any combination of images and text may be incorporated that would distract a patient or subject being measured from the sensing portion of the sensing device. Such images or text may be stored in non-volatile memory, may be received wirelessly from another device, such as a computer, satellite receiver, cable box, or the like, or may be received wirelessly from the internet or a cellular system.

In a case where the slide screen design is an advertisement, for example, it may be necessary to remove the current slide or image and replace it with another with a more current advertisement. In an exemplary embodiment, the slide screen or viewing portion may be mounted or configured using a type of sliding mechanism that allows the slide screen to be removable, as well as a fastener such as a pin or clip. In a preferred embodiment, the lower portion of the slide screen comprises circuitry (not shown) designed to connect with a receiving portion (not shown) of the body portion of the sensing device that, when the viewing portion is mounted to the body portion of the sensing device, allows the viewing portion to be activated. In an exemplary embodiment, switch 28 of the sensing device may also be linked to the connection of the slide screen so that the sensing device may not be activated without a slide screen appropriately positioned or mounted in place.

In an exemplary embodiment, the slide screen or viewing portion can have a radio frequency ID (RFID) tag, a chip, an electrical pad, or other apparatus for connecting the slide screen or viewing portion with the electrical circuitry (not shown) of the sensing device, thereby activating the sensing device for measurement. In a variation of this exemplary embodiment, it would be necessary for the operator to purchase a new slide screen or viewing portion occasionally to continue taking measurements with the sensing device. The slide screen or viewing portion can include non-volatile memory or time monitoring apparatus to allow an expiration to be used to determine the life of a particular slide screen or viewing portion, i.e., determine the time period or interval in which a particular slide screen or viewing portion can activate the sensing device for measurement. In another exemplary embodiment, a clock (not shown) to allow a specific period of time for use of the device can be used. In addition, the internal clock or a counter as part of the internal circuitry (not shown) of the sensing device can be used to determine the life of the sensing device and/or the number of measurements available. Note that this exemplary embodiment can be used for any previous embodiment of a thermometer or other measuring device, in addition to embodiments that include a slide screen or viewing portion. In a further exemplary embodiment, the slide screen or the body portion of the sensing device may comprise a controller or processor (not shown) and a separate display configured to notify the operator when a threshold period of time has been exceeded and the current slide must be replaced.

In an alternate embodiment, the slide screen may be comprised of a display that may be, for example, an LCD screen where images in the form of video are displayed. In this embodiment, the slide screen or body portion of the device may comprise, in addition to the necessary circuitry and controller or processor (not shown), an internet connection or wireless transmission capabilities, as well as a speaker, an audio jack, an earphone connection, or other component for providing the viewer with audio content. In such embodiments, the slide screen would not need to be removable as new content could be uploaded without the need to physically remove and replace the slide screen.

In an alternate embodiment, the slide screen or viewing portion may configured to display content, either in the form of still images or video images, on both sides so that the viewer and the operator are both exposed to content. The slide screen or viewing portion may display the same information on both sides, or it may display different content to each of the viewer and operator. For example, on a device that is used in a doctor's office, an advertisement targeted towards consumers may be displayed on the portion of the display facing the viewer. On the other, opposite side, facing the operator, display may present a thermal display to help locate ABTT terminus 16, or an advertisement that may be, for example, a pharmaceutical advertisement targeting medical professionals. It should be understood that, in accordance with the above description, the slide screen with dual displays may be constructed of any appropriate material and may be of any appropriate shape and size. In an alternate embodiment, the slide screen may have two displays for video content, such as LCD displays and the like, which are each in the same component, but which are facing in opposite directions. This dual-sided display could be connected to display the same content on both sides. Alternatively, the dual-sided displays could be independent, separately connected, or disconnected to enable displaying two independent images.

In an alternate embodiment, the slide screen component, digital viewer, or display, instead of being mounted onto a handheld device as described above, may be mounted onto another support structure for measuring, continuously monitoring, or treating biological parameters using ABTT terminus 16. Non-limiting examples of such support structures are clips, eyeglasses, goggles, masks, helmets, caps, headbands, and other wearable or non-wearable support structures, including table-top or wall mounted. It should be understood that the apparatus disclosed herein can be used for treatment, and in such embodiments the sensing portion is replaced by a treating portion such as including an apparatus, device, or mechanism to deliver heat or cold to ABTT terminus 20, or any other type of electrical or electromagnetic energy.

In home use, or in other situations where an ABTT sensing device is used or transported where a mirror is not readily available, it would be convenient to provide such a mirror to enable a person to take their own measurements. A mirror may be incorporated into a transport container, shown in FIGS. 49-51 and indicated generally at 300. Transport container 300 includes a storage compartment 302 configured to hold the ABTT sensing device, and a lid portion 304. Lid portion 304 includes a first end 306, which is movably fixed or attached to storage compartment 302 by a hinge or magnetic apparatus to allow for about 270 degrees of rotation about a pivot axis 310 positioned on first end 306; a second end 308, which includes a ledge portion 312 that is configured to rotate at least 45 degrees about a ledge pivot axis 314 located at second end 308 of lid portion 304, and a mirror portion 316 fixed to lid portion 304.

Transport container or box 300 is configured to provide safe storage of a sensing device or apparatus in a home use setting and is configured to provide a container for transportation so the ABTT sensing device could be readily available for temperature measurements away from home in settings such as, for example, travel, sporting events, competitions, and outdoor activities. Storage compartment 302 of transport container 300 may include an insert (not shown) designed to fit the size and shape of the ABTT sensing device exactly, so that the sensing device does not shift around during movement. This insert could be made of any suitable material that is soft and protective, such as plastic which is covered in felt or cloth, a foam, a gel, or a cushion material that has been shaped to hold specific portions of the ABTT sensing device. It should be understood that any suitable material may be used for both the composition of the box itself and for the composition of the interior of the storage compartment inside, including any insert or padding. In an exemplary embodiment, mirrored lid portion 304 is designed to enable a user to see their face easily, so as to assist a user in guiding the device towards ABTT target area 16 with ease and accuracy. Since the ABTT sensing device or apparatus is a handheld device, the sensing device may not always be operated when a mirror is easily accessible. In such situations as a sporting event or outdoor activity, as described hereinabove, a mirror may be difficult to find. As shown in FIGS. 49-51, transport container 300 is configured and arranged so that lid portion 304 may be rotated approximately 270 degrees around lid pivot axis 310 so that lid portion 304 creates an approximately 90 degree angle with respect to a bottom portion 318 of transport container 300, thus acting as a supporting arm. The stability of transport container 300 is achieved by including complimentary magnetic fasteners or other suitable fasteners, such as hinges, in storage compartment 302 and in lid portion 304. This configuration allows mirror 316 to be displayed stably so a user may then, without having to hold or support storage container 300 by hand, easily see ABTT target area 16 to guide a sensing portion for measurements using the sensing device. Once a measurement has been taken, the ABTT sensing device or apparatus may be returned to storage compartment 302, and lid portion 304 may then be returned to its original position to serve as a cover for storage compartment 302.

As is described hereinabove, the sensing portion of the apparatus comprises a sensor for gathering brain temperature measurement data or any biological parameter data. This sensor is, in turn, connected to various devices, apparatuses, or mechanism configured to transmit, convert, report, and store data, such as input and output coupling circuits, display circuits, processors, converters, connectors, and non-transitory memory (not shown). In an exemplary embodiment, these components are located in the body portion of the sensing device, such as body portion 20 of sensing device 10, are connected using the appropriate circuitry and wires to the sensing portion of the sensing apparatus, such as sensing portion 12 of sensing device 10. In alternate embodiments, the system components may be located in the sensing portion itself, or may be suitably located in another portion of the device. The components of the system are connected to a power source, such as a battery or other such internal power source (not shown). It should be understood that a variety of external power sources, such as electromagnetic coupling, can be used, including an ultra-capacitor charged externally through electromagnetic induction coupling and cells that can be recharged by an external oscillator.

In order to report and display temperature measurements, the sensing apparatus must be configured to transmit the finalized measurement value to the user. The transmission directly to the user, without the use of a receiver, may be in the form of a simple light or sound alarm (not shown), which is configured to alert when a specific temperature threshold has been obtained or surpassed. It should be understood that such an alarm may also use a combination of one or more lights and sound. The sound may be a noise such as a buzzer, beep, or other tone, or may be a reproduction of a human voice or other such sound. Measurement data may also be displayed as a numerical value on a digital or LCD screen built into the sensing apparatus, such as viewing portion 30 of sensing device 10. In such an embodiment, the system would comprise a display output module to convey the temperature value to the display. Such output module may include a software portion to providing proper formatting of the data, and a hardware portion for configuring the information for display. Aside from displaying a numerical value, data may be displayed in the form of charts, spectra, or other visual data presentation arrangements.

Also included in the present disclosure is an apparatus for remotely transmitting temperature and/or biological parameter data. Such an apparatus includes an output transmitter module and a receiver module (not shown). The transmission of data may be executed using passive radio transmission, active radio transmission, or communication by fixed cable. Ultrasonic micro-circuits may also be used for transmission, for which the signal may be transmitted using modulated sound signals, particularly under water because sound is less attenuated by water than are radio waves. In alternate embodiments, the output transmission module may be configured to transmit data via a wireless cellular network or internet network, phone network, or the like.

The present invention also provides a method for detecting body temperature, including the steps of providing a temperature detector positioned near ABTT terminus 16 during temperature detection, and determining the temperature based on the infrared radiation detected or sensed at ABTT terminus area 16. In another embodiment, the method is based on the anatomy of the ABTT terminus 16 on the surface of the skin. The method includes scanning of the area between the eye and the eyebrow, and in particular, using an arc shape movement of the probe or sensing portion, which follows the curvature of the eyelid from the tear punctum all the way up into the middle of the eyelid following the area of skin between the eye and the eye brow. Such scanning can extend into other areas of the face, head, and neck from the main starting point between the eye and the eyebrow and alternatively including the tear punctum and conjunctival area. The method includes a step of positioning a sensor, such as sensing portion 12 including IR sensor 42, between the eye and eyebrow, and making lateral, vertical, or circular movements between the eye and the eyebrow, with a controller or processor in the sensing device adapted to identify the highest temperature and report this high temperature. It should be understood that ABTT terminus 16 may have as a boundary, as shown in FIG. 62, a nose 322, in addition to an eye 324, and an eyebrow 326, and that an ABTT scanning area 328 may include an area surrounded by those boundaries. Preferably, ABTT scanning area 328 includes, as shown in FIG. 62, an area surrounded by nose 322 and a medial third 330 of the area between the eye and eyebrow. In an exemplary embodiment, scanning area 328 is an area surrounding ABTT terminus 16 of 10 centimeters in diameter that can be measured for comparison to ABTT terminus 16. In another exemplary embodiment, scanning area 328 is an area surrounding ABTT terminus 16 of 8 centimeters in diameter that can be measured for comparison to the ABTT terminus 16. In yet another exemplary embodiment, scanning area 328 is an area surrounding ABTT terminus 16 of 6 centimeters in diameter that can be measured for comparison to ABTT terminus 16. In yet a further exemplary embodiment, scanning area 328 is an area surrounding ABTT terminus 16 of 3 centimeters in diameter that can be measured for comparison to ABTT terminus 16. It should be understood that the area scanned preferably includes areas of a truncated circle up to the eyebrow and below the eyebrow.

A series of sounds can be used to provide feedback to identify ABTT terminus 16. The lack of sound is an indication that the highest temperature between the eye and eyebrow has been found, in a typical situation where ABTT terminus 16 has a higher temperature than the surrounding skin, or an indication where the lowest temperature between the eye and eyebrow has been found, in the less common situation where ABTT terminus 16 has a lower temperature than the surrounding skin. One light or a series of lights (e.g., an LED) in the sensing device would also stop illuminating when the hottest temperature of the area between the eye and the eyebrow was found. The steps include positioning a temperature sensor (contact or non-contact) for resting on the skin or viewing the skin without contacting the skin, the skin corresponding to the skin between the eye and the eyebrow that correspond to ABTT terminus 16. A next step includes making a motion with the IR sensor to cover the area between the eye and the brow, the motion preferably following the curvature of the groove between the eye and the eyebrow, more preferably in the medial portion (or nasal portion) of the area between the eye and the eyebrow, and adjacent to the nose. Scanning may also include automatically the scanning diameters described herein. It should also be understood that the area between the eyes can be used, and also that both left and right ABTT terminuses 20 can be scanned or measured. A subsequent step includes detecting the highest temperature between the eye and the eyebrow (except in situations where the surrounding skin is warmer than ABTT terminus 16), and then reporting the highest (or lowest) temperature between the eye and the eyebrow.

Figure 53:
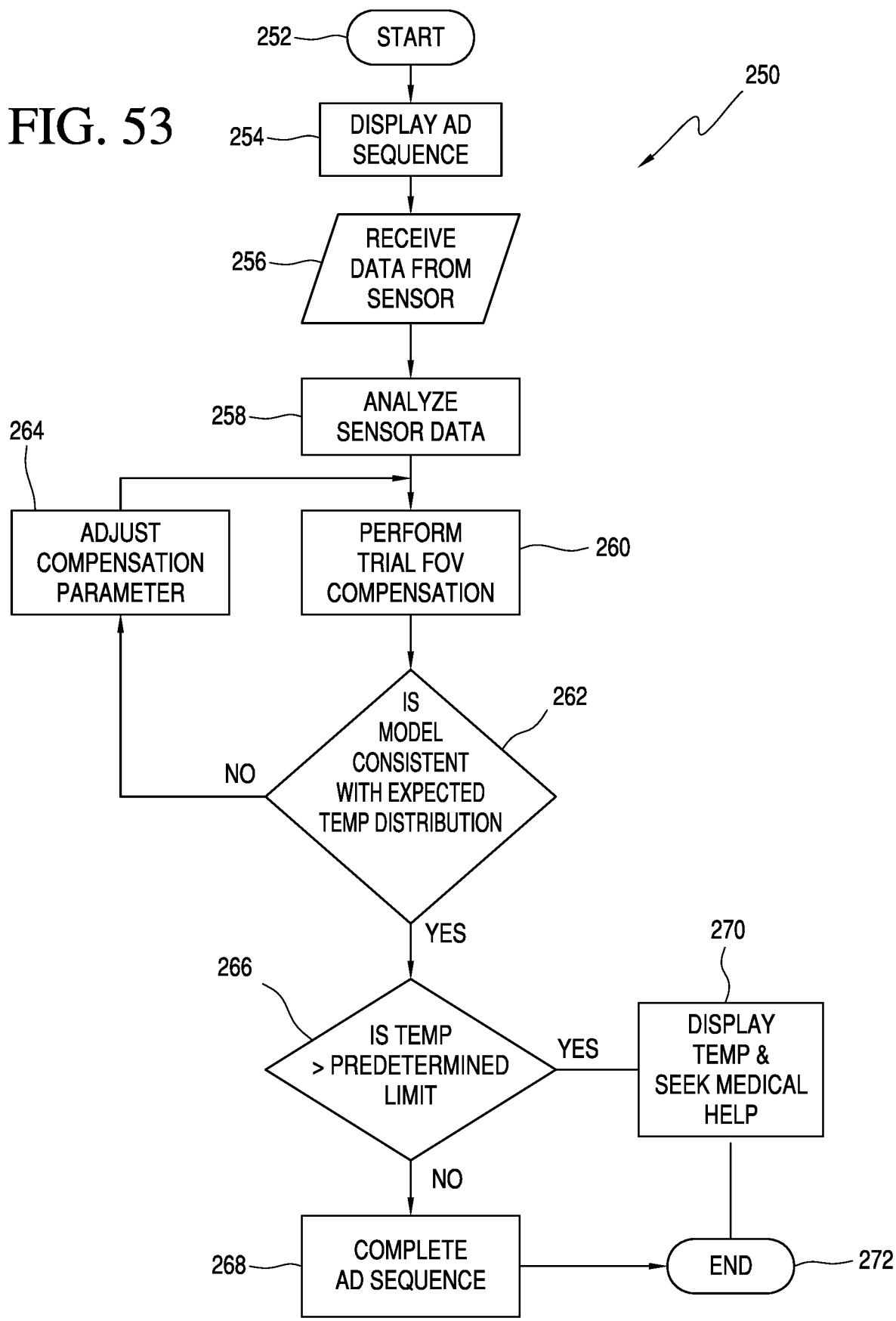
FIG. 53 is a sensing process in accordance with an exemplary embodiment of the present disclosure.

A sensing device or apparatus may operate in a variety of modes of operation. One such operational sequence is described in FIGS. 53-59. FIG. 53 shows a sensing process, generally indicated at 250. Sensing process 250 begins with a start process 252, where various registers may be reset to zero or default values, systems are provided with power, and other initializing functions for a sensing device, such as sensing device 10, are performed. Once start process 252 is finished, control passes from start process 252 to a display ad sequence 254.

Figure 54:
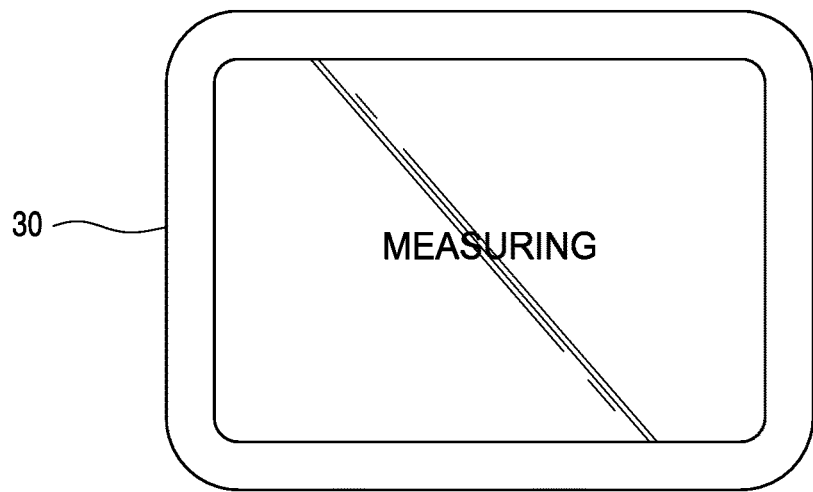
FIG. 54 is a viewing portion showing an indication of a measurement in accordance with an exemplary embodiment of the present disclosure.
Figure 55:
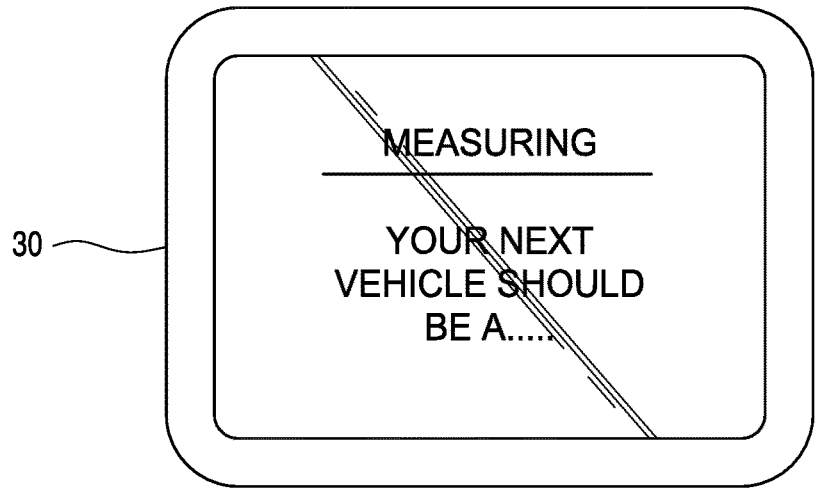
FIG. 55 is the viewing portion of FIG. 54 showing a portion of an advertising sequence in accordance with an exemplary embodiment of the present disclosure.
Figure 56:
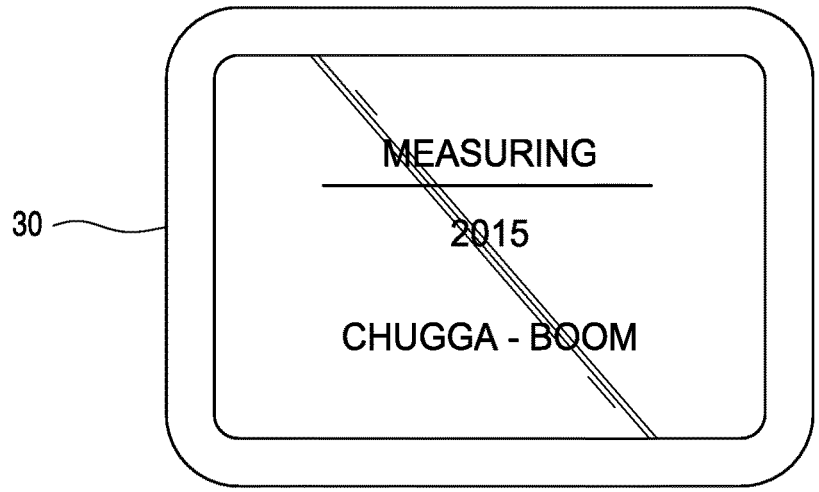
FIG. 56 is the viewing portion of FIG. 54 showing another portion of an advertising sequence in accordance with an exemplary embodiment of the present disclosure.

In display ad sequence 254, a display or viewing portion, such as display or viewing portion 30, may display a "measuring" screen, such as is shown in FIG. 54, followed by a series of advertisements, such as those shown in FIGS. 55-58. During the display of one or more advertisements, a portion of display 30 may indicate that the sensing device is measuring temperature, for example, by indicating "measuring" somewhere on viewing portion 30. Once the ad sequence is started, control passes from display ad sequence 254 to a receive sensor data process 256.

In receive sensor data process 256, data is received from an IR sensor, such as IR sensor 42 positioned in sensing portion 12. The data is stored in a memory location (not shown) for later processing. Once data is received from IR sensor 42, control passes from receive sensor data process 256 to an analyze sensor data process 258, where the data received from IR sensor 42 is analyzed to determine one or more features of the signal from IR sensor 42, such as temperature or any biological parameter such as glucose. Control then passes from analyze sensor data process 258 to a perform field of view (FOV) compensation process 260.

In FOV compensation process 260, the data from IR sensor 42 is analyzed to compensate for non-ABTT terminus data. Such analysis may be by simple geometric subtraction of temperatures below a peak value, integration of peak temperature areas, curve fitting, or other analysis. In some embodiments, the sensing device is measuring relative temperature with time, and such compensation may be unnecessary, and may be de-selected via optional controls not shown. Once data from IR sensor 42 has been analyzed, control passes to a test data process 262.

In test data process 262, the validity of the compensated data is tested. If the data is not valid, e.g., the indicated temperature is outside anticipated predetermined limits, control passes to an adjust compensation parameters process 264. If the indicated temperature data is valid, then control passes to a temperature limit process 266.

In adjust compensation parameters process 264, compensation parameters are modified prior to performing FOV compensation process 260 again. Once compensation parameters are adjusted, process 250 continues at FOV compensation process 260 as previously described.

Returning to temperature limit process 266, it is determined whether the temperature exceeds a predetermined limit. In an exemplary embodiment, the predetermined temperature may be 104 degrees F. If the predetermined temperature limit is reached or exceeded, control passes from temperature limit process 266 to a display temperature and guidance process 270. Otherwise, control passes from temperature limit process 266 to a complete ad sequence process 268.

Figure 57:
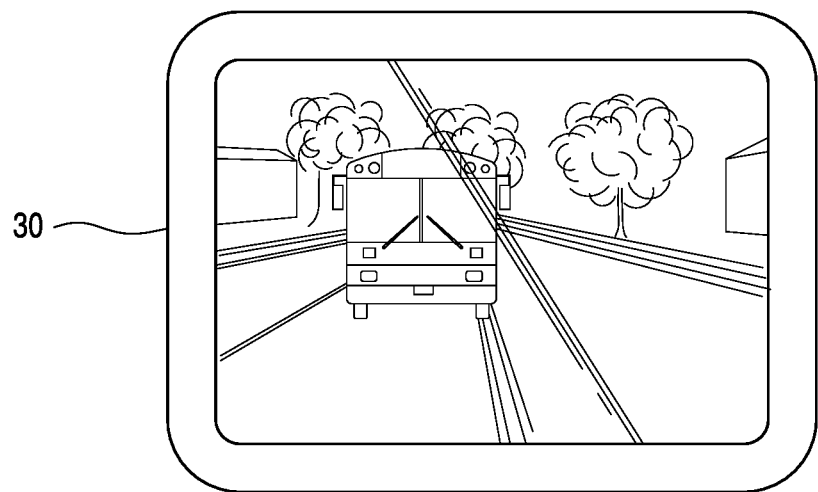
FIG. 57 is the viewing portion of FIG. 54 showing yet another portion of an advertising sequence in accordance with an exemplary embodiment of the present disclosure.
Figure 58:
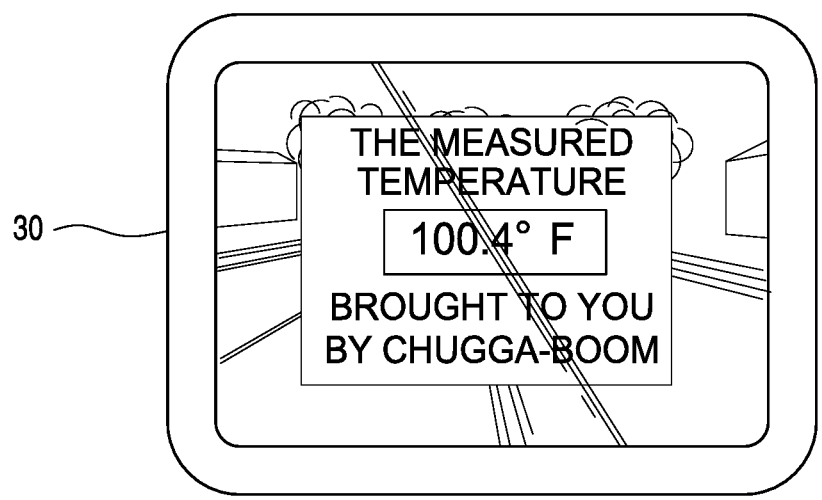
FIG. 58 is the viewing portion of FIG. 54 showing a measured temperature in combination with a portion of an advertising sequence in accordance with an exemplary embodiment of the present disclosure.

In ad sequence process 268, the previously displayed ad sequence transitioned from the display shown in FIG. 57 to a display shown in FIG. 58, wherein sensor data, shown in FIG. 58 as a temperature, is displayed on a portion of the advertisement from FIG. 57. In the example of FIG. 58, the temperature is displayed on an enlarged portion of a license plate of a vehicle shown in FIG. 57. A similar transition may be from signage associated with a commercial or retail store, packaging of a product, or other images associated with an advertiser. Furthermore, as shown in FIG. 58, the temperature is "brought to you" by an advertiser. In an exemplary embodiment, temperature data is configured to be shown in a random manner in relation to the time of the advertisement and in relation as to how the temperature value will be displayed. In a car advertisement, for example, the numerical information or data, e.g., temperature data, can be substituted for the number of a license plate. In another exemplary embodiment, a grocery store advertisement may show the numerical value, data, or information, e.g., temperature data, by replacing a price of a product with the numerical value, data, or information.

The benefit of the interactive advertisements shown in FIGS. 57 and 58 is that the payments from the advertisers can help subsidize the cost of the sensing device, making exemplary sensing devices described herein more affordable for home use and for clinical use, such as doctor's offices and hospitals. In the event that a user is uninterested in advertisements, an option may be presented to purchase a code for the specific sensing device to eliminate the advertisements, with each sensing device including its own, unique code, to prevent hacking of a code in one device and transporting the hack to all other devices. It should be understood that the apparatus includes an input apparatus, device, or mechanism such as keypad, touch screen, voice, and the like for entering a code.

Figure 59:
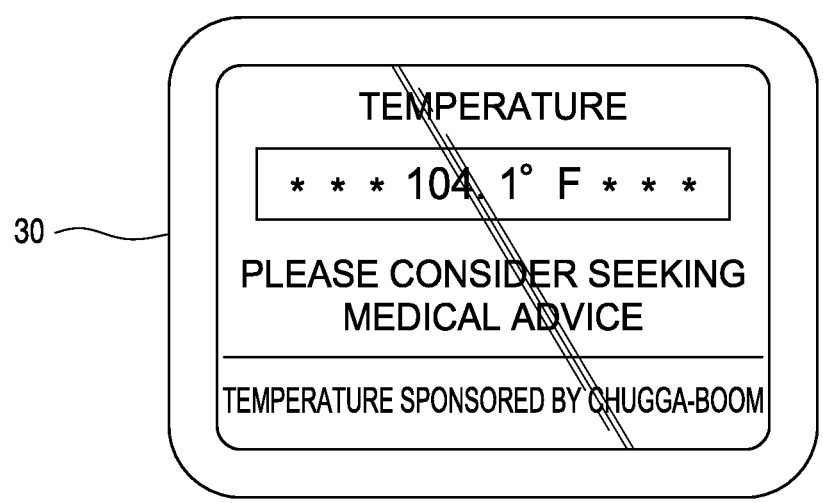
FIG. 59 is the viewing portion of FIG. 54 showing a temperature with a recommendation to consider seeking medical advice in addition to a sponsor message in accordance with an exemplary embodiment of the present disclosure.

Returning to display temperature and guidance process 270, if the measurement temperature is outside predetermined limits that may constitute a need for medical guidance, for example a call to a doctor or nurse, a trip to the doctor, or a trip to the emergency room, as soon as the temperature data is available, the display shown in FIG. 59 is presented, with guidance that assistance from a medical practitioner should be considered. A sponsoring message may also be presented in the display of FIG. 59, but will be subservient, i.e., smaller or de-emphasized, as compared to the temperature, which may be in color, such as red, and may flash, along with a suggestion to seek medical attention or advice.

Once process 268 or process 270 are finished, and after a suitable, predetermined interval, such as an interval in the range of 10 seconds to 60 seconds, control passes to an end process 272, where viewing portion 30 may power off, IR sensor 42 may power off, and other portions of the sensing device may power down to conserve power, which may be battery power or other power.

While various embodiments of the disclosure have been shown and described, it is understood that these embodiments are not limited thereto. The embodiments may be changed, modified, and further applied by those skilled in the art. Therefore, these embodiments are not limited to the detail shown and described previously herein, but also include all such changes and modifications. It should also be understood that any part of series of parts of any embodiment can be used in another embodiment, and all of those combinations are within the scope of the disclosure.

I claim:

1. A method for measuring a temperature of a brain by way of an Abreu brain thermal tunnel (ABTT) comprising:
    positioning a sensor configured to measure a temperature of an ABTT toward a terminus of the ABTT of the subject located between an eye and an eyebrow of the subject with a handle attached to a housing on which the sensor is mounted;
    displaying an advertisement and a message informing the subject that a measurement is being performed on a display that is attached to and protrudes from the housing such that the display is projected into the line of sight of a user and the display is spaced further from the user than the sensor;

measuring a temperature of the terminus of the ABTT with the sensor;

producing a signal corresponding to the measured temperature from the sensor; and reporting a temperature produced by the signal.

2. The method of claim 1, further comprising adjusting the temperature of an area surrounding the terminus of the ABTT.

3. The method of claim 1, further comprising using the ABTT to measure a biological parameter, including a plurality of chemical compounds present in a human body.

4. The method of claim 3, further comprising identifying a radiation signature or a thermal signature of an element as received from the terminus of the ABTT to identify a presence or a concentration of the plurality of chemical compounds.

5. The method of claim 3, wherein the plurality of chemical compounds includes glucose, cholesterol, alcohol, analytes present in the body, chemicals received by the body, elements produced by the body, and microorganisms present in the body.

6. The method of claim 3, wherein the one or more of the plurality of chemical compounds is measured at the terminus of the ABTT with a spectroscope.

7. The method of claim 1, wherein the sensor includes a convex surface configured to mate with the terminus of the ABTT, the convex surface including an opening for entry of radiation from the terminus of the ABTT.

8. The method of claim 1, wherein the sensor automatically scans a head of the subject to identify a location of the terminus of the ABTT according to a predetermined scan pattern.

9. The method of claim 8, wherein the scan is a circular spiral.

10. The method of claim 9, wherein the scan begins at a center of the circular spiral and moves outwardly from the center.

11. The method of claim 9, wherein the scan begins at an outer periphery of the circular spiral and moves inwardly toward a center of the circular spiral.

12. The method of claim 8, wherein the scan is in up and down directions beginning at a nose of the subject.

13. The method of claim 8, wherein the scan is in left and right directions toward and away from a nose of the subject.

14. The method of claim 1, wherein a field of view of the terminus of the ABTT is compensated for data that is not from the terminus of the ABTT, the field of view including the terminus of the ABTT and an area surrounding the terminus of the ABTT.

15. The method of claim 1, further comprising displaying information on the display that indicates that medical advice should be sought upon a determination that a predetermined temperature is exceeded.

16. The method of claim 1, wherein the measured temperature is displayed on the display.

17. The method of claim 16, wherein the measured temperature and information that indicates that medical advice should be sought are provided on the display concurrently.

18. The method of claim 1, wherein to orient the sensor for collecting emissions from the terminus of the ABTT, the sensor is rotatable about an axis that extends perpendicular to the vertical and rotatable relative to a housing on which the sensor is mounted to select the angle.

19. The method of claim 1, wherein the first direction of the handle is movable with respect to a fixed position of the sensor.

20. The method of claim 1, wherein the advertisement is terminated upon determination that a predetermined temperature is exceeded.

* * * * *